United States Patent
Ripa et al.

(10) Patent No.: US 10,196,374 B2
(45) Date of Patent: Feb. 5, 2019

(54) 1-ALKYL-6-OXO-1,6-DIHYDROPYRIDIN-3-YL COMPOUNDS AND USE AS SGRM MODULATORS

(71) Applicant: AstraZeneca AB, Sodertalje (SE)

(72) Inventors: Lena Elisabeth Ripa, Mölndal (SE); Karolina Lawitz, Cheshire (GB); Matti Juhani Lepistö, Mölndal (SE); Martin Hemmerling, Mölndal (SE); Karl Edman, Mölndal (SE); Antonio LLinas, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 15/513,655

(22) PCT Filed: Sep. 23, 2015

(86) PCT No.: PCT/EP2015/071862
§ 371 (c)(1),
(2) Date: Nov. 10, 2017

(87) PCT Pub. No.: WO2016/046260
PCT Pub. Date: Mar. 31, 2016

(65) Prior Publication Data
US 2017/0298041 A1    Oct. 19, 2017

Related U.S. Application Data

(60) Provisional application No. 62/055,822, filed on Sep. 26, 2014.

(51) Int. Cl.
*C07D 401/14* (2006.01)
*C07D 401/04* (2006.01)

(52) U.S. Cl.
CPC .................. *C07D 401/04* (2013.01)

(58) Field of Classification Search
CPC .................................................. C07D 401/14
See application file for complete search history.

(56) References Cited

U.S. PATENT DOCUMENTS

2008/0214641 A1* 9/2008 Berger ................ C07D 231/56
514/405

FOREIGN PATENT DOCUMENTS

WO    WO 2008/076048    6/2008
WO    WO 2009/142569    11/2009

OTHER PUBLICATIONS

International Preliminary Report on Patentability in International Application No. PCT/EP2015/071862, dated Mar. 28, 2017.
International Search Report for International Application No. PCT/EP2015/071862, dated Nov. 9, 2015.

* cited by examiner

*Primary Examiner* — Timothy R Rozof

(57) ABSTRACT

This specification generally relates to 1-alkyl-6-oxo-1,6-dihydropyridin-3-yl compounds (including salts thereof). This specification also relates to pharmaceutical compositions and kits comprising such a compound, uses of such a compound (including treatment methods and medicament preparations), and processes for making such a compound.

15 Claims, No Drawings

1-ALKYL-6-OXO-1,6-DIHYDROPYRIDIN-3-YL COMPOUNDS AND USE AS SGRM MODULATORS

CROSS-REFERENCE TO RELATED APPLICATIONS

This application is a U.S. National Stage application of International Application No. PCT/EP2015/071862, filed on Sep. 23, 2015, said International Application No. PCT/EP2015/071862 claims benefit under 35 U.S.C. § 119(e) of the U.S. Provisional Application No. 62/055,822, filed Sep. 26, 2014. Each of the above listed applications is incorporated by reference herein in its entirety for all purposes.

FIELD OF THE SPECIFICATION

This specification generally relates to 1-alkyl-6-oxo-1,6-dihydropyridin-3-yl compounds (including salts thereof). This specification also relates to pharmaceutical compositions and kits comprising such a compound, uses of such a compound (including treatment methods and medicament preparations), and processes for making such a compound.

BACKGROUND

Glucocorticoids (GCs) have been used for decades to treat acute and chronic inflammatory and immune conditions, including rheumatoid arthritis, asthma, chronic obstructive pulmonary disease ("COPD"), osteoarthritis, rheumatic fever, allergic rhinitis, systemic lupus erythematosus, Crohn's disease, inflammatory bowel disease, and ulcerative colitis. Examples of GCs include dexamethasone, prednisone, and prednisolone. Unfortunately, GCs are often associated with severe and sometimes irreversible side effects, such as osteoporosis, hyperglycemia, effects on glucose metabolism (diabetes mellitus), skin thinning, hypertension, glaucoma, muscle atrophy, Cushing's syndrome, fluid homeostasis, and psychosis (depression). These side effects can particularly limit the use of GCs in a chronic setting. Thus, a need continues to exist for alternative therapies that possess the beneficial effects of GCs, but with a reduced likelihood of side effects.

GCs form a complex with the GC receptor (GR) to regulate gene transcription. The GC-GR complex translocates to the cell nucleus, and then binds to GC response elements (GREs) in the promoter regions of various genes. The resulting GC-GR-GRE complex, in turn, activates or inhibits transcription of proximally located genes. The GC-GR complex also (or alternatively) may negatively regulate gene transcription by a process that does not involve DNA binding. In this process, termed transrepression, the GC-GR complex enters the nucleus and directly interacts (via protein-protein interaction) with other transcription factors, repressing their ability to induce gene transcription and thus protein expression.

Some of the side effects of GCs are believed to be the result of cross-reactivity with other steroid receptors (e.g., progesterone, androgen, mineralocorticoid, and estrogen receptors), which have somewhat homologous ligand binding domains; and/or the inability to selectively modulate gene expression and downstream signaling. Consequently, it is believed that an efficacious selective GR modulator (SGRM), which binds to GR with greater affinity relative to other steroid hormone receptors, would provide an alternative therapy to address the unmet need for a therapy that possesses the beneficial effects of GCs, while, at the same time, having fewer side effects.

A range of compounds have been reported to have SGRM activity. See, e.g., WO2007/0467747, WO2007/114763, WO2008/006627, WO2008/055709, WO2008/055710, WO2008/052808, WO2008/063116, WO2008/076048, WO2008/079073, WO2008/098798, WO2009/065503, WO2009/142569, WO2009/142571, WO2010/009814, WO2013/001294, and EP2072509. Still, there continues to be a need for new SGRMs that exhibit, for example, an improved potency, efficacy, effectiveness in steroid-insensitive patients, selectivity, solubility allowing for oral administration, pharmacokinetic profile allowing for a desirable dosing regimen, stability on the shelf (e.g., hydrolytic, thermal, chemical, or photochemical stability), crystallinity, tolerability for a range of patients, side effect profile and/or safety profile.

SUMMARY OF THE SPECIFICATION

This specification is directed to, inter alia, 1-alkyl-6-oxo-1,6-dihydropyridin-3-yl compounds; methods of treatment using the 1-alkyl-6-oxo-1,6-dihydropyridin-3-yl compounds (e.g., uses of the compounds to treat various conditions and as pharmacological tools); use of the 1-alkyl-6-oxo-1,6-dihydropyridin-3-yl compounds to make medicaments; compositions comprising the 1-alkyl-6-oxo-1,6-dihydropyridin-3-yl compounds (e.g., pharmaceutical compositions); kits comprising the 1-alkyl-6-oxo-1,6-dihydropyridin-3-yl compounds; methods for manufacturing the 1-alkyl-6-oxo-1,6-dihydropyridin-3-yl compounds; and intermediates used in such manufacturing methods.

Briefly, this specification is directed, in part, to a compound of Formula I or a salt thereof. Formula I corresponds to:

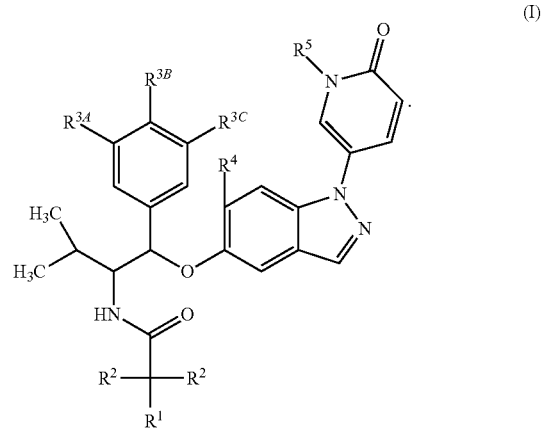

(I)

Here:
$R^1$ is selected from halo, methyl and halomethyl.
Each $R^2$ is an independently selected halo.
Each of $R^{3A}$, $R^{3B}$ and $R^{3C}$ is independently selected from H, halo, halomethyl and halomethoxy.
$R^4$ is selected from H, halo and methyl.
$R^5$ is selected from methyl and ethyl.

This specification also is directed, in part, to oral pharmaceutical compositions. Such compositions comprise a compound of Formula I (or pharmaceutically acceptable salt), and a pharmaceutically acceptable excipient.

This specification also is directed, in part, to a compound of Formula I (or pharmaceutically acceptable salt) for use as a medicament.

This specification also is directed, in part, to a compound of Formula I (or pharmaceutically acceptable salt) for the therapy of a condition (generally a disorder) mediated by (or otherwise associated with) the glucocorticoid receptor.

This specification also is directed, in part, to a compound of Formula I (or pharmaceutically acceptable salt) for treating rheumatoid arthritis.

This specification also is directed, in part, to the use of a compound of Formula I (or pharmaceutically acceptable salt) for the manufacture of a medicament.

This specification also is directed, in part, to the use of a compound of Formula I (or pharmaceutically acceptable salt) for the manufacture of a medicament for the therapy of a condition (generally a disorder) mediated by (or otherwise associated with) the glucocorticoid receptor.

This specification also is directed, in part, to the use of a compound of Formula I (or pharmaceutically acceptable salt) for the manufacture of a medicament for treating rheumatoid arthritis.

This specification also is directed, in part, to a method for treating a condition (generally a disorder) mediated by (or otherwise associated with) the glucocorticoid receptor in a mammal (e.g., a human) in need of such treatment. The method comprises administering a therapeutically effective amount a compound of Formula I (or pharmaceutically acceptable salt) to the mammal.

This specification also is directed, in part, to a method for treating rheumatoid arthritis in a mammal (e.g., a human) in need of such treatment. The method comprises administering a therapeutically effective amount a compound of Formula I (or pharmaceutically acceptable salt) to the mammal.

The specification also is directed, in part, to a kit. The kit comprises a compound of Formula I (or pharmaceutically acceptable salt) thereof. The kit also comprises an apparatus for administering the compound (or pharmaceutically acceptable salt) to a mammal (e.g., a human); instructions for administering the compound (or pharmaceutically acceptable salt) to a mammal (e.g., a human); an excipient; or a pharmaceutically active ingredient other than the compound of Formula I (or pharmaceutically acceptable salt).

Further aspects of Applicant's invention will be apparent to one skilled in the art from reading this specification.

DESCRIPTION OF ILLUSTRATIVE EMBODIMENTS

This description of illustrative embodiments is intended only to acquaint others skilled in the art with Applicant's invention, its principles, and its practical application so that others skilled in the art may readily adapt and apply the specification in its numerous forms, as they may be best suited to the requirements of a particular use. This description and its specific examples, while indicating embodiments of this specification, are intended for purposes of illustration only. This specification, therefore, is not limited to the illustrative embodiments described in this specification, and may be variously modified. In addition, it is to be appreciated that various features of the specification that are, for clarity reasons, described in the context of separate embodiments, also may be combined to form a single embodiment. Conversely, various features of the specification that are, for brevity reasons, described in the context of a single embodiment, also may be combined to form subcombinations thereof.

A. THE COMPOUNDS

As noted above, this specification is directed, in part, to a compound of Formula I or a salt thereof. Formula I corresponds to:

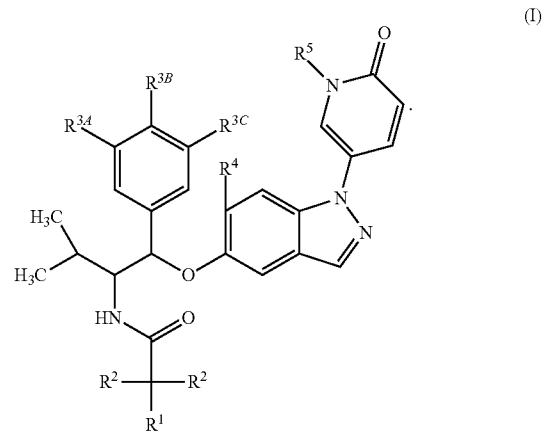

(I)

In general, $R^1$ is selected from the group consisting of halo, methyl and halomethyl.

In some embodiments, $R^1$ is halo. In some such embodiments, $R^1$ is fluoro.

In some embodiments, $R^1$ is methyl.

In some embodiments, $R^1$ is halomethyl.

In general, each $R^2$ is an independently selected halo.

In some embodiments, each $R^2$ is fluoro.

In some embodiments, $R^1$ is halo, and each $R^2$ is fluoro. In some such embodiments, $R^1$ is fluoro, and each $R^2$ is fluoro In some embodiments, $R^1$ is methyl, and each $R^2$ is fluoro.

In general, each of $R^{3A}$, $R^{3B}$ and $R^{3C}$ is independently selected from H, halo, halomethyl and halomethoxy.

In some embodiments, each of $R^{3A}$, $R^{3B}$ and $R^{3C}$ is independently selected from H, fluoro, chloro, trifluoromethyl, difluoromethoxy and trifluoromethoxy.

In some embodiments, at least one of $R^{3A}$, $R^{3B}$ and $R^{3C}$ is H.

In some embodiments, at least one of $R^{3A}$, $R^{3B}$ and $R^{3C}$ is H; and each of the remaining two of $R^{3A}$, $R^{3B}$ and $R^{3C}$ is independently selected from H, fluoro, chloro, trifluoromethyl, difluoromethoxy and trifluoromethoxy.

In some embodiments, only one of $R^{3A}$, $R^{3B}$ and $R^{3C}$ is H. In some such embodiments, $R^{3A}$ is H. In other such embodiments, $R^{3B}$ is H.

In some embodiments, $R^{3B}$ is H, and each of $R^{3A}$ and $R^{3C}$ is halo. In some such embodiments, each of $R^{3A}$ and $R^{3C}$ is fluoro. In other such embodiments, each of $R^{3A}$ and $R^{3C}$ is chloro.

In some embodiments, two (and not more than two) of $R^{3A}$, $R^{3B}$ and $R^{3C}$ are each H.

In some embodiments, $R^{3A}$ and $R^{3B}$ are each H

In some embodiments, $R^{3A}$ and $R^{3B}$ are each H, and $R^{3c}$ is halo. In some such embodiments, $R^{3c}$ is fluoro. In other such embodiments, $R^{3c}$ is chloro.

In some embodiments, $R^{3A}$ and $R^{3C}$ are each H.

In some embodiments, $R^{3A}$ and $R^{3C}$ are each H, and $R^{3B}$ is halo. In some such embodiments, $R^{3B}$ is fluoro. In other such embodiments, $R^{3B}$ is chloro.

In some embodiments, $R^{3A}$ and $R^{3C}$ are each H, and $R^{3B}$ is halomethyl. In some such embodiments, $R^{3B}$ is trifluoromethyl.

In some embodiments, $R^{3A}$ and $R^{3C}$ are each H, and $R^{3B}$ is halomethoxy. In some such embodiments, $R^{3B}$ is difluoromethoxy. In other such embodiments, $R^{3B}$ is trifluoromethoxy.

In some embodiments, all of $R^{3A}$, $R^{3B}$ and $R^{3C}$ are each H.

In general, $R^4$ is selected from H, halo and methyl.

In some embodiments, $R^4$ is H.

In some embodiments, $R^4$ is halo. In some such embodiments, $R^4$ is chloro.

In some embodiments, $R^4$ is methyl.

In general, $R^5$ is selected from methyl and ethyl.

In some embodiments, $R^5$ is methyl.

In some embodiments, $R^5$ is ethyl.

In some embodiments, the compound of the above embodiments corresponds in structure to Formula (IA):

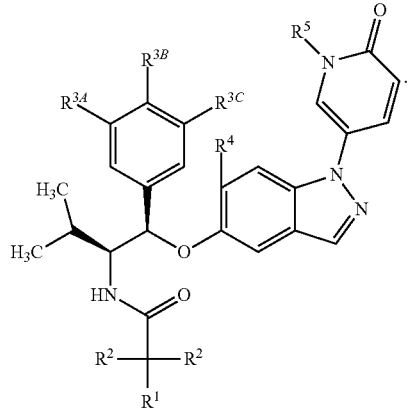

(IA)

Compounds of Formula I include, for example, the following:

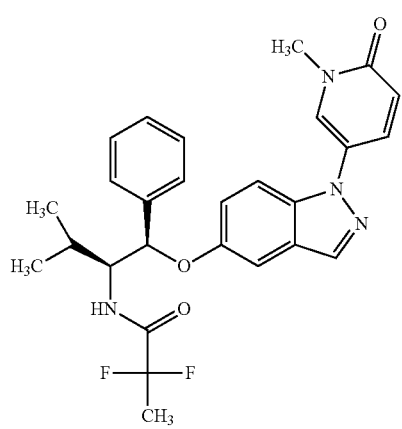

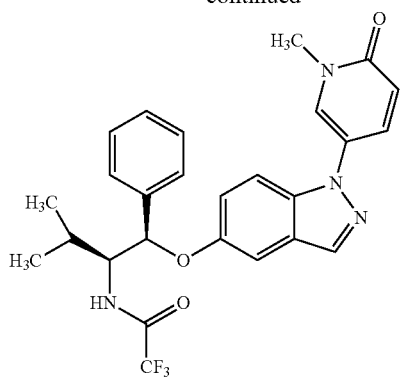

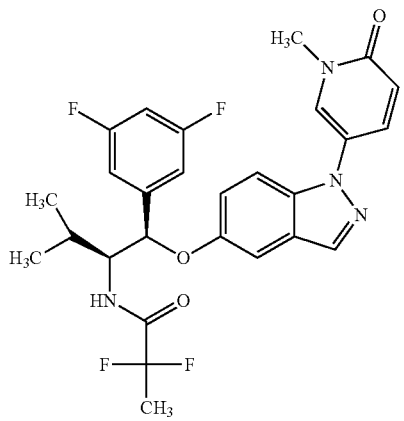

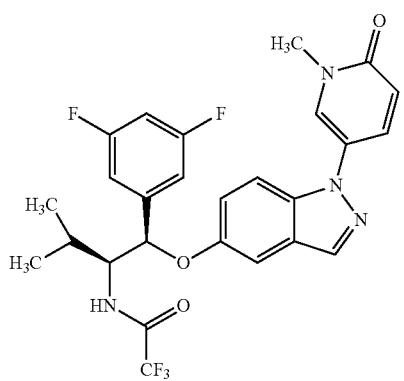

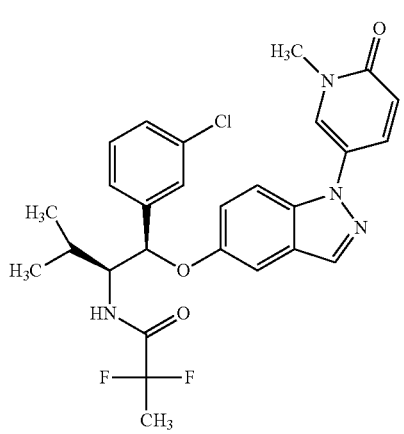

7
-continued
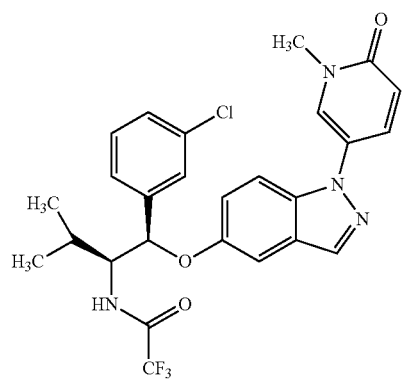
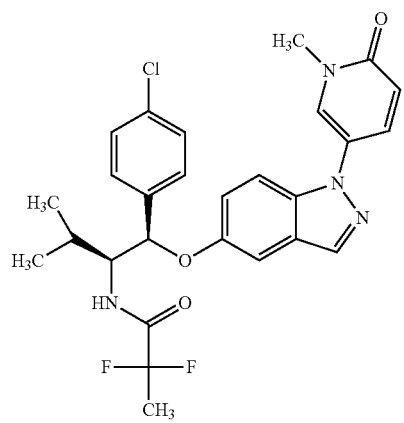
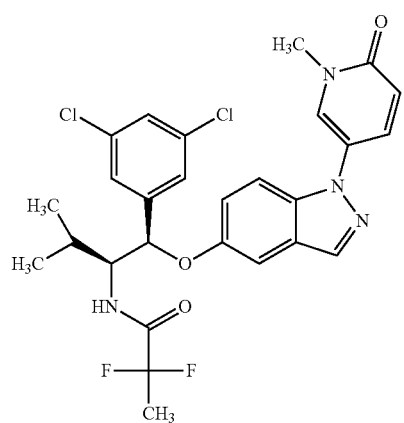
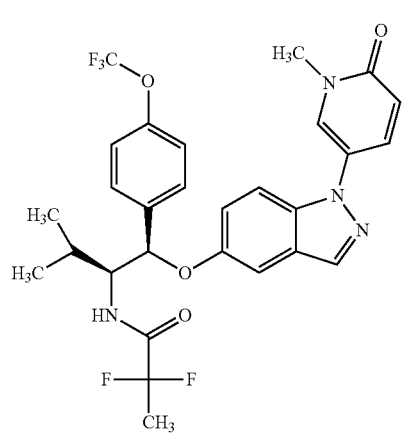
8
-continued
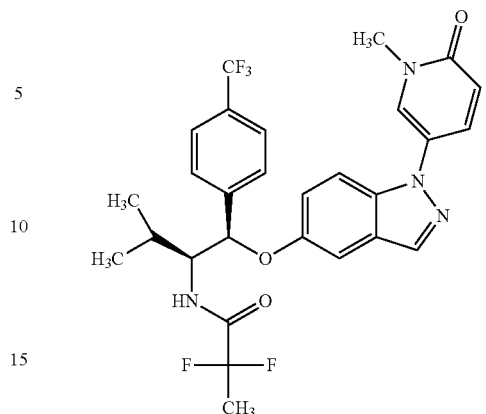
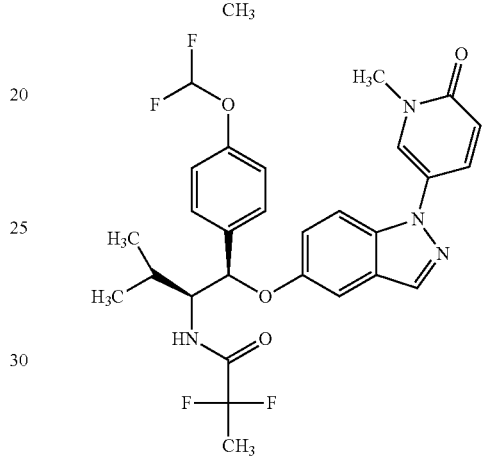
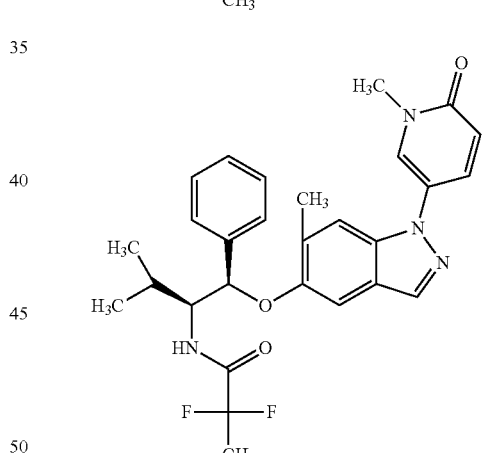
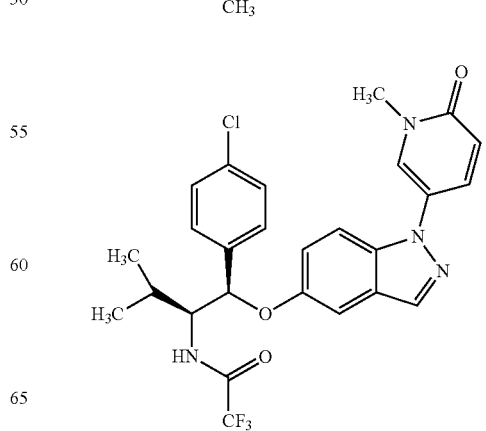

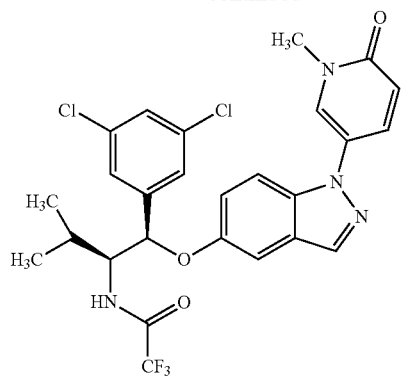
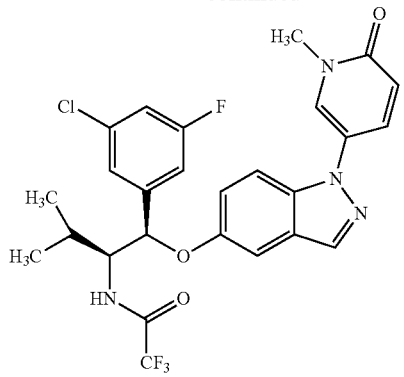
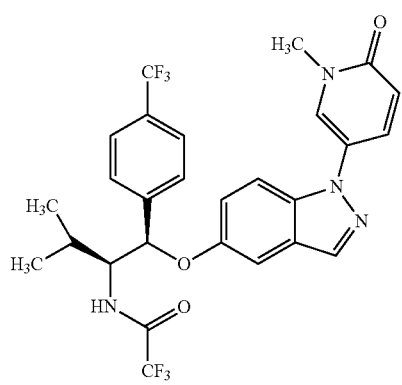
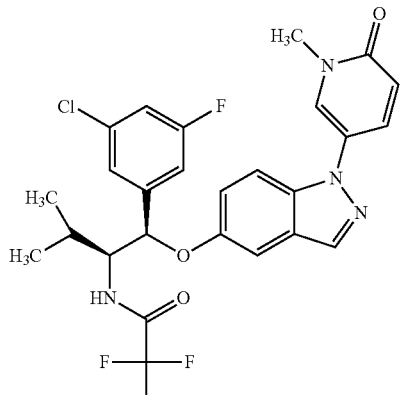
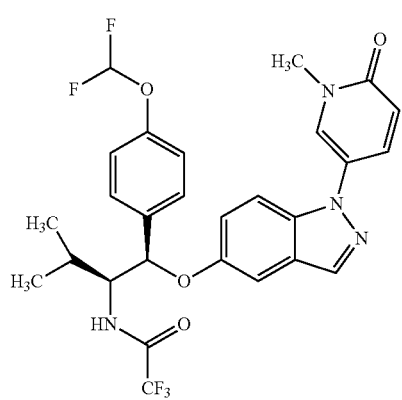
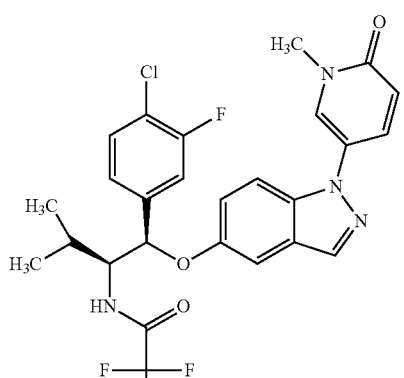
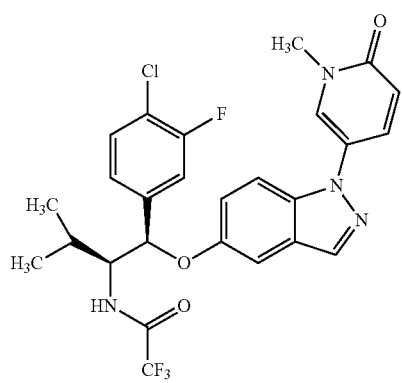
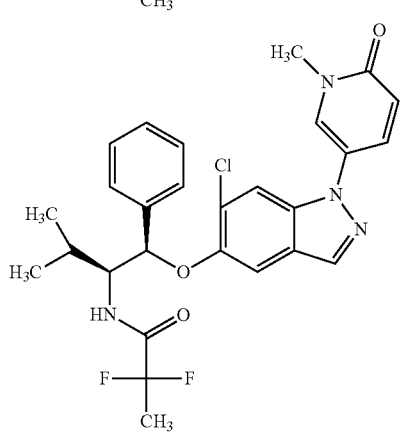

-continued

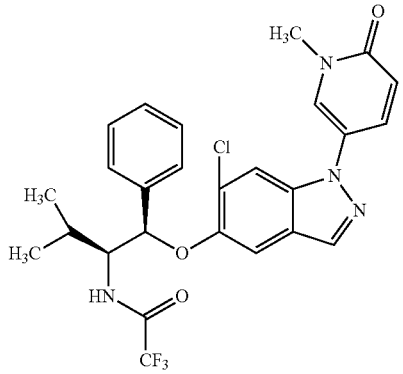

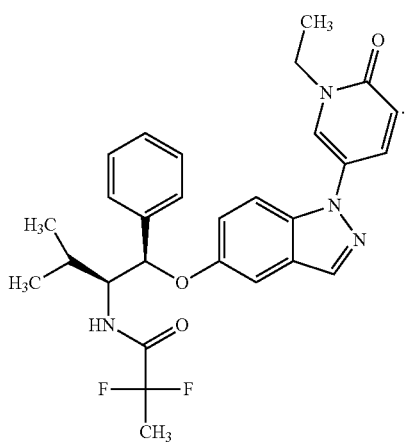

Some embodiments are directed to a compound corresponding to the following structure (or a pharmaceutically acceptable salt thereof):

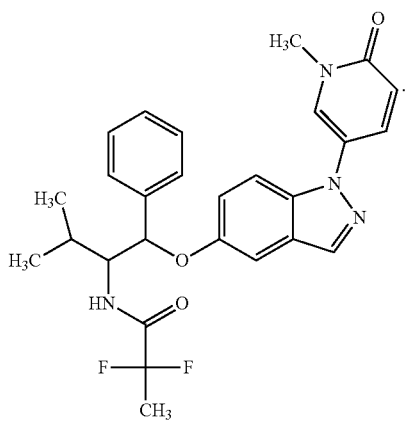 [SMILES: CC(C)C(NC(=O)C(C)(F)F)C(Oc1ccc2c(cnn2-c2ccc(=O)n(C)c2)c1)c1ccccc1]

In some such embodiments, the compound corresponds to the following structure (or is a pharmaceutically acceptable salt thereof):

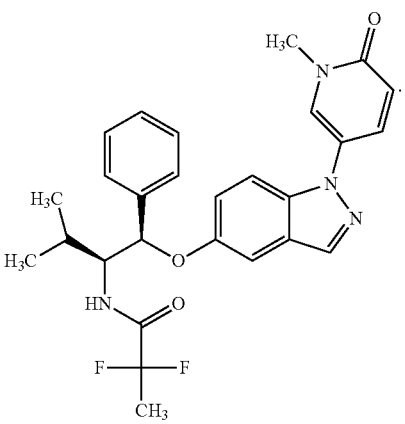 [SMILES: CC(C)[C@H](NC(=O)C(C)(F)F)[C@H](Oc1ccc2c(cnn2-c2ccc(=O)n(C)c2)c1)c1ccccc1]

Some embodiments are directed to a compound corresponding to the following structure (or a pharmaceutically acceptable salt thereof):

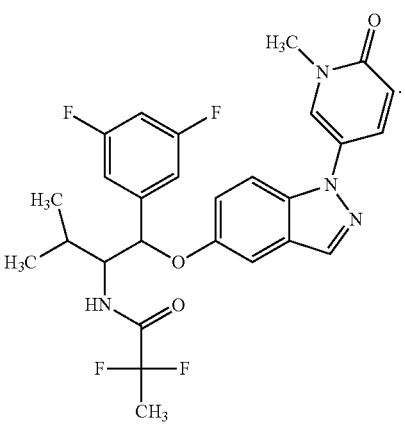 [SMILES: CC(C)C(NC(=O)C(C)(F)F)C(Oc1ccc2c(cnn2-c2ccc(=O)n(C)c2)c1)c1cc(F)cc(F)c1]

In some such embodiments, the compound corresponds to the following structure (or is a pharmaceutically acceptable salt thereof):

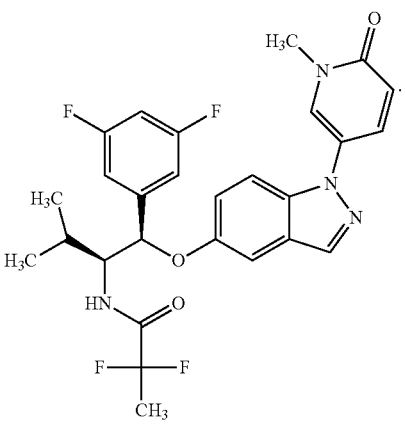 [SMILES: CC(C)[C@H](NC(=O)C(C)(F)F)[C@H](Oc1ccc2c(cnn2-c2ccc(=O)n(C)c2)c1)c1cc(F)cc(F)c1]

Some embodiments are directed to a compound corresponding to the following structure (or a pharmaceutically acceptable salt thereof):

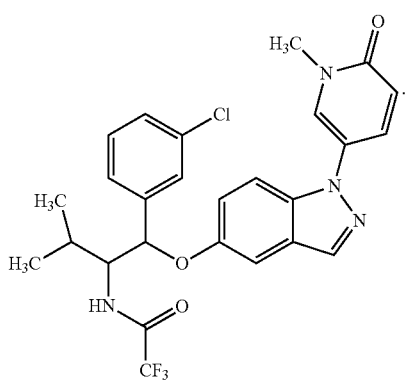 [SMILES: CC(C)C(NC(=O)C(F)(F)F)C(Oc1ccc2c(cnn2-c2ccc(=O)n(C)c2)c1)c1cccc(Cl)c1]

In some such embodiments, the compound corresponds to the following structure (or is a pharmaceutically acceptable salt thereof):

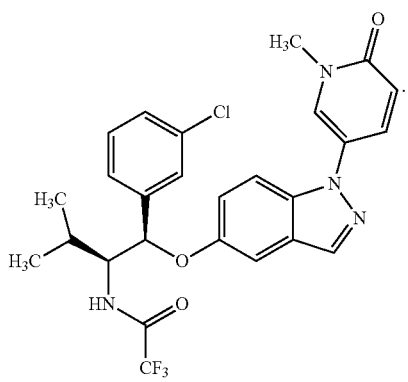 [SMILES: CC(C)[C@H](NC(=O)C(F)(F)F)[C@H](Oc1ccc2c(cnn2-c2ccc(=O)n(C)c2)c1)c1cccc(Cl)c1]

In some embodiments, compounds and salts of this specification exhibit one or more of the following characteristics: a desirable potency, efficacy, effectiveness in steroid-insensitive patients, selectivity, solubility allowing for oral administration, pharmacokinetic profile allowing for a desirable dosing regimen, stability on the shelf (e.g., hydrolytic, thermal, chemical, or photochemical stability), crystallinity, tolerability for a range of patients, side effect profile and/or safety profile.

In some embodiments, the compound of Formula I (or pharmaceutically acceptable salt thereof) is both a partial agonist and partial antagonist of the glucocorticoid receptor. In some embodiments, the compound of Formula I (or pharmaceutically acceptable salt thereof) exhibits activity in both assays in Example 24 below, with both a transactivation agonist effect of less than 50% in the GRE Agonist Assay and a transactivation antagonist effect of greater than 50% in the GRE Antagonist Assay.

The compounds of Formula I include at least two chiral centers. To the extent a structure or chemical name in this patent does not indicate the chirality, the structure or name is intended to encompass any single chiral isomer corresponding to that structure or name, as well as any mixture of chiral isomers (e.g., the racemate). In some embodiments, a single chiral isomer is obtained by isolating it from a mixture of isomers (e.g., a racemate) using, for example, chiral chromatographic separation. In other embodiments, a single chiral isomer is obtained through direct synthesis from, for example, a chiral starting material.

In some embodiments, the compounds of Formula I are in the form of a non-salt.

In some embodiments, the compounds of Formula I are in the form of a salt. In some such embodiments, the salts are acid addition salts. In general, an acid addition salt can be prepared using various inorganic or organic acids. Such salts can typically be formed by, for example, mixing the compound with an acid (e.g., a stoichiometric amount of acid) using various methods known in the art. This mixing may occur in water, an organic solvent (e.g., ether, ethyl acetate, ethanol, isopropanol, or acetonitrile), or an aqueous/organic mixture.

A salt may be advantageous due to one or more of its chemical or physical properties, such as stability in differing temperatures and humidities, or a desirable solubility in water, oil, or other solvent. In some instances, a salt may be used to aid in the isolation or purification of the compound. In some embodiments (particularly where the salt is intended for administration to an animal, or is a reagent for use in making a compound or salt intended for administration to an animal), the salt is pharmaceutically acceptable.

Examples of inorganic acids that typically may be used to form acid addition salts include hydrochloric, hydrobromic, hydroiodic, nitric, carbonic, sulfuric, and phosphoric acid. Examples of organic acids include, for example, aliphatic, cycloaliphatic, aromatic, araliphatic, heterocyclic, carboxylic, and sulfonic classes of organic acids. Specific examples of organic salts include cholate, sorbate, laurate, acetate, trifluoroacetate, formate, propionate, succinate, glycolate, gluconate, digluconate, lactate, malate, tartaric acid (and derivatives thereof, e.g., dibenzoyltartrate), citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate (and derivatives thereof), embonate (pamoate), ethanesulfonate, benzenesulfonate, pantothenate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

The compounds of Formula I and salts thereof are intended to encompass any isotopically-labeled (or "radio-labeled") derivatives of a compound of Formula I or salt thereof. Such a derivative is a derivative of a compound of Formula I or salt thereof wherein one or more atoms are replaced by an atom having an atomic mass or mass number different from the atomic mass or mass number typically found in nature. Examples of radionuclides that may be incorporated include $^2H$ (also written as "D" for deuterium), $^3H$ (also written as "T" for tritium), $^{11}C$, $^{13}C$, $^{14}C$, $^{13}N$, $^{15}N$, $^{15}O$, $^{17}O$, $^{18}O$, $^{18}F$, $^{36}Cl$, $^{82}Br$, $^{75}Br$, $^{76}Br$, $^{77}Br$, $^{123}I$, $^{124}I$, $^{125}I$, and $^{131}I$. The radionuclide that is used will depend on the specific application of that radio-labeled derivative. For example, for in vitro receptor labeling and competition assays, $^3H$ or $^{14}C$ are often useful. For radio-imaging applications, $^{11}C$ or $^{18}F$ are often useful. In some embodiments, the radionuclide is $^3H$. In some embodiments, the radionuclide is $^{14}C$. In some embodiments, the radionuclide is $^{11}C$. And in some embodiments, the radionuclide is $^{18}F$.

It is contemplated that the compounds of Formula I and salts thereof may have various solid state forms. It also is contemplated that the compounds of Formula I and salts thereof may be in a non-solvated form or in the form of a solvate (e.g., a hydrate).

It also is contemplated that a compound of Formula I or a salt thereof may be linked to a coupling partner by, for example, being chemically coupled to the compound or salt or physically associated with it. Examples of coupling partners include a label or reporter molecule, a supporting substrate, a carrier or transport molecule, an effector, a drug, an antibody, or an inhibitor. Coupling partners can be covalently linked to a compound or salt via an appropriate functional group on the compound, such as a hydroxyl, carboxyl, or amino group. Other derivatives include formulating a compound or salt with liposomes.

B. MEDICAL USES

Because of their ability to bind to the glucocorticoid receptor, Applicant believes the compounds described in this specification are useful as anti-inflammatory agents, and can also display antiallergic, immunosuppressive and anti-proliferative actions. Thus, it is contemplated compounds of Formula I (including pharmaceutically acceptable salts thereof) can be used as a medicament for the treatment or prophylaxis of one or more of the following conditions (generally a disorder) in a mammal:

(i) lung diseases, which coincide with inflammatory, allergic and/or proliferative processes, including chronically obstructive lung diseases of any origin (including bronchial asthma, chronic obstructive pulmonary disease (COPD)), bronchitis of different origins, adult respiratory distress syndrome (ARDS), acute respiratory distress syndrome, bronchiectases, all forms of restructive lung diseases (including allergic alveolitis), all forms of pulmonary edema (including toxic pulmonary edema), sarcoidoses, and granulomatoses (including Boeck's disease);

(ii) rheumatic diseases/auto-immune diseases/degenerative joint diseases, which coincide with inflammatory, allergic and/or proliferative processes, including all forms of rheumatic diseases (including rheumatoid arthritis, acute rheumatic fever, polymyalgia rheumatica, collagenoses, and Behcet's disease), reactive arthritis, inflammatory soft-tissue diseases of other origins, arthritic symptoms in degenerative joint diseases (arthroses), traumatic arthritides, collagen diseases of other origins (including systemic lupus erythematodes, discoid lupus erythematosus, sclerodermia, polymyositis, dermatomyositis, polyarteritis nodosa, and temporal arteritis), Sjögren's syndrome, Still syndrome, Felty's syndrome, vitiligo, and soft-tissue rheumatism;

(iii) allergies, which coincide with inflammatory, allergic and/or proliferative processes, including all forms of allergic reactions (including Quincke's edema; insect bites; allergic reactions to pharmaceutical agents, blood derivatives, contrast media, etc.; anaphylactic shock; urticaria; and allergic vascular diseases), allergic vasculitis, and inflammatory vasculitis;

(iv) vascular inflammations (vasculitides), including panarteritis nodosa, temporal arteritis, erythema nodosum, polyarteris nodosa, Wegner's granulomatosis, and giant-cell arteritis;

(v) nephropathies, which coincide with inflammatory, allergic and/or proliferative processes, including nephrotic syndrome and all nephritides (including glomerulonephritis);

(vi) liver diseases, which coincide with inflammatory, allergic and/or proliferative processes, including acute liver cell decomposition, acute hepatitis of different origins (including virally-, toxically- or pharmaceutical agent-induced), and chronically aggressive and/or chronically intermittent hepatitis;

(vii) gastrointestinal diseases, which coincide with inflammatory, allergic and/or proliferative processes, including regional enteritis (Crohn's disease), gastritis, reflux esophagitis, ulcerative colitis, and gastroenteritis of other origins (including native sprue);

(viii) proctological diseases, which coincide with inflammatory, allergic and/or proliferative processes, including anal eczema, fissures, haemorrhoids, and idiopathic proctitis;

(ix) eye diseases, which coincide with inflammatory, allergic and/or proliferative processes, including allergic keratitis, uvenitis iritis, conjunctivitis, blepharitis, optic neuritis, chorioiditis, and sympathetic ophthalmia;

(x) diseases of the ear-nose-throat area, which coincide with inflammatory, allergic and/or proliferative processes, including allergic rhinitis, hay fever, otitis externa (caused by contact dermatitis, infection, etc.), and otitis media;

(xi) neurological diseases, which coincide with inflammatory, allergic and/or proliferative processes, including cerebral edema (including tumor-induced cerebral edema), multiple sclerosis, acute encephalomyelitis, different forms of convulsions (including infantile nodding spasms), meningitis, spinal cord injury, and stroke;

(xii) blood diseases, which coincide with inflammatory, allergic and/or proliferative processes, including acquired haemolytic anemia, thrombocytopenia (including idiopathic thrombocytopenia), M. Hodgkins and Non-Hodgkins lymphomas, thrombocythemias, and erythrocytoses;

(xiii) tumor diseases, which coincide with inflammatory, allergic and/or proliferative processes, including acute lymphatic leukaemia, malignant lymphoma, lymphogranulomatoses, lymphosarcoma, and extensive metastases (including breast and prostate cancers);

(xiv) endocrine diseases, which coincide with inflammatory, allergic and/or proliferative processes, including endocrine orbitopathy, thyrotoxic crisis, de Quervain's thyroiditis, Hashimoto's thyroiditis, hyperthyroidism, Basedow's disease, granulomatous thyroiditis, lymphadenoid goiter;

(xv) transplants, which coincide with inflammatory, allergic and/or proliferative processes;

(xvi) severe shock conditions, which coincide with inflammatory, allergic and/or proliferative processes, including anaphylactic shock;

(xvii) substitution therapy, which coincides with inflammatory, allergic and/or proliferative processes, including innate primary suprarenal insufficiency (including congenital adrenogenital syndrome), acquired primary suprarenal insufficiency (including Addison's disease, autoimmune adrenalitis, meta-infective, tumors, metastases, etc.), innate secondary suprarenal insufficiency (including example congenital hypopituitarism), and acquired secondary suprarenal insufficiency (including meta-infective, tumors, etc.);

(xviii) Emesis, which coincides with inflammatory, allergic and/or proliferative processes, including in combination with a 5-HT3-antagonist in cytostatic-agent-induced vomiting;

(xix) Pains of inflammatory origins, including lumbago; and (xx) Dermatological diseases, which coincide with inflammatory, allergic and/or proliferative processes, including atopic dermatitis (including in children), exfoliative dermatitis, psoriasis, erythematous diseases (triggered by different noxae, including radiation, chemicals, burns, etc.), acid burns, bullous dermatoses (including autoimmune pemphigus vulgaris, and bullous pemphigoid), diseases of the lichenoid group, itching (including allergic origins), all forms of eczema (including atopic eczema or seborrheal eczema), rosacea, pemphigus vulgaris, erythema exudativum multiforme, erythema nodosum, balanitis, pruritis (including of allergic origin), manifestation of vascular diseases, vulvitis, inflammatory hair loss (including alopecia areata), cutaneous T-cell lymphoma, rashes of any origin or dermatoses, psoriasis and parapsoriasis groups, and *pityriasis rubra* pilaris.

Without prejudice to the foregoing, it is contemplated the compounds disclosed in this specification (including pharmaceutically acceptable salts thereof) can be used to treat conditions such as: diabetes type I (insulin-dependent diabetes), Guillain-Barré syndrome, restenoses after percutaneous transluminal angioplasty, Alzheimer's disease, acute and chronic pain, arteriosclerosis, reperfusion injury, thermal injury, multiple organ injury secondary to trauma, acute purulent meningitis, necrotizing enterocolitis and syndromes associated with hemodialysis, leukopheresis, granulocyte transfusion, Conies Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, oesophageal varicies, muscle weakness, increased melanin pigmentation of the skin, weight loss, hypotension, hypoglycemia, Cushing's Syndrome, obesity, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, rheumatic fever, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, hypercalcemia, acute adrenal insufficiency, chronic primary adrenal insufficiency, secondary adrenal insufficiency, congenital adrenal hyperplasia, Little's syndrome, systemic inflammation, inflammatory bowel disease, Wegener's granulomatosis, giant cell arthritis, osteoarthritis, angioneurotic edema, tendonitis, bursitis, autoimmune chronic active hepatitis, hepatitis, cinhosis, panniculitis, inflamed cysts, pyoderma gangrenosum, eosinophilic fasciitis, relapsing polychondritis, sarcoidosis Sweet's disease, type 1 reactive leprosy, capillary hemangiomas, lichen planus, erythema nodosum acne, hirsutism, toxic epidermal necrolysis, erythema multiform, psychoses, cognitive disorders (such as memory disturbances) mood disorders (such as depression and bipolar disorder), anxiety disorders and personality disorders.

As used herein, the term "congestive heart failure" (CHF) or 'congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As will be appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear.

Some embodiments in this specification are directed to a compound of Formula I (or a pharmaceutically acceptable salt thereof) being for use in therapy.

Some embodiments in this specification are directed to a compound of Formula I (or a pharmaceutically acceptable salt thereof) being for use in treating a GR-mediated condition (such as a condition described above).

Some embodiments in this specification are directed to a compound of Formula I (or a pharmaceutically acceptable salt thereof) being for use in treating an inflammatory or immune condition responsive to a steroidal glucocorticoid (e.g., dexamethasone, prednisone, and/or prednisolone).

Some embodiments in this specification are directed to a compound of Formula I (or a pharmaceutically acceptable salt thereof) being for use in treating an inflammatory condition.

Some embodiments in this specification are directed to a compound of Formula I (or a pharmaceutically acceptable salt thereof) being for use in treating a respiratory condition.

Some embodiments in this specification are directed to a compound of Formula I (or a pharmaceutically acceptable salt thereof) being for use in treating a rheumatic condition.

Some embodiments in this specification are directed to a compound of Formula I (or a pharmaceutically acceptable salt thereof) being for use in treating rheumatoid arthritis.

Some embodiments in this specification are directed to a compound of Formula I (or a pharmaceutically acceptable salt thereof) being for use in treating asthma.

Some embodiments in this specification are directed to a compound of Formula I (or a pharmaceutically acceptable salt thereof) being for use in treating moderate to severe asthma exacerbation.

Some embodiments in this specification are directed to a compound of Formula I (or a pharmaceutically acceptable salt thereof) being for use in treating COPD.

Some embodiments in this specification are directed to a compound of Formula I (or a pharmaceutically acceptable salt thereof) being for use in treating moderate to severe COPD exacerbation.

Some embodiments in this specification are directed to a compound of Formula I (or a pharmaceutically acceptable salt thereof) being for use in treating irritable bowel syndrome.

Some embodiments in this specification are directed to a compound of Formula I (or a pharmaceutically acceptable salt thereof) being for use in treating a collagen disorder.

Some embodiments in this specification are directed to a compound of Formula I (or a pharmaceutically acceptable salt thereof) being for use in the prophylaxis of kidney transplant rejection.

Some embodiments in this specification are directed to a compound of Formula I (or a pharmaceutically acceptable salt thereof) being for use in treating sarcoidosis.

Some embodiments in this specification are directed to a compound of Formula I (or a pharmaceutically acceptable salt thereof) being for use in treating Addison's disease.

Some embodiments in this specification are directed to a compound of Formula I (or a pharmaceutically acceptable salt thereof) being for use in treating chronic lymphocytic leukemia.

Some embodiments in this specification are directed to a compound of Formula I (or a pharmaceutically acceptable salt thereof) being for use in treating acute lymphocytic leukemia.

Some embodiments in this specification are directed to a compound of Formula I (or a pharmaceutically acceptable salt thereof) being for use in treating respiratory distress syndrome.

Some embodiments in this specification are directed to a compound of Formula I (or a pharmaceutically acceptable salt thereof) being for use in treating nephrotic syndrome.

Some embodiments in this specification are directed to a compound of Formula I (or a pharmaceutically acceptable salt thereof) being for use in treating a dermatologic disease.

Some embodiments in this specification are directed to a compound of Formula I (or a pharmaceutically acceptable salt thereof) for use in the manufacture of a medicament for therapy.

Some embodiments in this specification are directed to a compound of Formula I (or a pharmaceutically acceptable salt thereof) for use in the manufacture of a medicament for treating a GR-mediated condition (such as a condition described above).

Some embodiments in this specification are directed to a compound of Formula I (or a pharmaceutically acceptable salt thereof) for use in the manufacture of a medicament for treating an inflammatory or immune condition responsive to a steroidal glucocorticoid (e.g., dexamethasone, prednisone, and/or prednisolone).

Some embodiments in this specification are directed to a compound of Formula I (or a pharmaceutically acceptable salt thereof) for use in the manufacture of a medicament for treating an inflammatory condition.

Some embodiments in this specification are directed to a compound of Formula I (or a pharmaceutically acceptable salt thereof) for use in the manufacture of a medicament for treating a respiratory condition.

Some embodiments in this specification are directed to a compound of Formula I (or a pharmaceutically acceptable salt thereof) for use in the manufacture of a medicament for treating a rheumatic condition.

Some embodiments in this specification are directed to a compound of Formula I (or a pharmaceutically acceptable salt thereof) for use in the manufacture of a medicament for treating rheumatoid arthritis.

Some embodiments in this specification are directed to a compound of Formula I (or a pharmaceutically acceptable salt thereof) for use in the manufacture of a medicament for treating asthma.

Some embodiments in this specification are directed to a compound of Formula I (or a pharmaceutically acceptable salt thereof) for use in the manufacture of a medicament for treating moderate to severe asthma exacerbation.

Some embodiments in this specification are directed to a compound of Formula I (or a pharmaceutically acceptable salt thereof) for use in the manufacture of a medicament for treating COPD.

Some embodiments in this specification are directed to a compound of Formula I (or a pharmaceutically acceptable salt thereof) for use in the manufacture of a medicament for treating moderate to severe COPD exacerbation.

Some embodiments in this specification are directed to a compound of Formula I (or a pharmaceutically acceptable salt thereof) for use in the manufacture of a medicament for treating irritable bowel syndrome.

Some embodiments in this specification are directed to a compound of Formula I (or a pharmaceutically acceptable salt thereof) for use in the manufacture of a medicament for treating a collagen disorder.

Some embodiments in this specification are directed to a compound of Formula I (or a pharmaceutically acceptable salt thereof) for use in the manufacture of a medicament for prophylaxis of kidney transplant rejection.

Some embodiments in this specification are directed to a compound of Formula I (or a pharmaceutically acceptable salt thereof) for use in the manufacture of a medicament for treating sarcoidosis.

Some embodiments in this specification are directed to a compound of Formula I (or a pharmaceutically acceptable salt thereof) for use in the manufacture of a medicament for treating Addison's disease.

Some embodiments in this specification are directed to a compound of Formula I (or a pharmaceutically acceptable salt thereof) for use in the manufacture of a medicament for chronic lymphocytic leukemia.

Some embodiments in this specification are directed to a compound of Formula I (or a pharmaceutically acceptable salt thereof) for use in the manufacture of a medicament for treating acute lymphocytic leukemia.

Some embodiments in this specification are directed to a compound of Formula I (or a pharmaceutically acceptable salt thereof) for use in the manufacture of a medicament for treating respiratory distress syndrome.

Some embodiments in this specification are directed to a compound of Formula I (or a pharmaceutically acceptable salt thereof) for use in the manufacture of a medicament for treating nephrotic syndrome.

Some embodiments in this specification are directed to a compound of Formula I (or a pharmaceutically acceptable salt thereof) for use in the manufacture of a medicament for treating a dermatologic disease.

Some embodiments in this specification are directed to a method of treating a disease in a mammal in need of such treatment. The method comprises administering to the mammal a therapeutically effective amount of a compound of Formula I (or a pharmaceutically acceptable salt thereof).

Some embodiments in this specification are directed to a method of treating a GR-mediated condition (such as a condition described above) in a mammal in need of such treatment. The method comprises administering to the mammal a therapeutically effective amount of a compound of Formula I (or a pharmaceutically acceptable salt thereof).

Some embodiments in this specification are directed to a method of treating an inflammatory or immune condition responsive to a steroidal glucocorticoid (e.g., dexamethasone, prednisone, and/or prednisolone) in a mammal in need of such treatment. The method comprises administering to the mammal a therapeutically effective amount of a compound of Formula I (or a pharmaceutically acceptable salt thereof).

Some embodiments in this specification are directed to a method of treating an inflammatory condition in a mammal in need of such treatment. The method comprises administering to the mammal a therapeutically effective amount of a compound of Formula I (or a pharmaceutically acceptable salt thereof).

Some embodiments in this specification are directed to a method of treating a respiratory condition in a mammal in need of such treatment. The method comprises administering to the mammal a therapeutically effective amount of a compound of Formula I (or a pharmaceutically acceptable salt thereof).

Some embodiments in this specification are directed to a method of treating a rheumatic condition in a mammal in need of such treatment. The method comprises administering to the mammal a therapeutically effective amount of a compound of Formula I (or a pharmaceutically acceptable salt thereof).

Some embodiments in this specification are directed to a method of treating rheumatoid arthritis in a mammal in need of such treatment. The method comprises administering to the mammal a therapeutically effective amount of a compound of Formula I (or a pharmaceutically acceptable salt thereof).

Some embodiments in this specification are directed to a method of treating asthma in a mammal in need of such treatment. The method comprises administering to the mammal a therapeutically effective amount of a compound of Formula I (or a pharmaceutically acceptable salt thereof).

Some embodiments in this specification are directed to a method of treating moderate to severe asthma exacerbation in a mammal in need of such treatment. The method comprises administering to the mammal a therapeutically effective amount of a compound of Formula I (or a pharmaceutically acceptable salt thereof).

Some embodiments in this specification are directed to a method of treating COPD in a mammal in need of such treatment. The method comprises administering to the mammal a therapeutically effective amount of a compound of Formula I (or a pharmaceutically acceptable salt thereof).

Some embodiments in this specification are directed to a method of treating moderate to severe COPD exacerbation in a mammal in need of such treatment. The method comprises administering to the mammal a therapeutically effective amount of a compound of Formula I (or a pharmaceutically acceptable salt thereof).

Some embodiments in this specification are directed to a method of treating irritable bowel syndrome in a mammal in need of such treatment. The method comprises administering to the mammal a therapeutically effective amount of a compound of Formula I (or a pharmaceutically acceptable salt thereof).

Some embodiments in this specification are directed to a method of treating a collagen disorder in a mammal in need of such treatment. The method comprises administering to the mammal a therapeutically effective amount of a compound of Formula I (or a pharmaceutically acceptable salt thereof).

Some embodiments in this specification are directed to a method of prophylaxis of kidney transplant rejection in a mammal in need of such treatment. The method comprises administering to the mammal a therapeutically effective amount of a compound of Formula I (or a pharmaceutically acceptable salt thereof).

Some embodiments in this specification are directed to a method of treating sarcoidosis in a mammal in need of such treatment. The method comprises administering to the mammal a therapeutically effective amount of a compound of Formula I (or a pharmaceutically acceptable salt thereof).

Some embodiments in this specification are directed to a method of treating Addison's disease in a mammal in need of such treatment. The method comprises administering to the mammal a therapeutically effective amount of a compound of Formula I (or a pharmaceutically acceptable salt thereof).

Some embodiments in this specification are directed to a method of treating chronic lymphocytic leukemia in a mammal in need of such treatment. The method comprises administering to the mammal a therapeutically effective amount of a compound of Formula I (or a pharmaceutically acceptable salt thereof).

Some embodiments in this specification are directed to a method of treating acute lymphocytic leukemia in a mammal in need of such treatment. The method comprises administering to the mammal a therapeutically effective amount of a compound of Formula I (or a pharmaceutically acceptable salt thereof).

Some embodiments in this specification are directed to a method of treating respiratory distress syndrome in a mammal in need of such treatment. The method comprises administering to the mammal a therapeutically effective amount of a compound of Formula I (or a pharmaceutically acceptable salt thereof).

Some embodiments in this specification are directed to a method of treating nephrotic syndrome in a mammal in need of such treatment. The method comprises administering to the mammal a therapeutically effective amount of a compound of Formula I (or a pharmaceutically acceptable salt thereof).

Some embodiments in this specification are directed to a method of treating a dermatologic disease in a mammal in need of such treatment. The method comprises administering to the mammal a therapeutically effective amount of a compound of Formula I (or a pharmaceutically acceptable salt thereof).

In some embodiments, the methods of treatment described above comprise orally administering to the mammal a therapeutically effective amount of a compound of Formula I (or a pharmaceutically acceptable salt thereof).

In some embodiments, the treated mammal in the above-described methods of treatment is a human.

In some embodiments, the treated mammal in the above-described methods of treatment is a mammal other than a human. Such mammals include, for example, companion animals (e.g., dogs, cats, and horses), livestock animals (e.g., cattle and swine);

lab animals (e.g., mice and rats); and wild, zoo, and circus animals (e.g., bears, lions, tigers, apes, and monkeys).

C. PHARMACEUTICAL COMPOSITIONS

Some embodiments of this specification are directed to pharmaceutical compositions (or medicaments) comprising a compound of Formula I (or a pharmaceutically acceptable salt thereof), as well as processes for making such pharmaceutical compositions. In general, the pharmaceutical composition comprises a therapeutically effective amount of the compound or salt. Pharmaceutical compositions comprising a compound or salt described in this specification can vary widely. Although it is contemplated that a compound or salt described in this specification could be administered by itself (i.e., without any other active or inactive ingredient), the pharmaceutical composition normally will instead comprise one or more additional active ingredients and/or inert ingredients. The inert ingredients present in the pharmaceutical compositions of this specification are sometimes collectively referred to as "excipients." Methods for making pharmaceutical compositions and the use of excipients are well known in the art. See, e.g., for example, *Remington's Pharmaceutical Sciences*, Mack Publishing Company, Easton, Pa., 15th Edition, 1975.

It is contemplated that compositions comprising a compound of Formula I (or a pharmaceutically acceptable salt thereof) may be formulated for a variety of suitable routes and means of administration, including oral, rectal, nasal, topical, buccal, sublingual, vaginal, inhalation, insufflation, or parenteral administration. In some embodiments, the compound or salt is administered orally. In some embodiments, the compound or salt is administered intravenously. In some embodiments, the compound or salt is administered intramuscularly. In some embodiments, the compound or salt is administered subcutaneously. And, in some embodiments, the compound or salt is administered intraperitoneally, intrathoracially, epidurally, intrathecally, intracerebroventricularly, and injection into the joints. In some embodiments, the compound or salt is administered topically.

It is contemplated that pharmaceutical compositions of this specification may, for example, be in the form of solids, aqueous or oily solutions, suspensions, emulsions, creams, ointments, mists, gels, nasal sprays, suppositories, finely divided powders, and aerosols or nebulisers for inhalation.

In some embodiments, the composition comprises a liquid dosage form that may be administered orally.

In some embodiments, the composition comprises a solid dosage form that may be administered orally.

Solid form compositions may include, for example, powders, tablets, dispersible granules, capsules, cachets, and suppositories. A solid carrier may comprise one or more substances. Such substances are generally inert. A carrier also may act as, for example, a diluent, flavoring agent, solubilizer, lubricant, preservative, stabilizer, suspending agent, binder, or disintegrating agent. It also may act as, for example, an encapsulating material. Examples of often suitable carriers include pharmaceutical grade mannitol, lactose, magnesium carbonate, magnesium stearate, talc, lactose, sugar (e.g., glucose and sucrose), pectin, dextrin, starch, tragacanth, cellulose, cellulose derivatives (e.g., methyl cellulose and sodium carboxymethyl cellulose), sodium saccharin, low-melting wax, and cocoa butter.

In powders, the carrier is typically a finely divided solid, which is in a mixture with the finely divided active component. In tablets, the active component is typically mixed with the carrier having the desirable binding properties in suitable proportions and compacted into the desired shape and size.

For preparing suppository compositions, a low-melting wax (e.g., a mixture of fatty acid glycerides and cocoa butter) is typically first melted, followed by dispersing the active ingredient therein by, for example, stirring. The molten homogeneous mixture is then poured into convenient-sized molds and allowed to cool and solidify. Examples of non-irritating excipients that may be present in suppository compositions include, for example, cocoa butter, glycerinated gelatin, hydrogenated vegetable oils, mixtures of polyethylene glycols of various molecular weights, and fatty acid esters of polyethylene glycol.

Liquid compositions can be prepared by, for example, dissolving or dispersing the compound or a salt of this specification in a carrier, such as, for example, water, water/propylene glycol solutions, saline aqueous dextrose, glycerol, or ethanol. In some embodiments, aqueous solutions for oral administration can be prepared by dissolving a compound or salt of this specification in water with a solubilizer (e.g., a polyethylene glycol). Colorants, flavoring agents, stabilizers, and thickening agents, for example, also may be added. In some embodiments, aqueous suspensions for oral use can be made by dispersing the compound or salt of this specification in a finely divided form in water, together with a viscous material, such as, for example, one or more natural synthetic gums, resins, methyl cellulose, sodium carboxymethyl cellulose, or other suspending agents. If desired, the liquid composition also may contain other non-toxic auxiliary inert ingredients, such as, for example, wetting or emulsifying agents, pH buffering agents and the like, for example, sodium acetate, sorbitan monolaurate, triethanolamine sodium acetate, sorbitan monolaurate, triethanolamine oleate, etc. Such compositions also may contain other ingredients, such as, for example, one or more pharmaceutical adjuvants.

In some embodiments, the concentration of the compound of Formula I (or pharmaceutically acceptable salt thereof) in the pharmaceutical composition is from about 0.05% to about 99% (by weight). In some such embodiments, for example, the concentration is from about 0.05 to about 80%, from about 0.10 to about 70%, or from about 0.10% to about 50% (by weight).

When a compound or salt of this specification is administered as a sole therapy for treating a disorder, a "therapeutically effective amount" is an amount sufficient to reduce or completely alleviate symptoms or other detrimental effects of the condition; cure the condition; reverse, completely stop, or slow the progress of the condition; reduce the risk of the condition getting worse; or delay or reduce the risk of onset of the condition.

In some embodiments of this specification, the pharmaceutical composition is suitable for oral administration in a unit dosage form of, for example, a tablet or capsule containing from about 0.1 mg and about 10 g of the compound of Formula I or pharmaceutically acceptable salt thereof.

In some embodiments, the pharmaceutical composition comprises an amount of a compound of Formula I (or a pharmaceutically acceptable salt thereof) that is therapeutically effective to treat a GR-mediated condition (such as a condition described above) desired to be treated.

In some embodiments, the pharmaceutical composition comprises an amount of a compound of Formula I (or a pharmaceutically acceptable salt thereof) that is therapeutically effective to treat an inflammatory condition.

In some embodiments, the pharmaceutical composition comprises an amount of a compound of Formula I (or a pharmaceutically acceptable salt thereof) that is therapeutically effective to treat a respiratory condition.

In some embodiments, the pharmaceutical composition comprises an amount of a compound of Formula I (or a pharmaceutically acceptable salt thereof) that is therapeutically effective to treat a rheumatic condition.

In some embodiments, the pharmaceutical composition comprises an amount of a compound of Formula I (or a pharmaceutically acceptable salt thereof) that is therapeutically effective to treat rheumatoid arthritis.

In some embodiments, the pharmaceutical composition comprises an amount of a compound of Formula I (or a pharmaceutically acceptable salt thereof) that is therapeutically effective to treat asthma.

In some embodiments, the pharmaceutical composition comprises an amount of a compound of Formula I (or a pharmaceutically acceptable salt thereof) that is therapeutically effective to treat moderate to severe asthma exacerbation.

In some embodiments, the pharmaceutical composition comprises an amount of a compound of Formula I (or a pharmaceutically acceptable salt thereof) that is therapeutically effective to treat COPD.

In some embodiments, the pharmaceutical composition comprises an amount of a compound of Formula I (or a pharmaceutically acceptable salt thereof) that is therapeutically effective to treat moderate to severe COPD exacerbation.

In some embodiments, the pharmaceutical composition comprises an amount of a compound of Formula I (or a pharmaceutically acceptable salt thereof) that is therapeutically effective to treat irritable bowel syndrome.

In some embodiments, the pharmaceutical composition comprises an amount of a compound of Formula I (or a pharmaceutically acceptable salt thereof) that is therapeutically effective to treat a collagen disorder.

In some embodiments, the pharmaceutical composition comprises an amount of a compound of Formula I (or a pharmaceutically acceptable salt thereof) that is therapeutically effective for prophylaxis of kidney transplant rejection.

In some embodiments, the pharmaceutical composition comprises an amount of a compound of Formula I (or a pharmaceutically acceptable salt thereof) that is therapeutically effective to treat sarcoidosis.

In some embodiments, the pharmaceutical composition comprises an amount of a compound of Formula I (or a pharmaceutically acceptable salt thereof) that is therapeutically effective to treat Addison's disease.

In some embodiments, the pharmaceutical composition comprises an amount of a compound of Formula I (or a pharmaceutically acceptable salt thereof) that is therapeutically effective to treat chronic lymphocytic leukemia.

In some embodiments, the pharmaceutical composition comprises an amount of a compound of Formula I (or a pharmaceutically acceptable salt thereof) that is therapeutically effective to treat acute lymphocytic leukemia.

In some embodiments, the pharmaceutical composition comprises an amount of a compound of Formula I (or a pharmaceutically acceptable salt thereof) that is therapeutically effective to treat respiratory distress syndrome.

In some embodiments, the pharmaceutical composition comprises an amount of a compound of Formula I (or a pharmaceutically acceptable salt thereof) that is therapeutically effective to treat nephrotic syndrome.

In some embodiments, the pharmaceutical composition comprises an amount of a compound of Formula I (or a pharmaceutically acceptable salt thereof) that is therapeutically effective to treat a dermatologic disease.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the formulation; and various other factors known to physicians (in the context of human patients), veterinarians (in the context of non-human patients), and others skilled in the art.

It is contemplated that, in some embodiments, the optimum amount of a compound or salt of this specification is at least about 0.01 mg/kg body weight per day, from about 0.01 to about 100 mg/kg body weight per day, or from about 0.01 to about 10 mg/kg body weight per day (e.g., 0.5 mg/kg body weight per day) when administered systemically.

It is contemplated that the pharmaceutical compositions can be in one or more unit dosage forms. Accordingly, the composition may be divided into unit doses containing appropriate quantities of the active component. The unit dosage form can be, for example, a capsule, cachet, or tablet itself, or it can be the appropriate number of any of these in packaged forms. The unit dosage form alternatively can be a packaged preparation in which the package contains discrete quantities of the composition, such as, for example, packeted tablets, capsules, or powders in vials or ampoules. Unit dosage forms may be prepared by, for example, various methods well known in the art of pharmacy.

It is contemplated that a dosage can be given once daily or in divided doses, such as, for example, from 2 to 4 times per day.

D. COMBINATIONS

This specification also is directed to combination therapies or compositions wherein a compound of Formula I (or a pharmaceutically acceptable salt thereof), or a pharmaceutical composition comprising a compound of Formula I (or a pharmaceutically acceptable salt thereof), is administered concurrently (possibly in the same composition) or sequentially with one or more other active agents for the treatment of any of the above-discussed conditions.

In some embodiments in which a combination therapy is used, the amount of the compound or salt of this specification and the amount of the other pharmaceutically active agent(s) are, when combined, therapeutically effective to treat a targeted disorder in the animal patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; reduce the risk of the disorder getting worse; or delay or reduce the risk of onset of the disorder. Typically, such amounts may be determined by one skilled in the art by, for example, starting with the dosage range described in this patent for the compound or salt of this specification and an approved or otherwise published dosage range(s) of the other pharmaceutically active compound(s).

When used in a combination therapy, it is contemplated that the compound or salt of this specification and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

E. KITS

This specification also is directed, in part, to a kit comprising the compound of Formula I or a salt thereof. In some embodiments, the kit further comprises one or more additional components, such as, for example: (a) an apparatus for administering the compound of Formula I or a salt thereof; (b) instructions for administering the compound of Formula I or a salt thereof; (c) an excipient (e.g., a re-suspending agent); or (d) an additional active ingredient, which may be in the same and/or different dosage forms as the compound of Formula I or salt thereof. In some embodiments (particularly when the kit is intended for use in administering the compound of Formula I or salt thereof to an animal patient), the salt is a pharmaceutically acceptable salt.

F. COMPOUND PREPARATION

The following discusses various synthesis schemes for making compounds of Formula I. The schemes are followed by detailed examples that illustrate the preparation of a variety of compounds of Formula I and intermediates for making such compounds. It is expected that one skilled in the art of organic synthesis, after reading the below discussion (alone or in combination with general knowledge in the art), can adapt and apply the methods to make any compound encompassed by Formula I. The general knowledge in the art includes, for example:

A) Conventional procedures for using protective groups and examples of suitable protective groups, which are described in, for example, *Protective Groups in Organic Synthesis*, T. W. Green, P. G. M. Wuts, Wiley-Interscience, New York (1999).
B) References discussing various organic synthesis reactions, include textbooks of organic chemistry, such as, for example, *Advanced Organic Chemistry*, March 4th ed, McGraw Hill (1992); and *Organic Synthesis*, Smith, McGraw Hill, (1994). They also include, for example, R. C. Larock, *Comprehensive Organic Transformations,* 2nd ed., Wiley-VCH: New York (1999); F. A. Carey; R. J. Sundberg, *Advanced Organic Chemistry,* 2nd ed., Plenum Press: New York (1984); L. S. Hegedus, *Transition Metals in the Synthesis of Complex Organic Molecules,* 2nd ed., University Science Books: Mill Valley, C A (1994); L. A. Paquette, Ed., *The Encyclopedia of Reagents for Organic Synthesis,* John Wiley: New York (1994); A. R. Katritzky, O. Meth-Cohn, C W. Rees, Eds., *Comprehensive Organic Functional Group Transformations*, Pergamon Press: Oxford, U K (1995); G. Wilkinson; F. G A. Stone; E. W. Abel, Eds., *Comprehensive Organometallic Chemistry*, Pergamon Press: Oxford, U K (1982); B. M. Trost; I. Fleming, *Comprehensive Organic Synthesis*, Pergamon Press: Oxford, U K (1991); A. R. Katritzky, C W. Rees Eds., *Comprehensive Heterocyclic Chemistry*, Pergamon Press: Oxford, U K (1984); A. R. Katritzky; CW. Rees, E. F. V. Scriven, Eds., *Comprehensive Heterocyclic Chemistry II*, Pergamon Press: Oxford, U K (1996); C. Hansen; P. G. Sammes; J. B. Taylor, Eds., *Comprehensive Medicinal Chemistry*: Pergamon Press: Oxford, UK (1990). In addition, recurring reviews of synthetic methodology and related topics include: *Organic Reactions*, John Wiley: New York; *Organic Syntheses*; John Wiley: New York; *The Total Synthesis of Natural Products*, John Wiley: New York; *The Organic Chemistry of Drug Synthesis*, John Wiley: New York; *Annual Reports in Organic Synthesis*, Academic Press: San Diego Calif.; and *Methoden der Organischen Chemie* (*Houben-Weyl*), Thieme: Stuttgart, Germany.
C) References discussing heterocyclic chemistry include, for example, example, *Heterocyclic Chemistry*, J. A. Joule, K. Mills, G. F. Smith, 3rd ed., Cheapman and Hall, p. 189-225 (1995); and *Heterocyclic Chemistry*, T. L. Gilchrist, $2^{nd}$ ed. Longman Scientific and Technical, p. 248-282 (1992).
D) Databases of synthetic transformations, including Chemical Abstracts, which may be searched using either CAS Online or SciFinder; and Handbuch der Organischen Chemie (Beilstein), which may be searched using, for example, software such as SpotFire.

Scheme 1 below illustrates a general protocol for making compounds described in this specification, using either an Ullman route or an aziridine route.

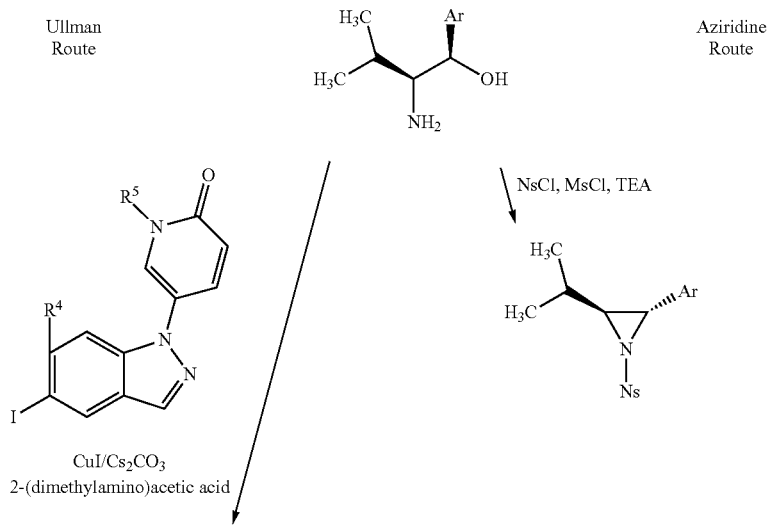

Scheme 1

-continued
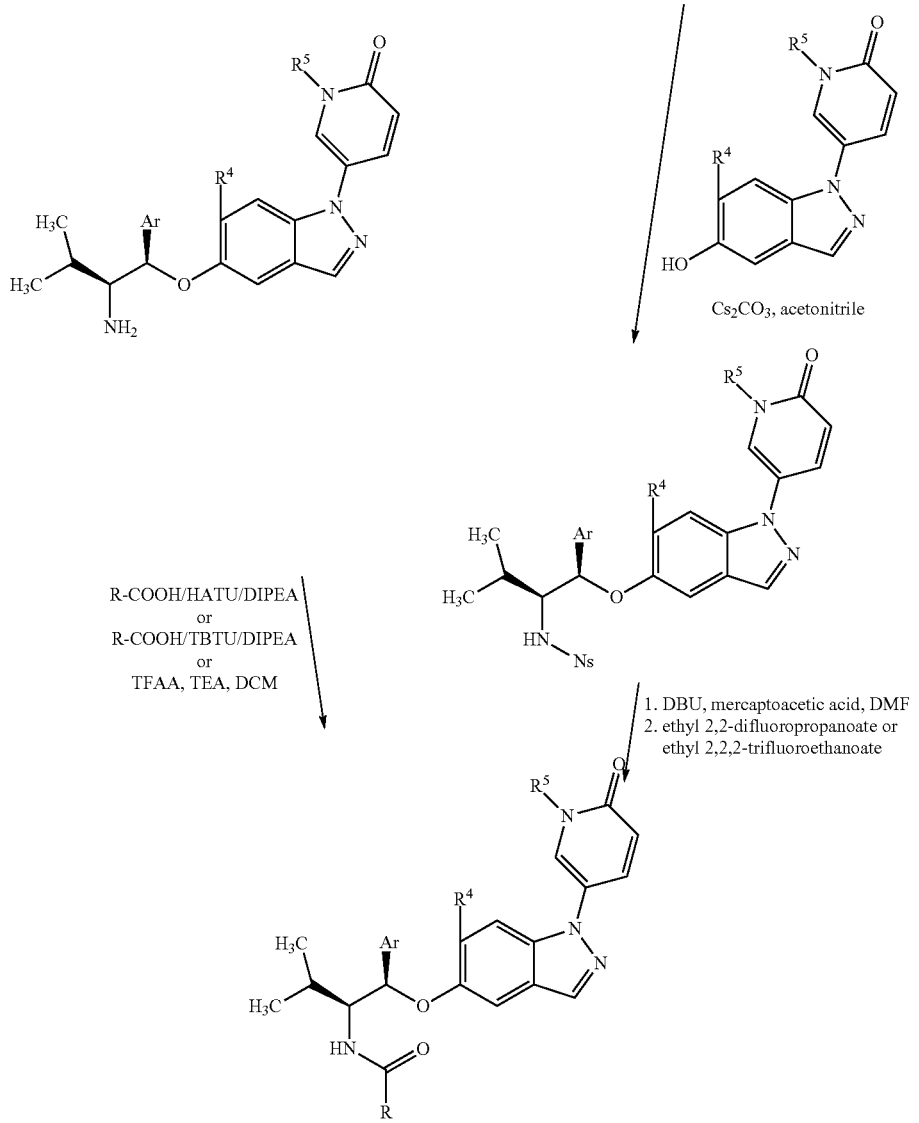
In Scheme 1, Ar is
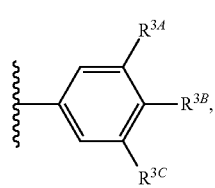
and R is
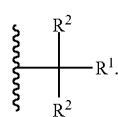
The amino alcohol reagent used in Scheme 1 may be made using the below Scheme 2.
Scheme 2
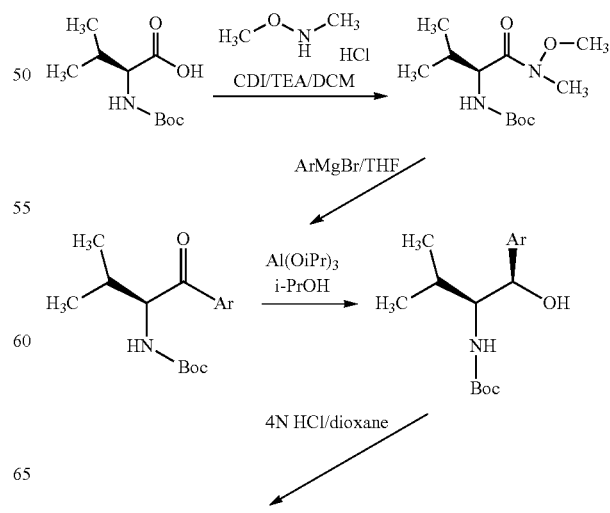

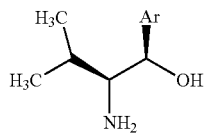

5

The Grignard reagent (ArMgBr) used in Scheme 2 can be obtained commercially, or, if not, can generally be prepared from the corresponding aryl bromide and Mg and/or iPrMgCl using published methods.

The iodo and hydroxy pyridone indazole reagents used in Scheme 1 may be made using the below Scheme 3A or 3B, respectively.

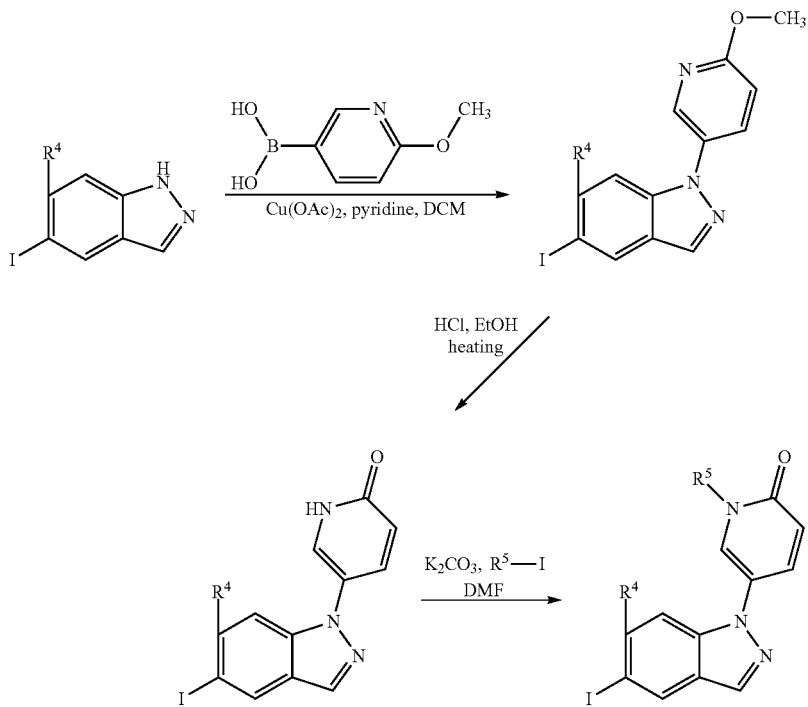

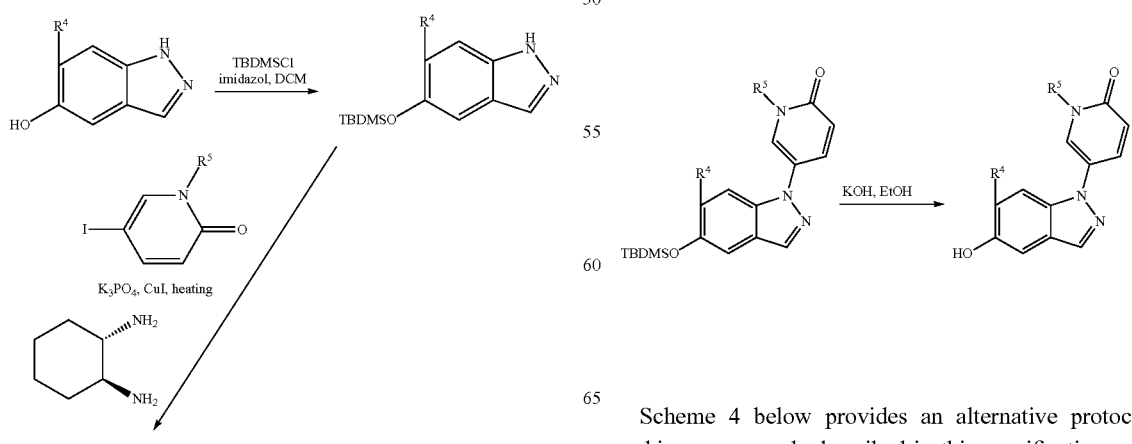

Scheme 4 below provides an alternative protocol for making compounds described in this specification.

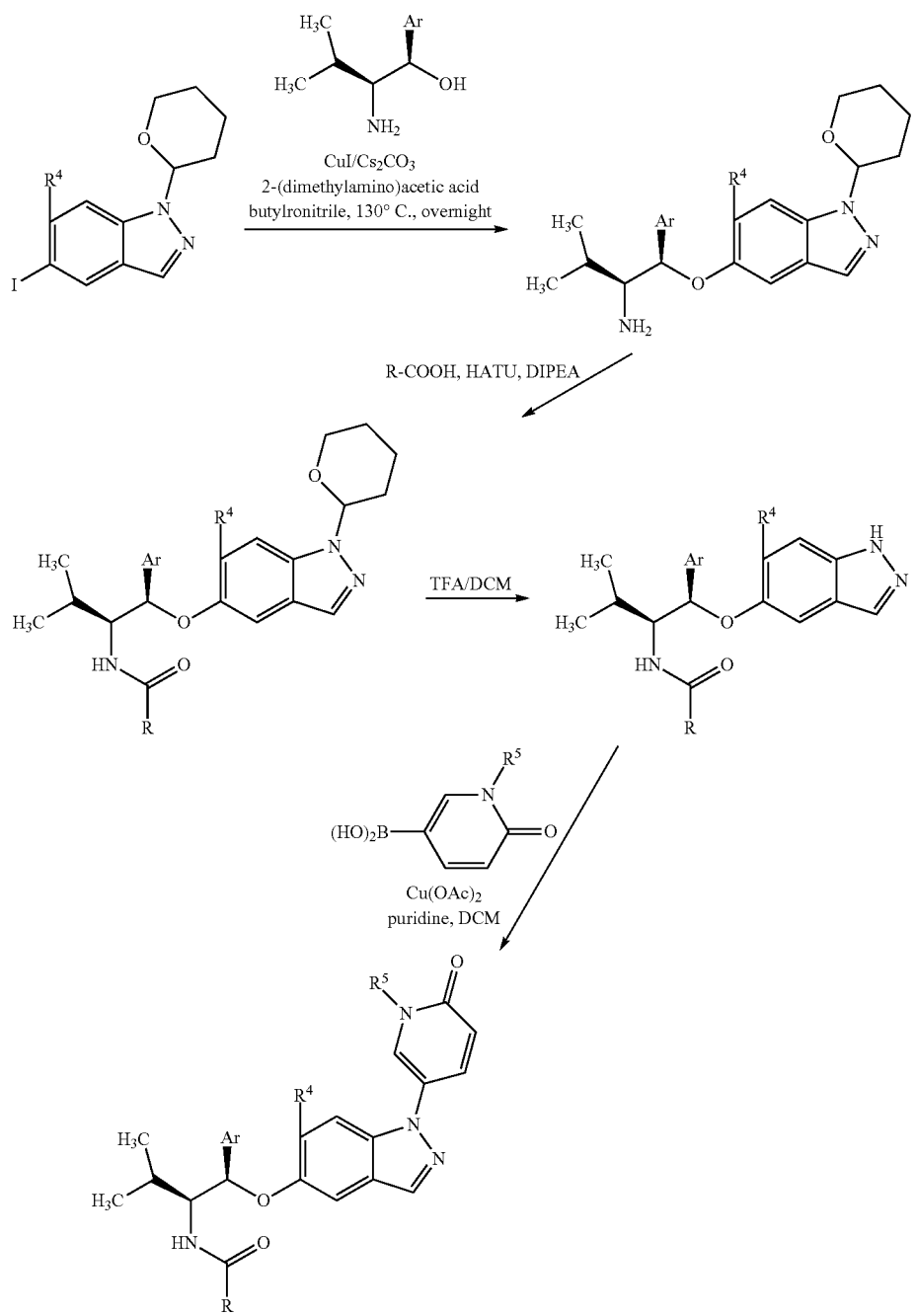

Scheme 4

In general, solvents, temperatures, pressures, and other reaction conditions may be optimized by one of ordinary skill in the art. Starting materials are commercially available, known in the literature, or able to be synthesized by one of ordinary skill in the art using routine organic chemistry methods. And combinatorial techniques can generally be used to prepare compounds when, for example, the intermediates possess groups suitable for such techniques.

G. EXAMPLES

These Examples are provided for illustration purposes only. From the above discussion and these Examples, one skilled in the art can ascertain the essential characteristics of Applicant's invention, and without departing from the spirit and scope thereof, can make various changes and modifications to adapt the specification to various uses and conditions. As a result, this specification is not limited by the illustrative examples below.

Examples 1-23. Compound Synthesis

General Methods.

NMR spectra were recorded on a Bruker Avance, Avance II or Avance III spectrometer at a proton frequency of 300, 400, 500 or 600 MHz. The central peaks of chloroform-δ (H 7.26 ppm), CD₃OD (H 3.30 ppm) or DMSO-d₆ (H 2.49 ppm) were used as internal references.

LC/MS experiments were performed using a Waters Acquity system combined with a Waters Xevo Q-ToF Mass or a Shimadzu 2010EV UPLC system in ESI mode. LC was run in two set ups: 1) BEH C18 column (1.7 μm 2.1×50 mm) in combination with a gradient (2-95% B in 5 min) of aqueous 46 mM ammonium carbonate/ammonia buffer at pH 10 (A) and MeCN (B) at a flow rate of 1.0 mL/min or in combination with a gradient (5-95% B in 2 min) of water and TFA (0.05%) (A) and CH₃CN and TFA (0.05%) at a flow rate of 1.0 mL/min (B).

Optical purity, indicated as enantiomeric excess (% ee), was determined by:

Method A: chiral HPLC using an Agilent 1100 series chromatograph. System equipped with Chiralpak (IB-3, IA-3 or IC-3) 50×4.6 mm; 3 μm. As mobile phase hexane (0.1% triethylamine)/EtOH (85:15) with a flow rate of 1 mL/min was used. The injection volume was 3 μL and compound detection was performed by UV at 254 nm.

Method B: Chiral SFC system equipped with Chiralpak (IC or AD-H) 150×4.6 mm, 3 μm or Chiracel (OD-H, OJ-3, OD-3) or Lux 5u Cellulose-3. As eluent gradients of CO₂ (100 g/min, 120 bar, 40° C.) (A) and 5-40% MeOH/diethylamine (0.1%), EtOH/diethylamine (0.1%), 20% isopropylalcohol or 20% isopropylalcohol/NH₃ 200:1 (B) were applied with a flow rate of 4 mL/min. The injection volume was 0.7 μL or 10 μL and compound detection was performed by UV at 254 nm or 220 nm.

Preparative HPLC was performed with a Waters FractionLynx system with integrated MS detection and equipped with Prep C18 OBD 5 μm 19×150 mm columns from X-Bridge or Sunfire. Alternatively Gilson GX-281 with integrated UV detection was used, equipped with either Kromasil C8 10 μm, 20×250 ID or 50×250 ID mm. As eluent (acidic) gradients of water/MeCN/acetic acid (95/5/0.1) or water/0.05% TFA (A) and MeCN/0.05% TFA (B) or (basic) MeCN or MeOH (A) and 0.03% ammonia in water or 0.03% NH₄HCO₃ (B) were applied.

Preparative SCF was performed with a Waters Prep100 SCF system with integrated MS detection, equipped with Waters Viridis 2-EP or Phenomenex Luna Hilic, 30×250 mm, 5 μm. As eluent gradients of CO₂ (100 g/min, 120 bar, 40° C.) (A) and MeOH/NH₃ (20 mM) or MeOH (5% formic acid) or MeOH (B) were applied.

Unless otherwise stated, starting materials used in the below examples were commercially available or previously described in the literature. All solvents and commercial reagents were of laboratory grade, and were used as received unless otherwise stated.

All temperatures are in degrees Celsius (° C.). In general, unless otherwise stated, operations discussed in the below examples were carried out at room or ambient temperature (18-25° C.); reaction progress was monitored by HPLC, LC-MS or TLC; oven-dried standard laboratory glassware was used and routine manipulations were conducted at ambient temperature under a blanket of N₂; evaporations were performed under reduced pressure using a rotary evaporator; and products were dried under reduced pressure at a suitable temperature.

The names of the compounds exemplified in this patent were generated using ChemDraw Ultra 11.0. This is a chemical-name-generating program that assigns chemical names to drawn structures at the press of a button.

Example 1. Preparation of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl] propanamide

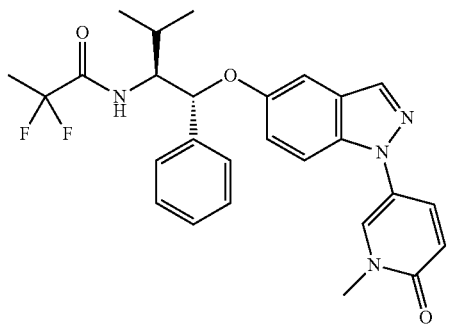 [SMILES: CC(C)[C@H](NC(=O)C(C)(F)F)[C@H](Oc1ccc2c(cnn2-c2ccc(=O)n(C)c2)c1)c1ccccc1]

Step A. Preparation of 5-[5-[(tert-butyldimethylsilyl)oxy]-1H-indazol-1-yl]-1-methyl-1,2-dihydropyridin-2-one

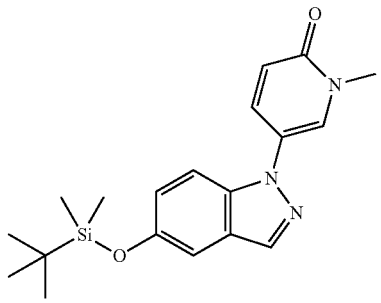 [SMILES: Cn1cc(-n2ncc3cc(O[Si](C)(C)C(C)(C)C)ccc32)ccc1=O]

Into a 2 L 4-necked, round-bottom flask, purged and maintained with an inert atmosphere of N₂, was placed a solution of 5-[(tert-butyldimethylsilyl)oxy]-1H-indazole (805 g, 3.2 mol) in toluene (8 L), 5-iodo-1-methyl-1,2-dihydropyridin-2-one (800 g, 3.4 mol) and K₃PO₄ (1.2 kg, 5.8 mol). Cyclohexane-1,2-diamine (63 g, 0.5 mol) was added followed by the addition of CuI (1.3 g, 6.8 mmol) in several batches. The resulting solution was stirred overnight at 102° C. The resulting mixture was concentrated under vacuum to yield 3.0 kg of the title compound as a crude black solid. LC/MS: m/z 356 [M+H]⁺.

Step B. Preparation of 5-(5-hydroxy-1H-indazol-1-yl)-1-methylpyridin-2(1H)-one

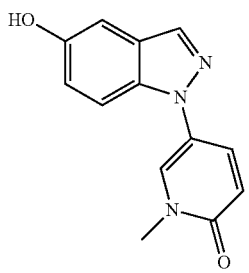 [SMILES: Cn1cc(-n2ncc3cc(O)ccc32)ccc1=O]

Into a 2 L 4-necked, round-bottom flask was placed 5-[5-[(tert-butyldimethylsilyl)oxy]-1H-indazol-1-yl]-1-methyl-1,2-dihydropyridin-2-one (3.0 kg, crude) and a solution of HCl (2 L, 24 mol, 36%) in water (2 L) and MeOH (5 L). The resulting solution was stirred for 1 hr at 40° C. and then evaporated to dryness. The resulting solid was washed with water (4×5 L) and ethyl acetate (2×0.5 L) to afford 480 g (61%, two steps) of the title product as a brown solid. LC/MS: m/z 242 [M+H]+. ¹HNMR (300 MHz, DMSO-d6): δ 3.52 (3H, s), 6.61 (1H, m), 7.06 (2H, m), 7.54 (1H, m), 7.77 (1H, m), 8.19 (2H, m) 9.35 (1H,$).

Step C. Preparation of tert-butyl((1R,2S)-1-hydroxy-3-methyl-1-phenylbutan-2-yl)carbamate

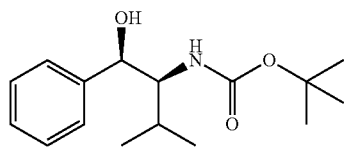 [SMILES: CC(C)[C@H](NC(=O)OC(C)(C)C)[C@H](O)c1ccccc1]

(S)-tert-butyl 3-methyl-1-oxo-1-phenylbutan-2-ylcarbamate (1.0 kg, 3.5 mol) was dissolved in toluene (4 L). Afterward, 2-propanol (2 L) was added, followed by triisopropoxyaluminum (0.145 L, 0.73 mol). The reaction mixture was heated at 54-58° C. for 1 hr under reduced pressure (300-350 mbar) to start azeothropic distillation. After the collection of 0.75 L condensate, 2-propanol (2 L) was added, and the reaction mixture was stirred overnight at reduced pressure to afford 4 L condensate in total. Toluene (3 L) was added at 20° C., followed by 2M HCl (2 L) over 15 min to keep the temperature below 28° C. The layers were separated (pH of aqueous phase 0-1) and the organic layer was washed successively with water (3 L), 4% NaHCO₃ (2 L) and water (250 mL). The volume of the organic layer was reduced from 6 L at 50° C. and 70 mbar to 2.5 L. The resulting mixture was heated to 50° C. and heptane (6.5 L) was added at 47-53° C. to maintain the material in solution. The temperature of the mixture was slowly decreased to 20° C., seeded with the crystals of the title compound at 37° C. (seed crystals were prepared in an earlier batch made by the same method and then evaporating the reaction mixture to dryness, slurring the residue in heptane, and isolating the crystals by filtration), and allowed to stand overnight. The product was filtered off, washed with heptane (2×1 L) and dried under vacuum to afford 806 g (81%) of the title compound as a white solid. ¹HNMR (500 MHz, DMSO-d6): δ 0.81 (dd, 6H), 1.16 (s, 8H), 2.19 (m, 1H), 3.51 (m, 1H), 4.32 (d, 1H), 5.26 (s, 1H), 6.30 (d, 1H), 7.13-7.2 (m, 1H), 7.24 (t, 2H), 7.3-7.36 (m, 3H).

Step D. Preparation of (1R,2S)-2-amino-3-methyl-1-phenylbutan-1-ol hydrochloride salt

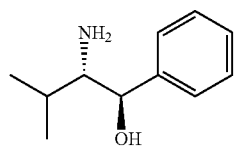

To a solution of HCl in propan-2-ol (5-6 N, 3.1 L, 16 mol) at 20° C. was added tert-butyl((1R,2S)-1-hydroxy-3-methyl-1-phenylbutan-2-yl)carbamate (605 g, 2.2 mol) in portions over 70 min followed by the addition of MTBE (2 L) over 30 min. The reaction mixture was cooled to 5° C. and stirred for 18 hr. The product was isolated by filtration and dried to afford 286 g of the title compound as an HCl salt (61% yield). The mother liquor was concentrated to 300 mL. MTBE (300 mL) was then added, and the resulting precipitation was isolated by filtration to afford additional 84 g of the title compound as a HCl salt (18% yield). Total 370 g (79%). ¹HNMR (400 MHz, DMSO-d6): δ 0.91 (dd, 6H), 1.61-1.81 (m, 1H), 3.11 (s, 1H), 4.99 (s, 1H), 6.08 (d, 1H), 7.30 (t, 1H), 7.40 (dt, 4H), 7.97 (s, 2H).

Step E. Preparation of (2S,3S)-2-isopropyl-1-(4-nitrophenylsulfonyl)-3-phenylaziridine

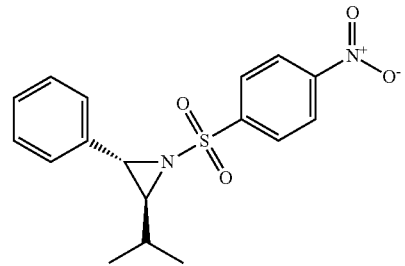 [SMILES: CC(C)[C@H]1[C@H](c2ccccc2)N1S(=O)(=O)c1ccc([N+](=O)[O-])cc1]

(1R,2S)-2-Amino-3-methyl-1-phenylbutan-1-ol hydrochloride (430 g, 2.0 mol) was mixed with DCM (5 L) at 20° C. 4-Nitrobenzenesulfonyl chloride (460 g, 2.0 mol) was then added over 5 min. Afterward, the mixture was cooled to −27° C. Triethylamine (1.0 kg, 10 mol) was slowly added while maintaining the temperature at −18° C. The reaction mixture was cooled to −30° C., and methanesulfonyl chloride (460 g, 4.0 mol) was added slowly while maintaining the temperature at −25° C. The reaction mixture was then stirred at 0° C. for 16 hr before adding triethylamine (40 mL, 0.3 mol; 20 mL, 0.14 mol and 10 mL, 0.074 mol) w at 0° C. in portions over 4 hr. Water (5 L) was subsequently added at 20° C., and the resulting layers were separated. The organic layer was washed with water (5 L) and the volume reduced to 1 L under vacuum. MTBE (1.5 L) was added, and the mixture was stirred on a rotavap at 20° C. over night and filtered to afford 500 g (70%) of the title product as a solid. ¹HNMR (400 MHz, CDCl₃): δ 1.12 (d, 3H), 1.25 (d, 3H), 2.23 (ddt, 1H), 2.89 (dd, 1H), 3.84 (d, 1H), 7.08-7.2 (m, 1H), 7.22-7.35 (m, 4H), 8.01-8.13 (m, 2H), 8.22-8.35 (m, 2H)

Step F. Preparation of N-((1R,2S)-3-methyl-1-(1-(1-methyl-6-oxo-1,6-dihydropyridin-3-yl)-1H-indazol-5-yloxy)-1-phenylbutan-2-yl)-4-nitrobenzenesulfonamide

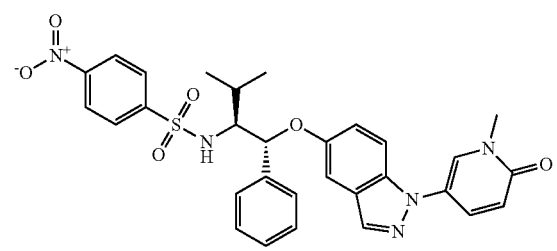

(2S,3S)-2-Isopropyl-1-(4-nitrophenylsulfonyl)-3-phenylaziridine (490 g, 1.3 mol) was mixed with 5-(5-hydroxy-1H-indazol-1-yl)-1-methylpyridin-2(1H)-one (360 g, 1.4 mol) in acetonitrile (5 L) at 20° C. Cesium carbonate (850 g, 2.6 mol) was added in portions over 5 min. The reaction mixture was then stirred at 50° C. overnight. Water (5 L) was added at 20° C., and the resulting mixture was extracted with 2-methyltetrahydrofuran (5 L and 2.5 L). The combined organic layer was washed successively with 0.5 M HCl (5 L), water (3×5 L) and brine (5 L). The remaining organic layer was concentrated to a thick oil, and then MTBE (2 L) was added. The resulting precipitate was filtered to afford 780 g (purity 71% w/w) of the crude title product as a yellow solid, which was used in the next step without further purification. $^1$HNMR (400 MHz, DMSO-d6): δ 0.93 (dd, 6H), 2.01-2.19 (m, 1H), 3.50 (s, 3H), 3.74 (s, 1H), 5.00 (d, 1H), 6.54 (d, 1H), 6.78 (d, 1H), 6.95-7.15 (m, 4H), 7.23 (d, 2H), 7.49 (d, 1H), 7.69 (dd, 1H), 7.74 (d, 2H), 8.00 (s, 1H), 8.08 (d, 2H), 8.13 (d, 2H).

Step G. Preparation of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide

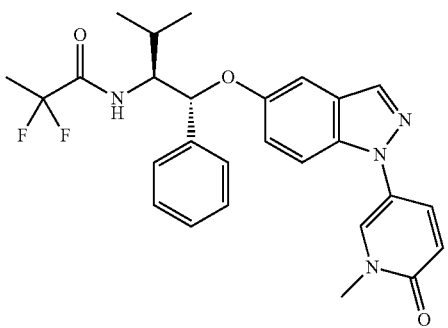 [SMILES: CC(C)[C@H](NC(=O)C(C)(F)F)[C@H](Oc1ccc2c(cnn2-c2ccc(=O)n(C)c2)c1)c1ccccc1]

N-((1R,2S)-3-Methyl-1-(1-(1-methyl-6-oxo-1,6-dihydropyridin-3-yl)-1H-indazol-5-yloxy)-1-phenylbutan-2-yl)-4-nitrobenzenesulfonamide (780 g, 71% w/w) was mixed with DMF (4 L). DBU (860 g, 5.6 mol) was then added at 20° C. over 10 min. 2-Mercaptoacetic acid (170 g, 1.9 mol) was added slowly over 30 min, keeping the temperature at 20° C. After 1 hr, ethyl 2,2-difluoropropanoate (635 g, 4.60 mol) was added over 10 min at 20° C. The reaction mixture was stirred for 18 hr. Subsequently, additional ethyl 2,2-difluoropropanoate (254 g, 1.8 mol) was added, and the reaction mixture was stirred for an additional 4 hr at 20° C. Water (5 L) was then slowly added over 40 min, maintaining the temperature at 20° C. The water layer was extracted with isopropyl acetate (4 L and 2×2 L). The combined organic layer was washed with 0.5M HCl (4 L) and brine (2 L). The organic layer was then combined with the organic layer from a parallel reaction starting from 96 g of N-((1R,2S)-3-methyl-1-((1-(1-methyl-6-oxo-1,6-dihydropyridin-3-yl)-1H-indazol-5-yl)oxy)-1-phenylbutan-2-yl)-4-nitrobenzenesulfonamide, and concentrated to approximate 1.5 L. The resulting brown solution was filtered. The filter was washed twice with isopropyl acetate (2×0.5 L). The filtrate was evaporated until a solid formed. The solid was then co evaporated with 99.5% ethanol (1 L), affording 493 g (77%, two steps) of an amorphous solid.

The solid (464 g, 0.94 mol) was dissolved in ethanol/water 2:1 (3.7 L) at 50° C. The reaction mixture was then seeded with crystals 0 of the title compound (0.5 g) at 47° C., and a slight opaque mixture was formed. The mixture was held at that temperature for 1 hr. Afterward, the temperature was decreased to 20° C. over 7 hr, and kept at 20° C. for 40 hr. The solid was filtrated off, washed with cold (5° C.) ethanol/water 1:2 (0.8 L), and dried in vacuum at 37° C. overnight to afford 356 g (0.70 mol, 74%, 99.9% ee) of the title compound as a monohydrate. LC/MS: m/z 495 [M+H]$^+$. $^1$HNMR (600 MHz, DMSO-d6) δ 0.91 (dd, 6H), 1.38 (t, 3H), 2.42 (m, 1H), 3.50 (s, 3H), 4.21 (m, 1H), 5.29 (d, 1H), 6.53 (d, 1H), 7.09 (d, 1H), 7.13 (dd, 1H), 7.22 (t, 1H), 7.29 (t, 2H), 7.47 (d, 2H), 7.56 (d, 1H), 7.70 (dd, 1H), 8.13 (d, 1H), 8.16 (d, 1H), 8.27 (d, 1H).

The seed crystals may be prepared from amorphous compound prepared according to Example 2 using 2,2-difluoropropanoic acid, followed by purification on HPLC. The compound (401 mg) was weighed into a glass vial. Ethanol (0.4 mL) was added, and the vial was shaken and heated to 40° C. to afford a clear, slightly yellow solution. Ethanol/Water (0.4 mL, 50/50% vol/vol) was added. Crystallization started to occur within 5 min, and, after 10 min, a white thick suspension formed. The crystals were collected by filtration.

Example 2 Preparation of 2,2,2-trifluoro-N-[(1R,2S)-3-methyl-1-{[1-(1-methyl-6-oxo-1,6-dihydropyridin-3-yl)-1H-indazol-5-yl]oxy}-1-phenylbutan-2-yl]acetamide

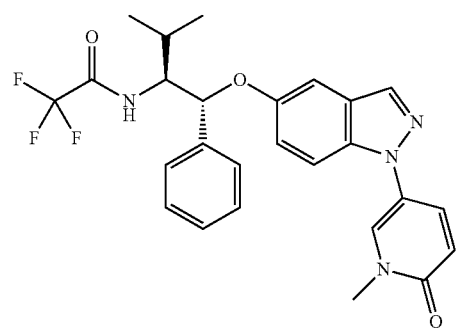 [SMILES: CC(C)[C@H](NC(=O)C(F)(F)F)[C@H](Oc1ccc2c(cnn2-c2ccc(=O)n(C)c2)c1)c1ccccc1]

Step A. Preparation of 5-iodo-1-(6-methoxypyridin-3-yl)-1H-indazole

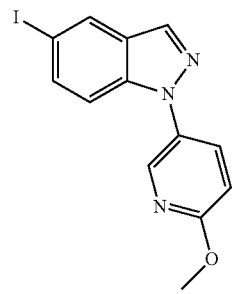 [SMILES: COc1ccc(-n2ncc3cc(I)ccc32)cn1]

A mixture of copper (II) acetate (82 mg, 0.45 mmol), 5-iodo-1H-indazole (100 mg, 0.41 mmol), 6-methoxypyridin-3-yl boronic acid (91 mg, 0.59 mmol) and pyridine (133 µL, 1.64 mmol) in DCM (3.2 mL) at room temperature open to the air (vial not sealed) was stirred overnight. The reaction mixture was filtered and evaporated under reduced pressure. The residue was purified by chromatography eluting with ethyl acetate/petroleum ether (1:8) to afford 114 mg (86%) of the title compound as yellow solid. LCMS: m/z 352 [M+H]$^+$. $^1$HNMR (300 MHz; DMSO-d6): δ 3.94 (3H, s), 7.04 (1H, d), 7.59 (1H, d), 7.73 (1H, d), 8.06 (1H, dd), 8.32-8.34 (2H, m), 8.55 (1H, d).

Step B. Preparation of 5-(5-iodo-1H-indazol-1-yl)pyridin-2(1H)-one

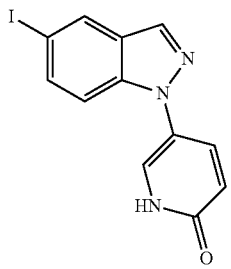 [SMILES: O=c1ccc(-n2ncc3cc(I)ccc32)c[nH]1]

To a stirred mixture of 5-iodo-1-(6-methoxypyridin-3-yl)-1H-indazole (6.4 g, 18 mmol) in 2M HCl (31 mL, 62 mmol) and ethanol (51 mL) was added concentrated HCl (15 mL, 180 mmol). The resulting solution was refluxed for 24 hr. The mixture was subsequently cooled, and the resulting precipitate was filtered off, washed with water and dried in vacuum at 40° C. for 3.5 hr to afford the title product 5.9 g (95%) of as white solid. LCMS: m/z 338 [M+H]$^+$. $^1$HNMR (300 MHz; DMSO-d6): δ 6.48 (1H, d), 7.42 (2H, d), 7.60-7.75 (2H, m), 7.81 (1H, d), 8.23 (1H, d), 11.92 (1H, br).

Step C. Preparation of 5-(5-iodo-1H-indazol-1-yl)-1-methylpyridin-2(1H)-one

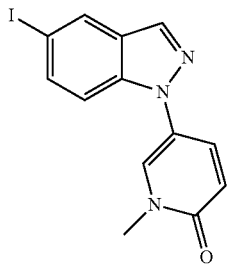 [SMILES: Cn1cc(-n2ncc3cc(I)ccc32)ccc1=O]

To a mixture of 5-(5-iodo-1H-indazol-1-yl)pyridin-2(1H)-one (1.6 g, 4.7 mmol, 1.0 equiv) and K$_2$CO$_3$ (2 g, 14 mmol, 3.0 equiv) in DMF (50 mL) was added MeI (0.9 mL, 14 mmol, 3.0 equiv) at room temperature under N$_2$. The mixture was stirred for 4 hr at room temperature and then partitioned between DCM and water. The organic layer was separated, washed with water and purified by column chromatography eluting with MeOH/DCM (1/20) to afford the crude title product 1.7 g as a white solid. LCMS: m/z 352 [M+H]$^+$. $^1$HNMR (300 MHz, CDCl$_3$): δ 3.64 (3H, s), 6.72 (1H, d), 7.23 (1H, d), 7.65-7.70 (3H, m), 8.05 (1H, s), 8.15 (1H, s).

Step D. Preparation of 5-(5-((1R,2S)-2-amino-3-methyl-1-phenylbutoxy)-1H-indazol-1-yl)-1-methylpyridin-2(1H)-one

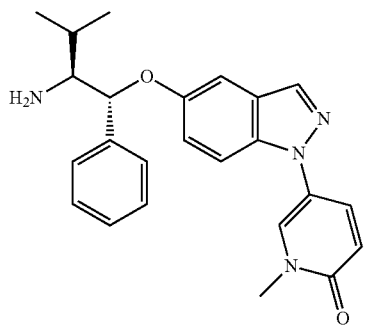 [SMILES: CC(C)[C@H](N)[C@H](Oc1ccc2c(cnn2-c2ccc(=O)n(C)c2)c1)c1ccccc1]

A mixture of (1R,2S)-2-amino-3-methyl-1-phenylbutan-1-ol as the free base (Example 1/step D) (0.96 g, 5.3 mmol), 5-(5-iodo-1H-indazol-1-yl)-1-methylpyridin-2(1H)-one (1.9 g, 5.4 mmol), copper(I) iodide (0.51 g, 2.7 mmol), 2-(dimethylamino)acetic acid (0.55 g, 5.3 mmol) and cesium carbonate (5.2 g, 16 mmol) in butyronitrile (30 mL) was stirred at 130° C. for 20 hr. Afterward, the reaction mixture was cooled to room temperature and concentrated, and the residue was purified by silica gel column chromatography eluting with DCM/MeOH (20/1) to afford 0.5 g (23%) of the crude title compound. LC/MS: m/z 403 [M+H]$^+$ Step E. Preparation of 2,2,2-trifluoro-N-[(1R,2S)-3-methyl-1-{[1-(1-methyl-6-oxo-1,6-dihydropyridin-3-yl)-1H-indazol-5-yl]oxy}-1-phenylbutan-2-yl]acetamide

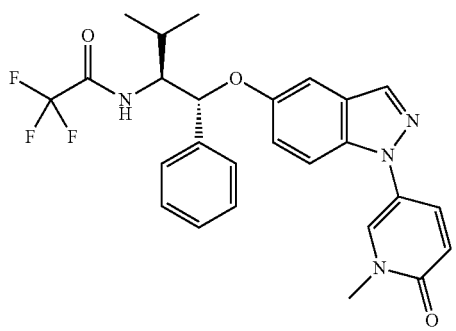 [SMILES: CC(C)[C@H](NC(=O)C(F)(F)F)[C@H](Oc1ccc2c(cnn2-c2ccc(=O)n(C)c2)c1)c1ccccc1]

A mixture of 5-(5-((1R,2S)-2-amino-3-methyl-1-phenylbutoxy)-1H-indazol-1-yl)-1-methylpyridin-2(1H)-one (850 mg, 1.8 mmol), TFA (250 mg, 2.2 mmol), HATU (1021 mg, 2.7 mmol) and DIPEA (0.94 mL, 5.4 mmol) in DMF (7 mL) was stirred at room temperature for several hours. Afterward, the reaction mixture was poured into water and extracted with DCM (3×20 mL), dried over Na$_2$SO$_4$ and concentrated. The residue was purified on silica gel by column chromatography eluting with DCM/MeOH (10/1) to afford 500 mg (56%) of the title compound as a white solid. LCMS m/z 499 [M+H]$^+$. $^1$HNMR (300 MHz, CDCl$_3$): δ 0.90-1.05 (6H, m), 1.98-2.08 (1H, m), 3.59 (3H, s), 4.38-4.45 (1H, m), 5.33 (1H, d), 6.19 (1H, d), 6.68 (1H, d), 6.93 (1H, d), 7.11 (1H, dd), 7.30-7.45 (6H, m), 7.58-7.68 (2H, m), 7.92 (1H, s).

Example 3. N-[(1R,2S)-1-(3,5-difluorophenyl)-3-methyl-1-{[1-(1-methyl-6-oxo-1,6-dihydropyridin-3-yl)-1H-indazol-5-yl]oxy}butan-2-yl]-2,2-difluoropropanamide

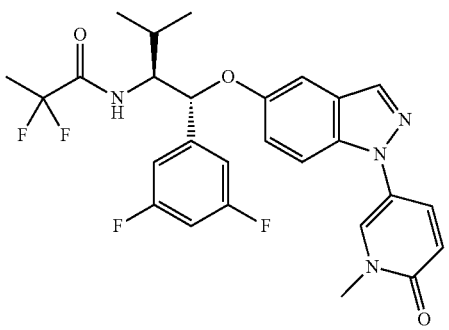 [SMILES: CC(C)[C@H](NC(=O)C(C)(F)F)[C@H](Oc1ccc2c(cnn2-c2ccc(=O)n(C)c2)c1)c1cc(F)cc(F)c1]

The title compound was prepared following the procedure for Example 2 using 2,2-difluoropropanoic acid to afford 58 mg (40%) of the product. The Grignard reagent in Scheme 2 was generated according to the following procedure: Magnesium (2.0 g, 83 mmol), 3,5-difluorobromobenzene (1.45 g, 7.6 mmol) and iodine (12, cat.) were mixed in THF (2 mL). The reaction mixture was heated to 60° C. After the red color disappeared, additional 3,5-difluorobromobenzene (13 g, 67 mmol) in THF (150 ml) was added dropwise, keeping the temperature at 50° C. The reaction mixture was then refluxed for 3 hr, and then cooled to room temperature. The resulting solution (~0.5 M in THF) was used without purification. LC/MS: m/z 531 [M+H]+. 1H NMR (300 MHz; CDCl3): δ 0.99-1.05 (m, 6H), 1.72 (t, 3H), 2.09-2.20 (m, 1H), 3.66 (s, 3H), 4.30-4.37 (m, 1H), 5.19 (d, 1H), 6.33 (d, 1H), 6.71-6.78 (m, 2H), 6.91-6.99 (m, 3H), 7.11 (d, 1H), 7.37 (d, 1H), 7.60 (br, 2H), 7.97 (s, 1H).

Example 4. Preparation of N-[(1R,2S)-1-(3,5-difluorophenyl)-3-methyl-1-{[1-(1-methyl-6-oxo-1,6-dihydropyridin-3-yl)-1H-indazol-5-yl]oxy}butan-2-yl]-2,2-difluoropropanamide

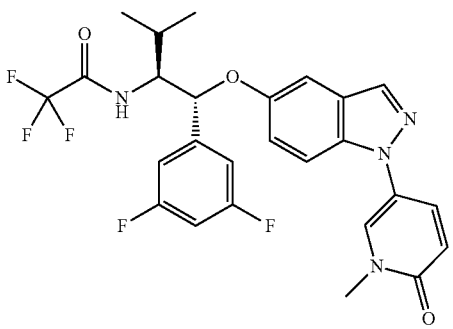 [SMILES: CC(C)[C@H](NC(=O)C(F)(F)F)[C@H](Oc1ccc2c(cnn2-c2ccc(=O)n(C)c2)c1)c1cc(F)cc(F)c1]

The title compound was prepared following the procedure for Example 2 using TFA to afford 40 mg (33%) product. The Grignard reagent in Scheme 2 was generated according to the following procedure: Magnesium (2.0 g, 83 mmol), 3,5-difluorobromobenzene (1.45 g, 7.6 mmol) and iodine (12, cat.) were mixed in THF (2 mL). The resulting mixture was heated to 60° C. After the red color disappeared, additional 3,5-difluorobromobenzene (13 g, 67 mmol) in THF (150 ml) was added dropwise, keeping the temperature at 50° C. The reaction mixture was refluxed for 3 hr, and then cooled to room temperature. The solution (~0.5 M in THF) was used without purification. LC/MS: m/z 535 [M+H]+. 1H NMR (300 MHz; CDCl3): δ1.01-1.07 (m, 6H), 2.07-2.18 (m, 1H), 3.63 (s, 3H), 4.34-4.40 (m, 1H), 5.26 (d, 1H), 6.27 (d, 1H), 6.73-6.81 (m, 2H), 6.91-6.98 (m, 3H), 7.10 (d, 1H), 7.35 (d, 1H), 7.60-7.65 (m, 2H), 7.97 (s, 1H).

Example 5. Preparation of N-[(1R,2S)-1-(3-chlorophenyl)-3-methyl-1-{[1-(1-methyl-6-oxo-1,6-dihydropyridin-3-yl)-1H-indazol-5-yl]oxy}butan-2-yl]-2,2-difluoropropanamide

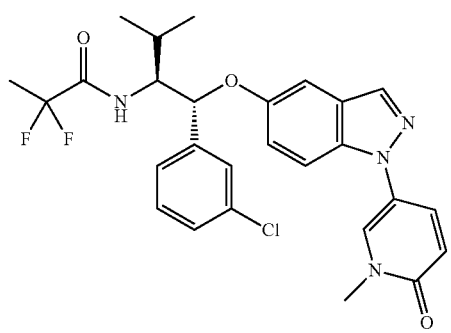 [SMILES: CC(C)[C@H](NC(=O)C(C)(F)F)[C@H](Oc1ccc2c(cnn2-c2ccc(=O)n(C)c2)c1)c1cccc(Cl)c1]

The title compound was prepared following the procedure for Example 2 using 2,2-difluoropropanoic acid to afford 62 mg (47%) product. LC/MS: m/z 529/531 3:1 [M+H]+. 1HNMR (300 MHz; CDCl3): δ 0.99-1.05 (m, 6H), 1.69 (t, 3H), 2.11-2.17 (m, 1H), 3.66 (s, 3H), 4.32-4.39 (m, 1H), 5.19 (d, 1H), 6.30 (d, 1H), 6.73 (d, 1H), 6.94 (d, 1H), 7.14 (d, 1H), 7.28-7.39 (m, 5H), 7.62-7.66 (m, 2H), 7.95 (s, 1H).

Example 6. Preparation of N-[(1R,2S)-1-(3-chlorophenyl)-3-methyl-1-{[1-(1-methyl-6-oxo-1,6-dihydropyridin-3-yl)-1H-indazol-5-yl]oxy}butan-2-yl]-2,2,2-trifluoroacetamide

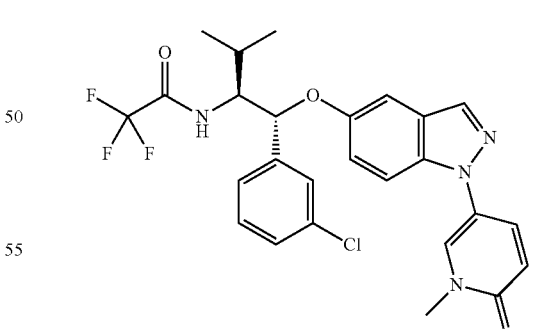

The title compound was prepared following the procedure for Example 2 using TFA to afford 55 mg (68%) product. LC/MS: m/z 533/535 3:1 [M+H]+. 1HNMR (300 MHz; CDCl3): δ1.04 (t, 6H), 2.03-2.07 (m, 1H), 3.64 (s, 3H), 4.35-4.41 (m, 1H), 5.27 (d, 1H), 6.23 (d, 1H), 6.79 (d, 1H), 6.94 (d, 1H), 7.10 (d, 1H), 7.28-7.39 (m, 5H), 7.60-7.69 (m, 2H), 7.96 (s, 1H).

Example 7. Preparation of N-[(1R,2S)-1-(4-chlorophenyl)-3-methyl-1-{[1-(1-methyl-6-oxo-1,6-dihydropyridin-3-yl)-1H-indazol-5-yl]oxy}butan-2-yl]-2,2-difluoropropanamide

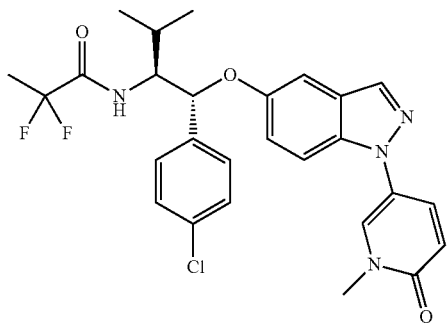 [SMILES: CC(C)[C@H](NC(=O)C(C)(F)F)[C@H](Oc1ccc2c(cnn2-c2ccc(=O)n(C)c2)c1)c1ccc(Cl)cc1]

The title compound was prepared following the procedure for Example 2 using 2,2-difluoropropanoic acid to afford 60 mg (33%) product. LCMS: m/z 529/531 3:1 [M+H]$^+$. $^1$HNMR (300 MHz, CDCl$_3$): δ 1.01 (m, 6H), 1.70 (t, 3H), 2.11 (m, 1H), 3.62 (s, 3H), 4.35 (m, 1H), 5.22 (d, 1H), 6.30 (d, 1H), 6.70 (m, 1H), 6.91 (s, 1H), 7.10 (m, 1H), 7.35 (m, 5H), 7.63 (m, 2H), 7.95 (s, 1H).

Example 8. Preparation of N-[(1R,2S)-1-(3,5-dichlorophenyl)-3-methyl-1-{[1-(1-methyl-6-oxo-1,6-dihydropyridin-3-yl)-1H-indazol-5-yl]oxy}butan-2-yl]-2,2-difluoropropanamide

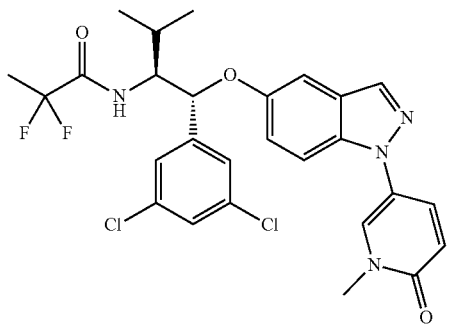 [SMILES: CC(C)[C@H](NC(=O)C(C)(F)F)[C@H](Oc1ccc2c(cnn2-c2ccc(=O)n(C)c2)c1)c1cc(Cl)cc(Cl)c1]

The title compound was prepared following the procedure for Example 2 using 2,2-difluoropropanoic acid to afford 50 mg (28%) product. LCMS: m/z 563 [M+H]$^+$. $^1$HNMR (300 MHz, CD$_3$OD) δ 0.89-0.92 (m, 6H), 1.46-1.59 (t, 3H), 2.39 (m, 1H), 3.33 (s, 3H), 4.10-4.17 (m, 1H), 5.30-5.33 (d, 1H), 6.53-6.56 (d, 1H), 7.13-7.19 (m, 2H), 7.50-7.74 (m, 5H), 8.18-8.19 (m, 2H), 8.34-8.37 (m, 1H).

Example 9. Preparation of 2,2-difluoro-N-{(1R,2S)-3-methyl-1-{[1-(1-methyl-6-oxo-1,6-dihydropyridin-3-yl)-1H-indazol-5-yl]oxy}-1-[4-(trifluoromethoxy)phenyl]butan-2-yl}propanamide

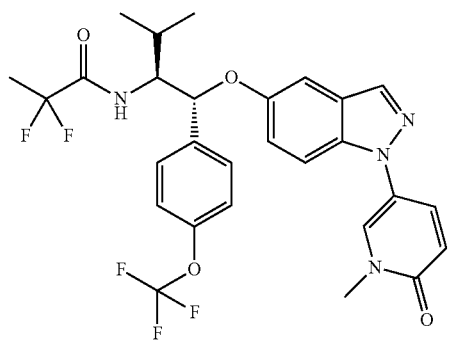 [SMILES: CC(C)[C@H](NC(=O)C(C)(F)F)[C@H](Oc1ccc2c(cnn2-c2ccc(=O)n(C)c2)c1)c1ccc(OC(F)(F)F)cc1]

The title compound was prepared following the procedure for Example 2 using 2,2-difluoropropanoic acid to afford 52 mg (26%) product. The Grignard reagent in Scheme 2 was generated according to the following procedure: Magnesium (0.29 g, 12 mmol) and iodine (12, cat.) were added into a reaction flask, followed by dropwise addition of a solution of 1-bromo-4-(trifluoromethoxy)benzene (2.4 g, 10 mmol) in THF (10 mL). The reaction mixture was refluxed for 1 hr, and then cooled to room temperature. The resulting solution (~1M in THF) was be used without purification. LCMS: m/z 579 [M+H]$^+$. $^1$H-NMR (300 MHz; CD$_3$OD): δ 1.02-1.05 (6H, m), 1.31-1.50 (3H, t), 2.46-2.53 (1H, m), 3.66 (3H, s), 4.36-4.41 (1H, m), 5.31-5.34 (1H, d), 6.70-6.73 (1H, d), 7.17-7.25 (4H, m), 7.51-7.61 (3H, m), 7.81-7.86 (1H, m), 8.06-8.08 (2H, m).

Example 10. Preparation of 2,2-difluoro-N-{(1R,2S)-3-methyl-1-{[1-(1-methyl-6-oxo-1,6-dihydropyridin-3-yl)-1H-indazol-5-yl]oxy}-1-[4-(trifluoromethyl)phenyl]butan-2-yl}propanamide

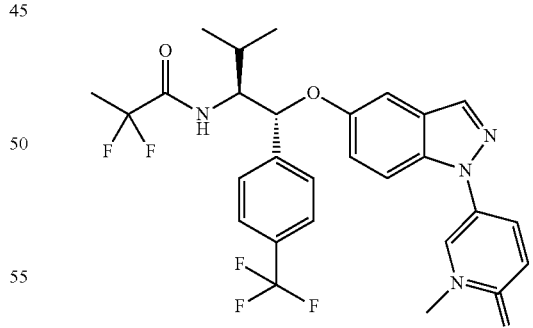

The title compound was prepared following the procedure for Example 2 using 2,2-difluoropropanoic acid to afford 65 mg (26%) product. LCMS: m/z 563 [M+H]$^+$. $^1$H NMR (300 MHz; CDCl$_3$): δ 1.01-1.07 (6H, m), 1.44-1.73 (3H, t), 2.10-2.18 (1H, m), 3.63 (3H, s), 4.38-4.45 (1H, m), 5.30-5.32 (1H, d), 6.32-6.35 (1H, d), 6.71-6.75 (1H, m), 6.93 (1H, s), 7.10-7.14 (1H, m), 7.34-7.37 (1H, m), 7.54-7.65 (6H, m), 7.94 (1H, s).

Example 11. Preparation of N-[(1R,2S)-1-[4-(difluoromethoxy)phenyl]-3-methyl-1-{[1-(1-methyl-6-oxo-1,6-dihydropyridin-3-yl)-1H-indazol-5-yl]oxy}butan-2-yl]-2,2-difluoropropanamide

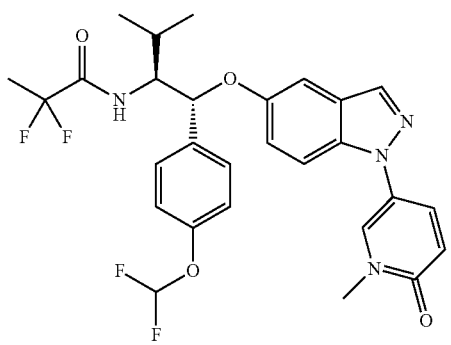

Step A. Preparation of (S)-tert-butyl 1-(4-(tert-butyldimethylsilyloxy)phenyl)-3-methyl-1-oxobutan-2-ylcarbamate

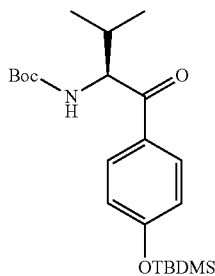 [SMILES: CC(C)[C@H](NC(=O)OC(C)(C)C)C(=O)c1ccc(O[Si](C)(C)C(C)(C)C)cc1]

To a suspension of Mg (2.0 g, 82 mmol) in dry tetrahydrofuran (5 mL) was added a solution of (4-bromophenoxy)(tert-butyl)dimethylsilane (20 g, 70 mmol) in tetrahydrofuran (10 mL). The resulting mixture was stirred at ambient temperature for 1 hr and then added to a solution of (S)-tert-butyl 1-(methoxy(methyl)amino)-3-methyl-1-oxobutan-2-ylcarbamate (6.0 g, 24 mmol) in tetrahydrofuran (20 mL) at 0° C. After stirring overnight at room temperature, the reaction was quenched with aqueous NH$_4$Cl (200 mL). The mixture was then extracted with ethyl acetate (3×50 mL), and the combined organic layer was washed with brine, dried with Na$_2$SO$_4$ and concentrated. The resulting residue was purified by column chromatography eluting with ethyl acetate/petroleum ether 1:5 to afford 3.5 g (36%) of the title compound as a white solid. LCMS: m/z 408 [M+H]$^+$.

Step B. Preparation of tert-butyl (1R,2S)-1-(4-(tert-butyldimethylsilyloxy)phenyl)-1-hydroxy-3-methylbutan-2-ylcarbamate

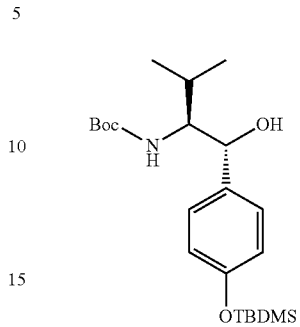

(S)-tert-butyl 1-(4-(tert-butyldimethylsilyloxy)phenyl)-3-methyl-1-oxobutan-2-ylcarbamate (3.5 g, 8.6 mmol) was dissolved in toluene (21 mL), propan-2-ol (5.7 g, 95 mmol) and triisopropoxyaluminum (3.2 g, 16 mmol) was added. The reaction mixture was then heated at 50° C. for 18 hr. Afterward, the reaction mixture was poured into aqueous NH$_4$Cl (200 mL) and extracted with ethyl acetate (2×100 mL). The combined organic layer was washed with brine, dried over Na$_2$SO$_4$ and concentrated, and the resulting residue was purified by column chromatography, eluting with ethyl acetate/petroleum ether (1/5), to afford 3.0 g (85%) of the title product as white solid. LCMS: m/z 336 [M+H-$^t$BuOH]$^+$ Step C. Preparation of tert-butyl (1R,2S)-1-hydroxy-1-(4-hydroxyphenyl)-3-methylbutan-2-ylcarbamate

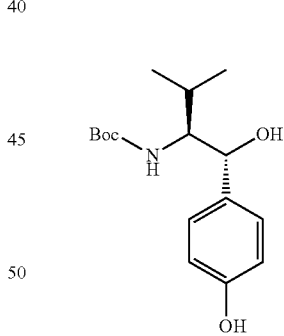

To a solution of tert-butyl (1R,2S)-1-(4-(tert-butyldimethylsilyloxy)phenyl)-1-hydroxy-3-methylbutan-2-ylcarbamate (3.0 g, 7.0 mmol) in tetrahydrofuran (7 mL) was added TBAF (22 mL, 22 mmol). The resulting mixture was stirred at ambient temperature overnight, evaporated and diluted with aqueous NH$_4$Cl (200 mL), and extracted with ethyl acetate (2×100 mL). The combined organic layer was washed by brine, dried over Na$_2$SO$_4$ and concentrated. The resulting residue was purified by column chromatography eluting with ethyl acetate/petroleum ether (1/3) to afford 2.0 g (96%) of the title product as a white solid. LCMS: m/z 294 [M−H]$^−$

Step D. Preparation of tert-butyl (1R,2S)-1-(4-(difluoromethoxy)phenyl)-1-hydroxy-3-methylbutan-2-ylcarbamate

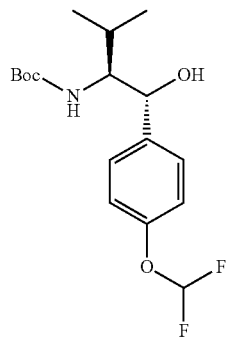 [SMILES: CC(C)[C@H](NC(=O)OC(C)(C)C)[C@H](O)c1ccc(OC(F)F)cc1]

To a solution of 18-crown-6 (0.2 g) and NaOH (1.8 g, 44 mmol) in H₂O (5 mL) was added a solution of tert-butyl (1R,2S)-1-hydroxy-1-(4-hydroxyphenyl)-3-methylbutan-2-ylcarbamate (2 g, 6.8 mmol) in iPrOH (5 mL). The resulting mixture was stirred at ambient temperature for 0.5 hr and then heated to 65° C. Chlorodifluoromethane (gas) was bubbled into the reaction mixture for 6 hr at 65° C. The reaction mixture was then cooled to room temperature, poured into aqueous NH₄Cl (200 mL), and extracted with ethyl acetate (3×50 mL). The combined organic layer was washed with brine, dried with Na₂SO₄ and concentrated. The residue was purified by column chromatography eluting with ethyl acetate/petroleum ether (1/5) to afford 1.0 g (43%) of the title product as a white solid. LCMS: m/z 346 [M−H]⁺

Step E. Preparation of (1R,2S)-2-amino-1-(4-(difluoromethoxy)phenyl)-3-methylbutan-1-ol

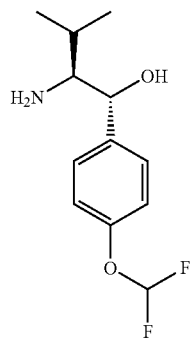 [SMILES: CC(C)[C@H](N)[C@H](O)c1ccc(OC(F)F)cc1]

To a solution of tert-butyl (1R,2S)-1-(4-(difluoromethoxy)phenyl)-1-hydroxy-3-methylbutan-2-ylcarbamate (1 g, 2.8 mmol) in DCM (3 mL) was added TFA (3 mL). The resulting mixture was stirred at ambient temperature for 3 hr. The solution was then evaporated, and the residue was diluted with aqueous NaHCO₃ (100 mL) and extracted with DCM/MeOH (10/1) (3×50 mL). The combined organic layer was dried over NaSO₄, and concentrated to afford 0.6 g (84%) of the crude title product as white solid that was used in the next step without further purification. LCMS: m/z 246 [M+H]⁺

Step F. Preparation of N-[(1R,2S)-1-[4-(difluoromethoxy)phenyl]-3-methyl-1-{[1-(1-methyl-6-oxo-1,6-dihydropyridin-3-yl)-1H-indazol-5-yl]oxy}butan-2-yl]-2,2-difluoropropanamide

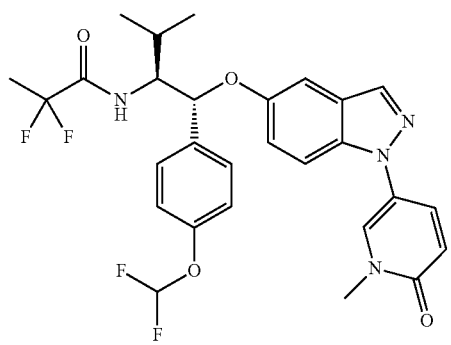

The title compound was prepared following the procedure for Example 2 using 2,2-difluoropropanoic acid to afford 50 mg (34%) of the product. LCMS: m/z 561 [M+H]⁺. ¹HNMR (300 MHz; CD₃OD) δ 1.01-1.04 (6H, m), 1.40-1.52 (3H, t), 2.46-2.52 (1H, m), 3.66 (3H, s), 4.36-4.40 (1H, m), 5.28-5.31 (1H, d), 6.67 (1H, t) 6.70-6.73 (1H, d), 6.78 (1H, t), 7.16-7.22 (4H, m), 7.51-7.54 (3H, m), 7.81-7.85 (1H, m), 8.04-8.07 (2H, m).

Example 12. Preparation of 2,2-difluoro-N-[(1R,2S)-3-methyl-1-{[6-methyl-1-(1-methyl-6-oxo-1,6-dihydropyridin-3-yl)-1H-indazol-5-yl]oxy}-1-phenylbutan-2-yl]propanamide

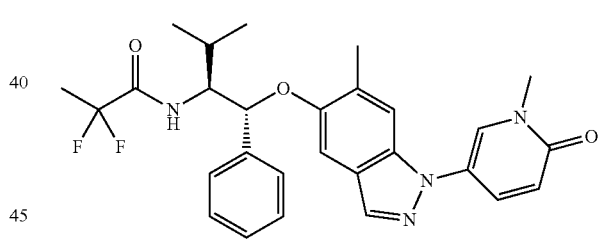

Step A. Preparation of 5-iodo-1-(6-methoxypyridin-3-yl)-6-methyl-1H-indazole

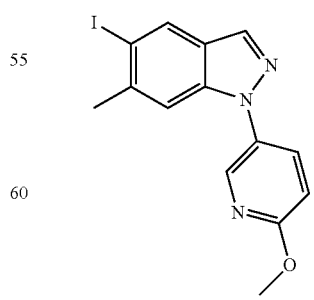

Pyridine (0.38 mL, 4.6 mmol) was added to 5-iodo-6-methyl-1H-indazole (300 mg, 1.16 mmol), (6-methoxypyridin-3-yl)boronic acid (270 mg, 1.7 mmol) and copper (II) acetate (210 mg, 1.2 mmol) in DCM (10 mL). The resulting mixture was stirred at room temperature under air over night and then concentrated under reduced pressure. The crude product was purified by silica gel chromatography eluting with ethyl acetate/petroleum ether 5:95 to afford 340 mg (80%) of the title compound as a yellow oil. LCMS: m/z 366 [M+H]+.

Step B. Preparation of 5-(5-iodo-6-methyl-1H-indazol-1-yl)pyridin-2(1H)-one

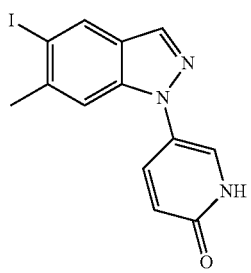 [SMILES: Cc1cc2c(cnn2-c2ccc(=O)[nH]c2)cc1I]

HCl (4.7 mL, 47 mmol) was added to 5-iodo-1-(6-methoxypyridin-3-yl)-6-methyl-1H-indazole (340 mg, 0.93 mmol) in EtOH (5 mL). The resulting mixture was stirred at 80° C. over night and filtered to afford 260 mg (80%) of the title compound as a yellow solid that was used in the next step without further purification. LCMS: m/z 352 [M+H]+

Step C. Preparation of 5-(5-iodo-6-methyl-1H-indazol-1-yl)-1-methylpyridin-2(1H)-one

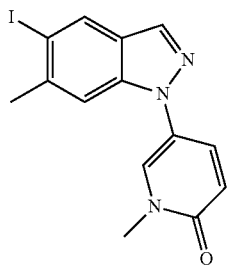 [SMILES: Cc1cc2c(cnn2-c2ccc(=O)n(C)c2)cc1I]

Methyl iodide (0.14 mL, 2.2 mmol) was added dropwise to a mixture of 5-(5-iodo-6-methyl-1H-indazol-1-yl)pyridin-2-ol (260 mg, 0.74 mmol) and K₂CO₃ (360 mg, 2.6 mmol) in DMF (5 mL) at 0° C. The resulting mixture was stirred at room temperature over night, diluted with ethyl acetate (50 mL) and washed with water (50 mL) and brine (50 mL). The organic layer was dried over Na₂SO₄, filtered and evaporated to afford 200 mg (74%) of the title compound as a brown solid that was used in the next reaction without further purification. LC/MS: m/z 366 [M+H]+

Step D. Preparation of 2,2-difluoro-N-[(1R,2S)-3-methyl-1-{[6-methyl-1-(1-methyl-6-oxo-1,6-dihydropyridin-3-yl)-1H-indazol-5-yl]oxy}-1-phenylbutan-2-yl]propanamide

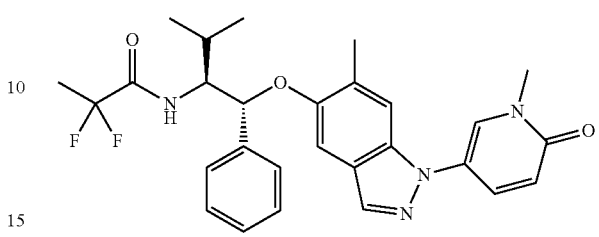

The title compound was prepared following the procedure for Example 2 using 5-(5-iodo-6-methyl-1H-indazol-1-yl)-1-methylpyridin-2(1H)-one in step D and 2,2-difluoropropanoic acid in step E, to afford 50 mg (30%) product. LCMS: m/z 509 [M+H]+. ¹HNMR (300 MHz, CD₃OD, ppm): δ 1.00 (m, 6H), 1.45 (t, 3H), 2.45 (m, 4H), 3.60 (s, 3H), 4.42 (m, 1H), 5.36 (d, 1H), 6.65 (d, 1H), 7.00 (s, 1H), 7.30 (m, 4H), 7.50 (d, 2H), 7.75 (m, 1H), 7.95 (s, 1H), 8.00 (brs, 1H).

Example 13. Preparation of N-[(1R,2S)-1-(4-chlorophenyl)-3-methyl-1-{[1-(1-methyl-6-oxo-1,6-dihydropyridin-3-yl)-1H-indazol-5-yl]oxy}butan-2-yl]-2,2,2-trifluoroacetamide

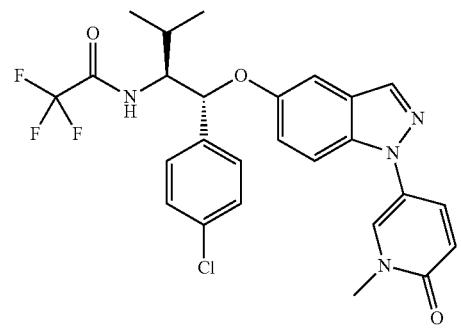 [SMILES: CC(C)[C@H](NC(=O)C(F)(F)F)[C@H](Oc1ccc2c(cnn2-c2ccc(=O)n(C)c2)c1)c1ccc(Cl)cc1]

Step A. 5-(5-((1R,2S)-2-amino-1-(4-chlorophenyl)-3-methylbutoxy)-1H-indazol-1-yl)-1-methylpyridin-2(1H)-one

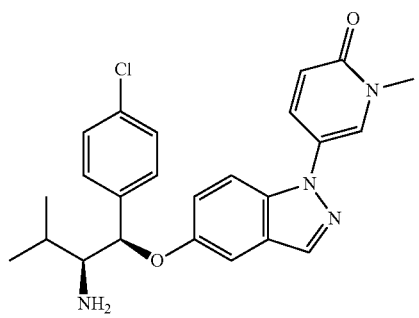 [SMILES: CC(C)[C@H](N)[C@H](Oc1ccc2c(cnn2-c2ccc(=O)n(C)c2)c1)c1ccc(Cl)cc1]

The title compound was prepared following the procedure for Example 2.

Step B. Preparation of N-[(1R,2S)-1-(4-chlorophenyl)-3-methyl-1-{[1-(1-methyl-6-oxo-1,6-dihydropyridin-3-yl)-1H-indazol-5-yl]oxy}butan-2-yl]-2,2,2-trifluoroacetamide

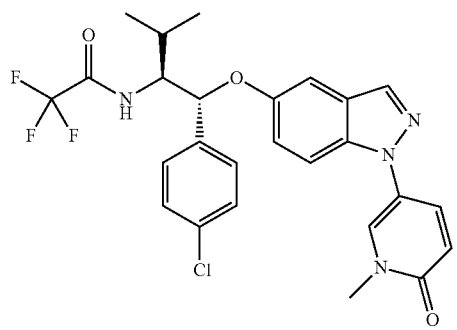 [SMILES: CC(C)[C@H](NC(=O)C(F)(F)F)[C@H](Oc1ccc2c(cnn2-c2ccc(=O)n(C)c2)c1)c1ccc(Cl)cc1]

Into a 50-mL round-bottom flask was placed 5-(5-((1R,2S)-2-amino-1-(4-chlorophenyl)-3-methylbutoxy)-1H-indazol-1-yl)-1-methylpyridin-2(1H)-one (150 mg, 0.34 mmol, 1.00 equiv), DCM (10 mL), and TEA (104 mg, 1.03 mmol, 3.00 equiv). This was followed by the addition of trifluoroacetyl 2,2,2-trifluoroacetate (108 mg, 0.51 mmol, 1.50 equiv) drop wise with stirring at 0° C. The resulting solution was stirred for 2 hr at 0° C. The mixture was then washed with H$_2$O. Afterward, the mixture was dried over anhydrous sodium sulfate and concentrated under vacuum. The resulting residue was applied onto a silica gel column with DCM/MeOH (50:1). This resulted in 98 mg (41%) of the title compound as a light yellow solid. LC/MS: m/z 533/535 3:1 [M+H]$^+$. $^1$HNMR (300 MHz; CDCl$_3$): δ 1.02 (m, 6H), 2.05 (m, 1H), 3.62 (s, 3H), 4.35 (m, 1H), 5.30 (d, 1H), 6.24 (d, 1H), 6.74 (d, 1H), 6.92 (s, 1H), 7.10 (d, 1H), 7.35 (m, 5H), 7.65 (m, 2H), 7.94 (s, 1H).

Example 14. Preparation of N-[(1R,2S)-1-(3,5-dichlorophenyl)-3-methyl-1-{[1-(1-methyl-6-oxo-1,6-dihydropyridin-3-yl)-1H-indazol-5-yl]oxy}butan-2-yl]-2,2,2-trifluoroacetamide

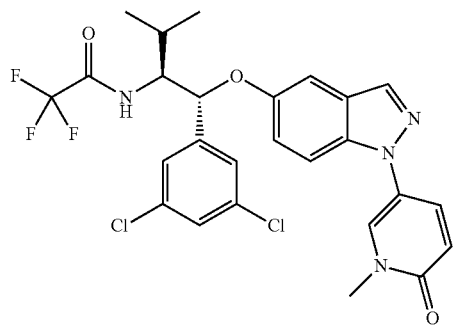 [SMILES: CC(C)[C@H](NC(=O)C(F)(F)F)[C@H](Oc1ccc2c(cnn2-c2ccc(=O)n(C)c2)c1)c1cc(Cl)cc(Cl)c1]

The title compound was prepared following the procedure for Example 13 to afford 50 mg (28%) product. LC/MS: m/z 567 [M+H]$^+$. $^1$HNMR (300 MHz, CD$_3$OD): δ 0.90-0.96 (m, 6H), 2.39 (m, 1H), 3.50 (s, 3H), 4.15-4.16 (m, 1H), 5.31-5.34 (d, 1H), 6.53-6.56 (d, 1H), 7.15-7.19 (m, 2H), 7.51-7.74 (m, 5H), 8.17-8.19 (m, 2H), 9.10-9.13 (m, 1H).

Example 15. Preparation of 2,2,2-trifluoro-N-{(1R,2S)-3-methyl-1-{[1-(1-methyl-6-oxo-1,6-dihydropyridin-3-yl)-1H-indazol-5-yl]oxy}-1-[4-(trifluoromethyl)phenyl]butan-2-yl}acetamide

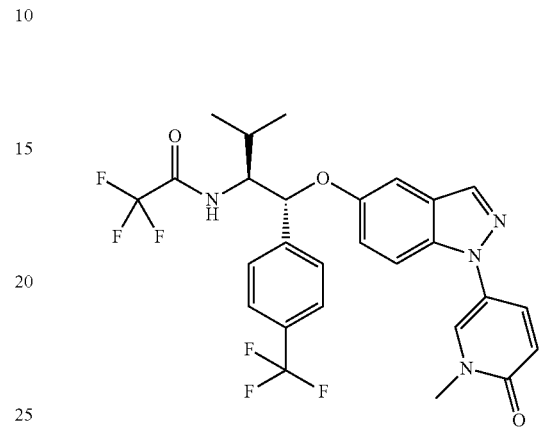

The title compound was prepared following the procedure for Example 13 to afford 60 mg (24%) product. LC/MS: m/z 567 [M+H]$^+$. $^1$HNMR (300 MHz; CD$_3$OD): δ 1.01-1.08 (6H, m), 2.02-2.13 (1H, m), 3.63 (3H, s), 4.40-4.47 (1H, m), 5.38-5.40 (1H, d), 6.30-6.33 (1H, d), 6.72-6.76 (1H, dd), 6.92 (1H, s), 7.10-7.14 (1H, m), 7.35-7.38 (1H, m), 7.53-7.67 (6H, m), 7.95 (1H, s).

Example 16. Preparation of N-[(1R,2S)-1-[4-(difluoromethoxy)phenyl]-3-methyl-1-{[1-(1-methyl-6-oxo-1,6-dihydropyridin-3-yl)-1H-indazol-5-yl]oxy}butan-2-yl]-2,2,2-trifluoroacetamide

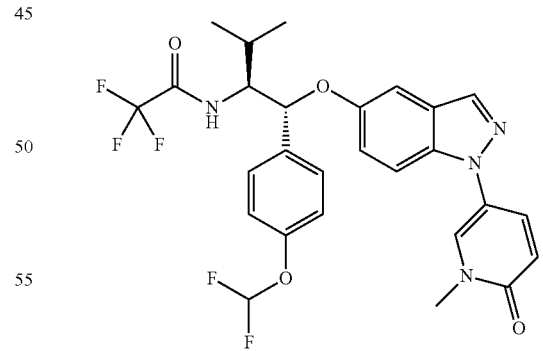

The title compound was prepared following the procedure for Example 13 to afford 50 mg (26%) product. The amino alcohol used in step 7 was prepared as described in Example 14. LC/MS: m/z 565 [M+H]$^+$. $^1$HNMR (300 MHz; CD$_3$OD) δ 0.99-1.04 (6H, m), 2.43-2.49 (1H, m), 3.63 (3H, s), 4.33-4.38 (1H, m), 5.26-5.28 (1H, d), 6.68-6.70 (1H, d), 6.74 (1H, t), 7.12-7.19 (4H, m), 7.46-7.51 (3H, m), 7.78-7.82 (1H, m), 8.02-8.04 (2H, m).

Example 17. Preparation of N-[(1R,2S)-1-(4-chloro-3-fluorophenyl)-3-methyl-1-{[1-(1-methyl-6-oxo-1,6-dihydropyridin-3-yl)-1H-indazol-5-yl]oxy}butan-2-yl]-2,2,2-trifluoroacetamide

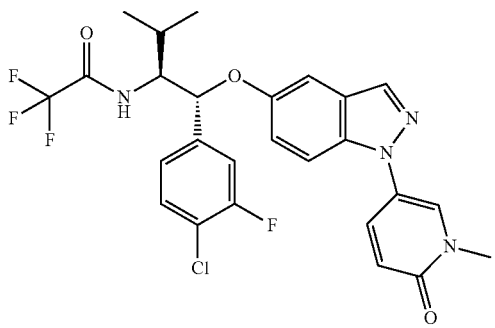 [SMILES: CC(C)[C@H](NC(=O)C(F)(F)F)[C@H](Oc1ccc2c(cnn2-c2ccc(=O)n(C)c2)c1)c1ccc(Cl)c(F)c1]

The title compound was prepared following the procedure for Example 13 to afford 124 mg (81%) of the product. The Grignard reagent in Scheme 2 was generated in situ from magnesium powder (1.0 g, 41 mmol) and lithium chloride (2.5 g, 59 mmol) were mixed under $N_2$ in dry tetrahydrofuran (116 mL) and then cooled to −10° C. Isopropyl magnesium chloride (2 M in tetrahydrofuran) (15 mL, 30 mmol) was added at a rate keeping the temperature below −5° C. The cooling bath was removed and 4-bromo-1-chloro-2-fluorobenzene (6.7 g, 32 mmol) was added portionwise, maintaining the temperature below 5° C. during the addition. LC/MS: m/z 551/553 3:1 [M+H]$^+$. $^1$HNMR (500 MHz; CDCl$_3$): δ 1.03 (d, 3H), 1.07 (d, 3H), 2.13 (dq, 1H), 3.63 (s, 3H), 4.38 (dt, 1H), 5.29 (d, 1H), 6.36 (d, 1H), 6.72 (dd, 1H), 6.93 (d, 1H), 7.11 (dd, 1H), 7.17 (dd, 1H), 7.22 (dd, 1H), 7.37 (d, 1H), 7.4-7.47 (m, 1H), 7.59-7.67 (m, 2H), 7.96 (d, 1H).

Example 18. Preparation of N-[(1R,2S)-1-[3-chloro-5-fluorophenyl]-3-methyl-1-{[1-(1-methyl-6-oxo-1,6-dihydropyridin-3-yl)-1H-indazol-5-yl]oxy}butan-2-yl]-2,2,2-trifluoroacetamide

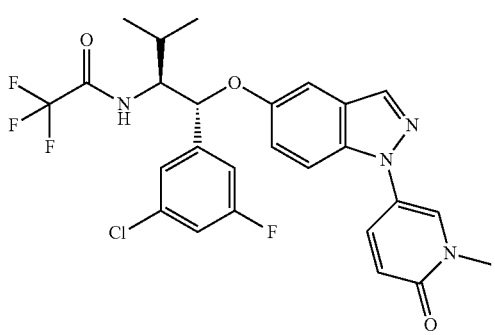 [SMILES: CC(C)[C@H](NC(=O)C(F)(F)F)[C@H](Oc1ccc2c(cnn2-c2ccc(=O)n(C)c2)c1)c1cc(F)cc(Cl)c1]

The title compound was prepared following the procedure for Example 13 to afford 100 mg (62%) of the product. The Grignard reagent in Scheme 2 was prepared as described in Example 17. LC/MS: m/z 551/553 3:1 [M+H]$^+$. $^1$HNMR (500 MHz; CDCl$_3$): δ 1.03 (d, 3H), 1.07 (d, 3H), 2.09-2.2 (m, 1H), 3.64 (s, 3H), 4.37 (dt, 1H), 5.26 (d, 1H), 6.35 (d, 1H), 6.74-6.8 (m, 1H), 6.94 (d, 1H), 7.07 (ddt, 2H), 7.12 (dd, 1H), 7.22 (s, 1H), 7.38 (d, 1H), 7.61-7.71 (m, 2H), 7.99 (s, 1H).

Example 19. Preparation of N-[(1R,2S)-1-(3-chloro-5-fluorophenyl)-3-methyl-1-{[1-(1-methyl-6-oxo-1,6-dihydropyridin-3-yl)-1H-indazol-5-yl]oxy}butan-2-yl]-2,2-difluoropropanamide

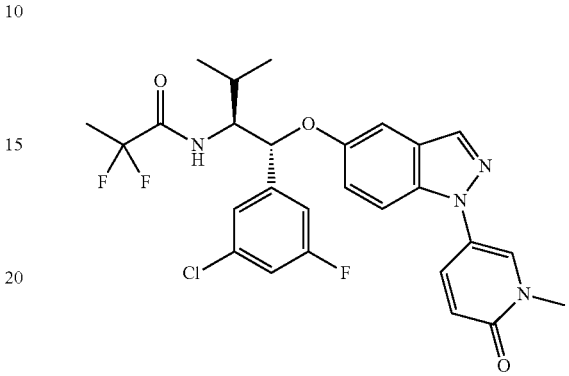

5-(5-((1R,2S)-2-amino-1-(3-chloro-5-fluorophenyl)-3-methylbutoxy)-1H-indazol-1-yl)-1-methylpyridin-2(1H)-one (140 mg, 0.30 mmol) was dissolved in DMF (2 mL) and 2,2-difluoropropanoic acid (82 mg, 0.75 mmol), TBTU (240 mg, 0.75 mmol) and DIPEA (0.31 mL, 1.8 mmol) were added. The reaction mixture was stirred at room temperature overnight, quenched with water, extracted with DCM, dried (MgSO$_4$) and concentrated. The product was purified on a column chromatography, eluting with a gradient of ethyl acetate (0-100%) in heptane and concentrated. Co-eluting DMF was removed by dissolving the residue in DCM (20 mL), washing with water (3×20 mL), drying (MgSO$_4$) and concentrating to afford 120 mg (73%) of the title compound. LC/MS: m/z 547/549 3:1 [M+H]$^+$. $^1$HNMR (500 MHz; CDCl$_3$): δ 1.00 (d, 3H), 1.05 (d, 3H), 1.71 (t, 3H), 2.14-2.24 (m, 1H), 3.63 (s, 3H), 4.3-4.37 (m, 1H), 5.19 (d, 1H), 6.40 (d, 1H), 6.71-6.76 (m, 1H), 6.94 (d, 1H), 7.04 (dt, 1H), 7.07 (d, 1H), 7.12 (dd, 1H), 7.22 (s, 1H), 7.37 (d, 1H), 7.61-7.67 (m, 2H), 7.98 (d, 1H). The Grignard reagent used here was prepared as described in Example 17.

Example 20. Preparation of N-[(1R,2S)-1-(4-chloro-3-fluorophenyl)-3-methyl-1-{[1-(1-methyl-6-oxo-1,6-dihydropyridin-3-yl)-1H-indazol-5-yl]oxy}butan-2-yl]-2,2-difluoropropanamide

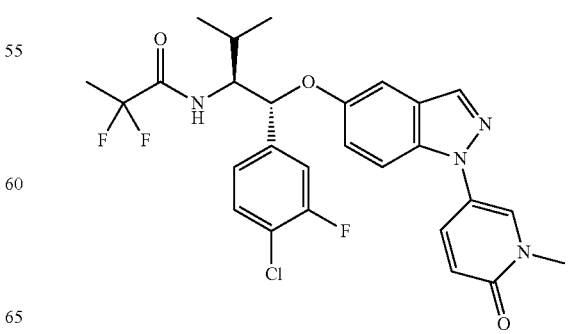

The title compound was prepared following the procedure for Example 23 to afford 83 mg (57%) of the product. The Grignard reagent used here was prepared as described in Example 17. LC/MS: m/z 547/549 3:1 [M+H]⁺. ¹HNMR (500 MHz; CDCl₃): δ 1.00 (d, 3H), 1.04 (d, 3H), 1.71 (t, 3H), 2.12-2.21 (m, 1H), 3.62 (s, 3H), 4.35 (dt, 1H), 5.22 (d, 1H), 6.38 (d, 1H), 6.71 (dd, 1H), 6.93 (d, 1H), 7.11 (dd, 1H), 7.17 (dd, 1H), 7.22 (dd, 1H), 7.36 (d, 1H), 7.40 (t, 1H), 7.58-7.67 (m, 2H), 7.96 (s, 1H).

Example 21. Preparation of N-[(1R,2S)-1-{[6-chloro-1-(1-methyl-6-oxo-1,6-dihydropyridin-3-yl)-1H-indazol-5-yl]oxy}-3-methyl-1-phenylbutan-2-yl]-2,2-difluoropropanamide

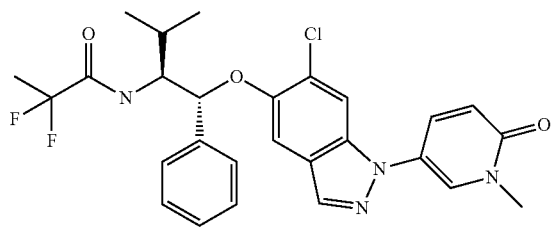 [SMILES: CC(C)[C@H](NC(=O)C(C)(F)F)[C@H](Oc1cc2cnn(-c3ccc(=O)n(C)c3)c2cc1Cl)c1ccccc1]

Step A. Preparation of 5-((tert-butyldimethylsilyl)oxy)-6-chloro-1H-indazole

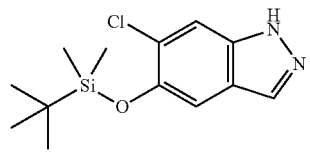 [SMILES: CC(C)(C)[Si](C)(C)Oc1cc2cn[nH]c2cc1Cl]

To a mixture of 6-chloro-1H-indazol-5-ol (0.5 g, 3.0 mmol) and 1H-imidazole (0.50 mL, 4.5 mmol) in DCM (8 mL) were added tert-butylchlorodimethylsilane (0.47 g, 3.1 mmol) at 0° C. The resulting mixture was stirred at room temperature over night. Afterward, the mixture was poured into 0.5 M aqueous citric acid (40 mL) and extracted with DCM (2×60 mL). The combined organic layer was dried with a phase separator and concentrated to afford 0.70 g of the crude title product that was used in the next step without further purification. ¹HNMR (500 MHz, DMSO-d6): δ 0.23 (s, 6H), 1.02 (s, 9H), 7.32 (s, 1H), 7.64 (s, 1H), 7.97 (s, 1H), 12.99 (s, 1H).

Step B. Preparation of 5-(5-((tert-butyldimethylsilyl)oxy)-6-chloro-1H-indazol-1-yl)-1-methylpyridin-2(1H)-one

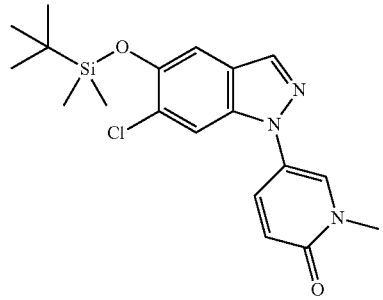 [SMILES: Cn1cc(-n2ncc3cc(O[Si](C)(C)C(C)(C)C)c(Cl)cc32)ccc1=O]

5-((tert-butyldimethylsilyl)oxy)-6-chloro-1H-indazole (0.70 g) and 5-iodo-1-methylpyridin-2(1H)-one (Example 1, Step B) (0.64 g, 2.7 mmol) were mixed in toluene (2 mL) and heated gently to dissolve at 50° C. The resulting mixture was evacuated and purged with N₂ several times. Potassium phosphate (0.43 mL, 5.2 mmol) and (1S,2S)-cyclohexane-1,2-diamine (0.060 mL, 0.50 mmol) were added, followed by copper(I) iodide (0.028 g, 0.15 mmol). The mixture was then heated to 110° C. for 19 hr. Afterward, the mixture was cooled to room temperature and diluted with ethyl acetate (120 mL), washed with 1M HCl (50 mL), and saturated ascorbic acid (30 mL). The organic and aqueous layers were separated on a phase separator. The organic layer was concentrated to yield 1.2 g of the title product as a purple/brown oil that was used in the next step without further purification.

Step C. Preparation of 5-(6-chloro-5-hydroxy-1H-indazol-1-yl)-1-methylpyridin-2(1H)-one

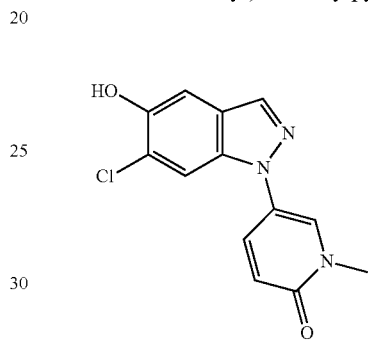

To a solution of 5-(5-((tert-butyldimethylsilyl)oxy)-6-chloro-1H-indazol-1-yl)-1-methylpyridin-2(1H)-one (1.2 g) in ethanol (7 mL) was added potassium hydroxide (0.26 g, 4.7 mmol) at room temperature. The resulting mixture was stirred for 2.5 hr. Water (40 mL) was added, and the mixture was washed with MTBE (40 mL), acidified with 3.8 M HCl to pH 4, extracted with 2-methyltetrahydrofuran (2×30 mL), and dried with a phase separator to yield 0.45 g (54%, 3 steps) of the title compound that was used in the next step without further purification. ¹HNMR (500 MHz, DMSO-d6): δ 3.52 (s, 3H), 6.54 (d, 1H), 7.28 (s, 1H), 7.72 (dd, 1H), 7.78 (s, 1H), 8.12-8.19 (m, 1H), 8.20 (s, 1H), 10.08 (s, 1H).

Step D. Preparation of N-((1R,2S)-1-((6-chloro-1-(1-methyl-6-oxo-1,6-dihydropyridin-3-yl)-1H-indazol-5-yl)oxy)-3-methyl-1-phenylbutan-2-yl)-4-nitrobenzenesulfonamide

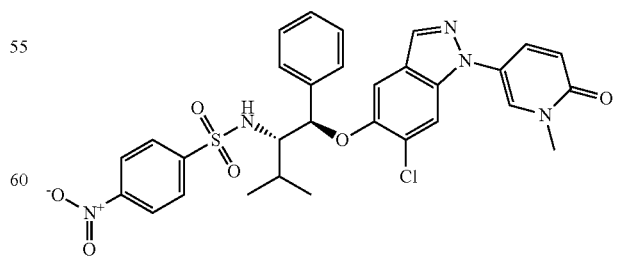

To a solution of (2S,3S)-2-isopropyl-1-((4-nitrophenyl)sulfonyl)-3-phenylaziridine (Example 1, Step E) (0.5 g, 1.1 mmol) and 5-(6-chloro-5-hydroxy-1H-indazol-1-yl)-1- methylpyridin-2(1H)-one (0.42 g, 1.2 mmol) in acetonitrile (7 mL) was added cesium carbonate (0.75 g, 2.3 mmol). The resulting mixture was heated to 50° C. over night. Afterward, the mixture was cooled to room temperature, poured into water (30 mL) and extracted with 2-methyltetrahydrofuran (2×40 mL). The combined organic layer was washed with water, dried with a phase separator and concentrated. The resulting residue was purified by automated flash chromatography on a Biotage® KP-SIL eluting with a gradient from 0-100% ethyl acetate in heptane to yield 0.43 g (63%) of the title product. $^1$HNMR (500 MHz, DMSO-d6): δ 0.89 (d, 3H), 0.98 (d, 3H), 2.23 (s, 1H), 3.49 (s, 3H), 3.79 (s, 1H), 5.17 (d, 1H), 6.52 (d, 1H), 6.94 (s, 1H), 7.04 (d, 1H), 7.09 (t, 2H), 7.24 (d, 2H), 7.66 (dd, 1H), 7.72 (d, 2H), 7.81 (s, 1H), 8.04 (s, 1H), 8.11 (d, 2H), 8.13-8.19 (m, 2H).

Step E. Preparation of N-[(1R,2S)-1-{[6-chloro-1-(1-methyl-6-oxo-1,6-dihydropyridin-3-yl)-1H-indazol-5-yl]oxy}-3-methyl-1-phenylbutan-2-yl]-2,2-difluoropropanamide

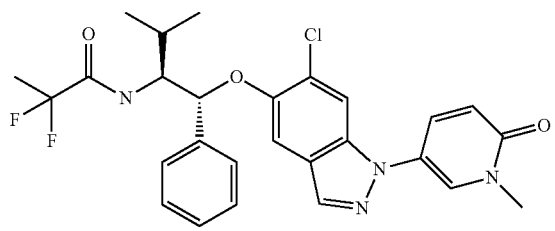 [SMILES: CC(C)[C@H](NC(=O)C(C)(F)F)[C@H](Oc1cc2cnn(-c3ccc(=O)n(C)c3)c2cc1Cl)c1ccccc1]

N-((1R,2S)-1-((6-chloro-1-(1-methyl-6-oxo-1,6-dihydropyridin-3-yl)-1H-indazol-5-yl)oxy)-3-methyl-1-phenylbutan-2-yl)-4-nitrobenzenesulfonamide (0.37 g, 0.60 mmol) was dissolved in DMF (4 mL), and DBU (0.27 mL, 1.8 mmol) was added dropwise to the solution, followed by 2-mercaptoacetic acid (0.084 mL, 1.2 mmol). The reaction mixture was subsequently stirred at room temperature for 2 hr and then divided in two equal volumes. One volume was used in Example 22. The other volume (0.132 g, 0.30 mmol) was stirred at room temperature, and ethyl 2,2-difluoropropanoate (0.125 g, 0.91 mmol) was added dropwise. The resulting mixture was stirred at room temperature for 18 hr, followed by heating to 45° C. for 2 hr. Afterward, the mixture was allowed to cool to room temperature. The reaction was quenched with water and diluted with ethyl acetate (30 mL). The aqueous layer was extracted twice with ethyl acetate, and the combined organic layer was dried on a phase separator, concentrated and purified on SFC to afford 63 mg (40%) of the title compound. LC/MS: m/z 529/531 3:1 [M+H]$^+$. $^1$HNMR (600 MHz, DMSO-d6): δ 0.92 (t, 6H), 1.41 (t, 3H), 2.43 (d, 1H), 3.50 (s, 3H), 4.27 (d, 1H), 5.42 (d, 1H), 6.52 (d, 1H), 7.18 (s, 1H), 7.23 (t, 1H), 7.31 (t, 2H), 7.48 (d, 2H), 7.67 (dd, 1H), 7.86 (s, 1H), 8.11-8.22 (m, 2H), 8.30 (d, 1H).

Example 22. Preparation of N-[(1R,2S)-1-{[6-chloro-1-(1-methyl-6-oxo-1,6-dihydropyridin-3-yl)-1H-indazol-5-yl]oxy}-3-methyl-1-phenylbutan-2-yl]-2,2,2-trifluoroacetamide

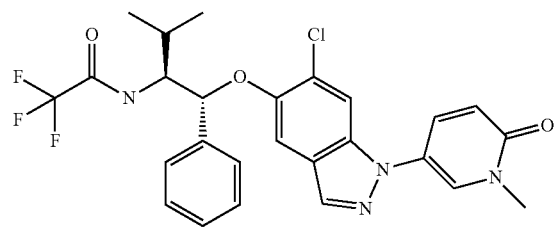

One volume of the intermediate reaction mixture from Example 21 (0.132 g, 0.30 mmol) was stirred at room temperature while adding ethyl 2,2,2-trifluoroacetate (0.108 mL, 0.91 mmol) dropwise. The resulting mixture was stirred at room temperature for 5 hr, quenched with water and diluted with ethyl acetate (30 mL). The aqueous layer was extracted twice with ethyl acetate and the combined organic layer was dried on a phase separator, concentrated and purified on SFC to yield 89 mg (55%) of the title compound. LC/MS: m/z 533/535 3:1 [M+H]$^+$. $^1$HNMR (600 MHz, DMSO-d6): δ 0.95 (dd, 6H), 2.42 (d, 1H), 3.50 (s, 3H), 4.27 (d, 1H), 5.44 (d, 1H), 6.52 (d, 1H), 7.22 (s, 1H), 7.26 (d, 1H), 7.32 (t, 2H), 7.46 (d, 2H), 7.67 (dd, 1H), 7.86 (s, 1H), 8.14 (d, 1H), 8.18 (d, 1H), 9.11 (d, 1H).

Example 23. Preparation of N-[(1R,2S)-1-{[1-(1-ethyl-6-oxo-1,6-dihydropyridin-3-yl)-1H-indazol-5-yl]oxy}-3-methyl-1-phenylbutan-2-yl]-2,2-difluoropropanamide

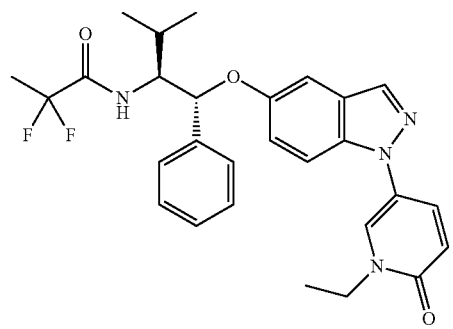 [SMILES: CCn1cc(-n2ncc3cc(O[C@H](c4ccccc4)[C@@H](NC(=O)C(C)(F)F)C(C)C)ccc32)ccc1=O]

Step A. Preparation of (1R,2S)-3-methyl-1-phenyl-1-(1-(tetrahydro-2H-pyran-2-yl)-1H-indazol-5-yloxy)butan-2-amine

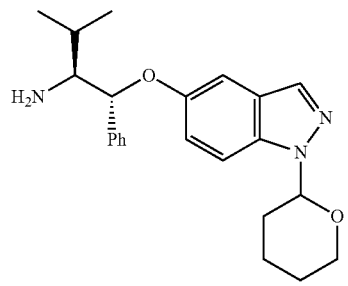 [SMILES: CC(C)[C@H](N)[C@H](Oc1ccc2c(cnn2C2CCCCO2)c1)c1ccccc1]

(1R,2S)-2-amino-3-methyl-1-phenylbutan-1-ol (Example 1, Step D) (2.8 g, 15 mmol), 5-iodo-1-(tetrahydro-2H-pyran-2-yl)-1H-indazole (5 g, 15 mmol), copper(I) iodide (1.5 g, 7.6 mmol), 2-(dimethylamino)acetic acid (1.6 g, 15 mmol) and cesium carbonate (15 g, 45 mmol) were mixed in butyronitrile (100 mL). The resulting mixture was stirred at 130° C. for 20 hr. The crude product was purified by silica gel chromatography, eluting with DCM/MeOH (20/1) to afford 3.0 g (53%) of the title product as a brown gum. LC/MS: m/z 380 [M+H]+

Step B. Preparation of 2,2-difluoro-N-[(1R,2S)-3-methyl-1-[[1-(oxan-2-yl)-1H-indazol-5-yl]oxy]-1-phenylbutan-2-yl]propanamide

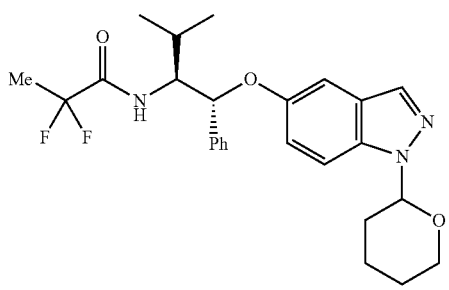 [SMILES: CC(C)[C@H](NC(=O)C(C)(F)F)[C@H](Oc1ccc2c(cnn2C2CCCCO2)c1)c1ccccc1]

Into a 100-mL round-bottom flask was placed 5-[(1R,2S)-2-amino-3-methyl-1-phenylbutoxy]-1-(oxan-2-yl)-1H-indazole (3.0 g, 7.9 mmol), DMF (20 mL), DIPEA (3.1 g, 24 mmol), 2,2-difluoropropanoic acid (1.7 g, 15 mmol) and HATU (6 g, 16 mmol). The resulting solution was stirred overnight at room temperature. The resulting mixture was poured into water and extracted with DCM, and the combined organic layer was concentrated. The residue was purified on column chromatography, eluting with DCM/MeOH (20:19) to afford 3.4 g (91%) of the title compound as a brown solid. LC/MS: m/z 472 [M+H]+

Step C. Preparation of N-((1R,2S)-1-(1H-indazol-5-yloxy)-3-methyl-1-phenylbutan-2-yl)-2,2-difluoropropanamide

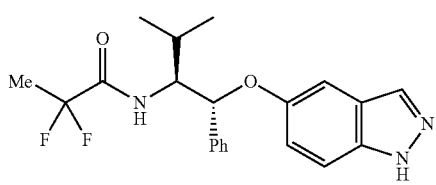 [SMILES: CC(C)[C@H](NC(=O)C(C)(F)F)[C@H](Oc1ccc2[nH]ncc2c1)c1ccccc1]

Into a 100-mL round-bottom flask was placed 2,2-difluoro-N-[(1R,2S)-3-methyl-1-[[1-(oxan-2-yl)-1H-indazol-5-yl]oxy]-1-phenylbutan-2-yl]propanamide (4.2 g, 8.9 mmol), DCM (15 mL) and trifluoroacetic acid (7 mL). The resulting solution was stirred over night at room temperature and then concentrated under vacuum. Afterward, the pH of the solution was adjusted to pH 7-8 with aqueous sodium bicarbonate. The resulting solution was extracted with DCM. The combined organic layer was dried over anhydrous Na2SO4 and concentrated under vacuum to afford 3.4 g (98%) of the title compound as a brown solid. The crude compound was used in the next step without further purification. LC/MS: m/z 388 [M+H]+

Step D. Preparation of 5-bromo-1-ethylpyridin-2(1H)-one

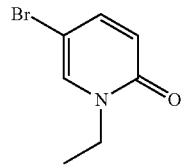

To a solution of 5-bromopyridin-2(1H)-one (1.0 g, 6.0 mmol) and K2CO3 (2.0 g, 15 mmol) in DMF (10 mL) was added ethyl bromide (0.7 g, 7.5 mmol). The resulting mixture was stirred overnight at room temperature. Afterward, the mixture was diluted with ethyl acetate (50 mL), washed with H2O (50 mL) and brine (100 mL), dried over Na2SO4 and concentrated. The residue was purified by silica gel chromatography eluting with petroleum ether/ethyl acetate (20/1) to afford 0.9 g (74%) of the title product as a brown oil. LC/MS: m/z 202 [M+H]+

Step F. Preparation of 1-ethyl-6-oxo-1,6-dihydropyridin-3-ylboronic acid

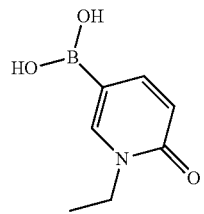

To a solution of 5-bromo-1-ethylpyridin-2(1H)-one (0.9 g, 4.5 mmol, 1.0 equiv), (PinB)2 (1.7 g, 6.7 mmol) and KOAc (1.9 g, 130 mmol) in dioxane (6 mL) was added Pd(dppf)Cl2 (0.3 g) under N2. The resulting solution was stirred at 80° C. for 3 hr under N2. Afterward, the mixture was diluted with ethyl acetate (100 mL), and washed with H2O (50 mL) and brine (100 mL). The organics were dried over Na2SO4, and the resulting residue was purified by silica gel chromatography eluting with petroleum ether/ethyl acetate (10/1) to afford 0.2 g (27%) of the title product as a brown oil. The crude product was used in the next step without further purification. LC/MS: m/z 168 [M+H]+

Step G. Preparation of N-[(1R,2S)-1-{[1-(1-ethyl-6-oxo-1,6-dihydropyridin-3-yl)-1H-indazol-5-yl]oxy}-3-methyl-1-phenylbutan-2-yl]-2,2-difluoropropanamide

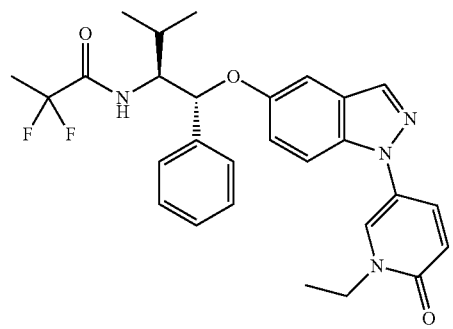 [SMILES: CCn1cc(-n2ncc3cc(O[C@H](c4ccccc4)[C@@H](NC(=O)C(C)(F)F)C(C)C)ccc32)ccc1=O]

Copper (II) acetate (77 mg, 0.42 mmol) was added to a stirred mixture of N-((1R,2S)-1-(1H-indazol-5-yloxy)-3-methyl-1-phenylbutan-2-yl)-2,2-difluoropropanamide (150 mg, 0.4 mmol), 1-ethyl-6-oxo-1,6-dihydropyridin-3-ylboronic acid (160 mg, 1.0 mmol) and pyridine (120 mg, 1.6 mmol) in DCM (3 mL) at room temperature open to the air (vial not sealed). The resulting mixture was stirred over night. The solids were then filtered off, and the filtrate was concentrated under vacuum. The crude product was purified by Prep-HPLC to afford 21 mg (10%) of the title compound as a white solid. LC/MS: m/z 509 [M+H]$^+$. $^1$HNMR (300 MHz; CDCl$_3$): δ 1.01-1.10 (m, 6H), 1.33-1.46 (m, 6H), 2.46-2.49 (m, 1H), 4.08-4.15 (m, 2H), 4.36-4.61 (m, 1H), 5.25-5.28 (m, 1H), 6.68-6.71 (d, 1H), 7.14-7.40 (m, 5H), 7.47-7.51 (m, 3H), 7.79-7.83 (m, 1H), 8.02-8.06 (m, 2H).

Example 24. Biological Evaluation

GRE Agonist Assay

A reporter cell line (ChagoK1 18:7:2 s4/GRE) was established by stable transfection of the human bronchogenic carcinoma cell line, ChaGo K1 (ATCC: HTB 168) with a MMTV-GRE-LacZ reporter construct. The generated cell line allows for identification of compounds showing agonist activity at the human glucocorticoid receptor (GR) via induction of LacZ gene expression. Ligand-activated GR binds to the Glucocorticoid Response Element (GRE) in the promoter of the LacZ gene and transcription is initiated. The resulting beta-galactosidase activity is measured through a colour reaction (change in absorbance).

Cryo-preserved ChagoK1 18:7:2 s4/GRE cells were suspended in RPMI medium with 10% FBS, 1% NEAA and 1% sodium pyruvate, and seeded as 50000 cells/200 ul/well in 96-well plates and cultured at 37° C. with 5% CO$_2$ and 95% humidity for 24 hours. 1 µl compound was added at different concentrations to the cells and incubated for another 24 hours. Cells were washed once in PBS and lysed with 50 µl of 0.1% Triton-X for 10 min at room temperature. 40 µl of reaction mixture (2.5 mM MgCl$_2$, 0.1 M β-mercapto ethanol, 1.7 mg/ml ONPG and 42.5 mM sodium phosphate, pH 7.5), was added to each well and kept at 37° C. for 60 min. The reaction was then terminated by addition of 100 µl stop solution (300 mM glycine, 15 mM EDTA, pH 11.3, adjusted with NaOH). The plates were measured at 420 nm for absorbance in a SpectraMax reader (Molecular Device).

The relative efficacy (% effect) of a compound is calculated based on the full agonist effect of dexamethasone:

% Effect=((Sample abs−min abs)/(max abs−min abs))×100

To calculate EC50, max, min and slope factor for each compound, a concentration response curve is fitted by plotting % Effect versus compound concentration using the 4 parameter logistic equation:

$$y=A+(B-A)/(1+((10C)/x)D)$$

Where A=min Y, B=max Y, C=log EC50 and D=Slope factor

GRE Antagonist Assay

A reporter cell line (ChagoK1 18:7:2 s4/GRE) was established by stable transfection of the human bronchogenic carcinoma celline, ChaGo K1 (ATCC: HTB 168) with a MMTV-GRE-LacZ reporter construct. The generated cell line allows for identification of compounds showing antagonist activity at the human glucocorticoid receptor (GR) via reduction of LacZ gene expression. Dexamethasone-activated GR binds to the Glucocorticoid Response Element (GRE) in the promoter of the LacZ gene and transcription is initiated. Antagonistic properties of compounds are assessed as beta-galactosidase intensity reduction from pre-stimulation with dexamethasone through a colour reaction (change in absorbance).

Cryo-preserved ChagoK1 18:7:2 s4/GRE cells were suspended in RPMI medium with 10% FBS, 1% NEAA and 1% sodium pyruvate, and seeded as 50000 cells/200 ul/well in 96-well plates and cultured at 37° C. with 5% CO$_2$ and 95% humidity for 24 hr. Cells were pre-stimulated with 2 µl dexamethasone (70 nM final conc) for 4-5 hr, before addition of 1 µl compound at different concentrations and incubation for an additional 24 hr. Cells were washed once in PBS and lysed with 50 µl of 0.1% Triton-X for 10 min at room temperature. 40 µl of reaction mixture (2.5 mM MgCl2, 0.1 M β-mercapto ethanol, 1.7 mg/ml ONPG and 42.5 mM sodium phosphate, pH 7.5), was added to each well and kept at 37° C. for 60 min. The reaction was then terminated by addition of 100 µl stop solution (300 mM glycine, 15 mM EDTA, pH 11.3, adjusted with NaOH). The plates were measured at 420 nm for absorbance in a SpectraMax reader (Molecular Device).

The relative efficacy (% effect) of a compound is calculated based on the full antagonist effect of the reference compound Mifepristone (RU486):

% Effect=((Sample abs−min abs)/(max abs−min abs))×100

To calculate IC50, max, min and slope factor for each compound, a concentration response curve is fitted by plotting % Effect versus compound concentration using the 4 parameter logistic equation:

$$y=A+(B-A)/(1+((10C)/x)D)$$

Where A=min Y, B=max Y, C=log IC50 and D=Slope factor

Table 1 shows the results of these assays with the compounds of Examples 1-23. "TA" is the transactivation measured in agonist mode in the GRE Agonist Assay, and in antagonist mode in the GRE Antagonist Assay

TABLE 1

Results from Biological Assays

| Example | TA agonist pEC50 | TA agonist Observed max Effect at 1 µM (%) | TA antagonist pIC50 | TA antagonist Observed max Effect at 1 µM (%) |
|---|---|---|---|---|
| 1 | 8.0 | 36 | 6.8 | 56 |
| 2 | 8.2 | 25 | 7.0 | 67 |
| 3 | 8.6 | 44 | 7.6 | 53 |
| 4 | 8.7 | 42 | 8.8 | 51 |
| 5 | 8.6 | 28 | 6.7 | 72 |
| 6 | 8.6 | 24 | 7.3 | 67 |
| 7 | 8.1 | 46 | 7.1 | 54 |
| 8 | 7.7 | 36 | 6.8 | 56 |
| 9 | 7.7 | 22 | 6.9 | 63 |
| 10 | 8.1 | 40 | 7.0 | 51 |
| 11 | 8.1 | 28 | 6.7 | 62 |
| 12 | 8.4 | 46 | 7.1 | 48 |
| 13 | 8.3 | 28 | 6.9 | 72 |
| 14 | 7.7 | 20 | 6.9 | 65 |
| 15 | 8.2 | 27 | 7.3 | 64 |
| 16 | 8.0 | 20 | 6.6 | 75 |
| 17 | 8.4 | 32 | 7.4 | 79 |
| 18 | 8.8 | 32 | 7.6 | 61 |
| 19 | 8.5 | 38 | 7.6 | 58 |
| 20 | 8.3 | 43 | 7.3 | 66 |
| 21 | 8.3 | 42 | 7.3 | 48 |

TABLE 1-continued

Results from Biological Assays

| Example | TA agonist pEC50 | TA agonist Observed max Effect at 1 μM (%) | TA antagonist pIC50 | TA antagonist Observed max Effect at 1 μM (%) |
|---|---|---|---|---|
| 22 | 8.5 | 37 | 7.3 | 56 |
| 23 | 7.6 | 14 | 6.4 | 70 |

In Vitro Human Whole Blood

The anti-inflammatory activity of compounds and prednisolone was determined in vitro by their ability to inhibit the release of TNFα from whole blood stimulated with LPS. Venous blood from human donors was collected and anti-coagulated with sodium heparin and transferred to a sterile polystyrene round bottomed plate (Corning) at 190 μL per well.

Compounds were prepared from 10 mM stock solutions in dimethylsulfoxide (DMSO, Sigma) by serially diluting 1/3 in DMSO to produce a master plate with the top concentration at 3.33 mM and the lowerest concentration at 0.1 μM. Compounds from the master plate were added to the blood at 1 μL/well (1/200) dilution to give final concentrations ranging between 16.7 μM and 0.5 nM. Control wells received 1 μL DMSO only and the final DMSO concentration in all wells was 0.5%. The samples were gently mixed and placed into a humidfied incubator (95% air/5% $CO_2$) at 37° C. and incubated for 45 min.

LPS (*E. coli* serotype 0127:B8, Sigma) was diluted in PBS without $CaCl_2/MgCl_2$ (Gibco) to afford a working solution at 600 μg/mL. 10 μL was added to each well to give a final LPS concentration of 30 μg/mL. Unstimulated controls received PBS only at 10 μL/well. The samples were, again, gently mixed and the plates incubated overnight for 18 hr. Following incubation, the blood was centrifuged at 700×g for 5 min, and the plasma removed and transferred to freeze at −20° C. before assay for TNFα release.

TNFα protein levels were determined using an AlphaLISA hTNFa kit (Perkin Elmer) according to the manufacturer's instructions. Briefly, the samples were allowed to return to room temperature and centrifuged at 1500×g for 5 min. Samples were diluted 1/5 (5 μL sample in 20 μL AlphaLISA buffer). At the same time, a standard curve of TNFα was prepared by serial 1/3 dilutions from a stock solution (5000-2 pg/mL). 5 μL sample/standard curve were transferred to a 384-well Optiplate™, and to this was added 20 μL anti-humanTNFa acceptor beads/biotinylated antibody mix. The plate was incubated at room temperature for 60 min. After this incubation, 25 μL streptavidin donor beads were added, and the plate was incubated for a further 60 min in the dark at room temperature. The samples were read at 615 nm with excitation at 680 nm using an Envision plate reader. TNFα in the samples was determined by extrapolation from the standard curve and expressed as pg/mL.

The % inhibition of TNFα was determined by the equation:

% inhibition=(1−(A−B)/(C−B))×100

Here, A=TNFα in LPS stimulated samples containing compound, B=TNFα in unstimulated samples. and C=TNFα in LPS stimulated samples without compound. Percent inhibition was plotted against concentration, and a curve graphed using a 4-parameter curve fit (Xlfit 4.1) to determine the $pIC_{50}$.

TABLE 2

TNFα $pIC_{50}$ for Prednisolone and the Compounds of Example 1, 3 & 6

| Compound | $pIC_{50}$ |
|---|---|
| Prednisolone | 6.6 (n = 56) |
| Example 1 | 6.2 (n = 16) |
| Example 3 | 7.0 (n = 8) |
| Example 6 | 6.4 (n = 6) |

Tyrosine Aminotransferase ("TAT") mRNA Expression In Vitro Assay

The impact of test compounds on hyperglycemic events were assessed by looking at changes in mRNA expression of the gene encoding tyrosine aminotransferase (TAT), which is under direct regulation of the glucocorticoid receptor in human hepatocytes.

Experimental Outline

Human cryopreserved primary hepatocytes (BioreclamationIVT, M00995-P lot EPB) were plated to 24-well collagen I-coated plates (Becton Dickinson, 354408). Cells were allowed to attach for 4 hr before being challenged with test compounds overnight (18 hr). Cells were harvested and total RNA isolated using RNeasy Plus Mini Kit (Qiagen, 74136) followed by cDNA synthesis using High Capacity cDNA reverse transcription kit (Applied Biosystems, 4368813). Real-time RT PCR was performed on an Applied Biosystems 7500 PCR cycler, using Taqman primers for TAT (Life technologies, Hs00356930_m1) and the reference gene hypoxanthine phosphoribosyltransferase 1 (Life technologies, Hs99999909_m1).

Protocol

Human cryopreserved primary hepatocytes were transferred in to pre-warmed (37° C.) plating medium (BioreclamationIVT, Z990003) and diluted to $0.7\times10^6$ viable cells/mL. 500⁴ of the cell suspension was plated to each well of a collagen I coated 24-well plate and cells were allowed to sediment and attach at 37° C. for 4 hr. After incubation, the media was gently discarded and exchanged for insulin, glucose, glutamine, pyruvate free media (BioreclamationIVT, S00304), containing compounds of interest, prednisolone at 1 μM, dissolved in DMSO (final DMSO concentration 0.01%), or DMSO alone as control. The plates were then incubated at 37° C. for an additional 18 hr. Media was discarded, and total RNA isolation (Qiagen) and cDNA synthesis (Applied Biosystems) performed according to the manufactures protocol. Real-time RT PCR was carried out using TaqMan reagents (Life technologies) on the 7500 PCR cycler, and Ct-values for TAT gene expression was normalised to the control gene and expressed as fold change compared to DMSO control using the $2^{-\Delta\Delta Ct}$ method.

TABLE 3

Fold Change Tyrosine Aminotransferase Gene Expression Relative to Control

| Compound | Fold Change Relative to Control (1 μM) |
|---|---|
| Prednisolone | 2.8 (1.3-5.3, n = 10) |
| Example 1 | 1.0 (0.8-1.4, n = 8) |
| Example 3 | 1.5 (1.4-1.55, n = 2) |
| Example 6 | 0.9 (n = 1) |

Unless otherwise indicated, the following apply in this specification:

The terms "halogen" and "halo" means chloro, bromine, fluoro, or iodine. In some embodiments, the halogen atoms in a molecule are selected from the group consisting of chloro or fluoro. In some embodiments, the halogen atoms in a molecule are chloro. And in some embodiments, the halogen atoms in a molecule are fluoro.

When the term "halo" modifies another substituent (e.g., methyl or methoxy), the other substituent is substituted by one or more halo. So, for example, "halomethyl" encompasses a methyl substituted with one halo (e.g., —CFH$_2$), two halo (e.g., —CF$_2$H), or three halo (e.g., —CF$_3$).

The term "pharmaceutically acceptable" is used to characterize a moiety (e.g., a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

In this specification, unless stated otherwise, the terms "inhibitor" and "antagonist" mean a compound that by any means, partly or completely, blocks the transduction pathway leading to the production of a response by the agonist. An agonist may be a full or partial agonist.

The term "disorder", unless stated otherwise, means any condition or disease associated with glucocorticoid receptor activity.

References made in the singular may also include the plural. For example, "a" and "an" may refer to either one or more than one.

The word "including" in this specification is to be interpreted inclusively rather than exclusively. Accordingly, any list following the word "including" is intended to be illustrative and not intended to be limiting.

The words "comprise," "comprises," and "comprising" in this patent (including the claims) are to be interpreted inclusively rather than exclusively. This interpretation is intended to be the same as the interpretation that these words are given under United States patent law.

The term "BnOH" means benzyl alcohol.
The term "boc" means tert-butyloxycarbonyl.
The term "CDI" means 1,1'-carbonyldiimidazole.
The term "CO$_2$" means carbon dioxide.
The term "DBU" means 2,3,4,6,7,8,9,10-octahydropyrimido[1,2-a]azepine.
The term "DCM" means dichloromethane.
The term "DIPEA" means diisopropylethylamine.
The term "DMF" means dimethylformamide.
The term "dppf" means 1,1'-bis(diphenylphosphino)ferrocene.
The term "DMSO" means dimethyl sulfoxide.
The term "ESI" means electrospray ionization.
The term "EtOH" means ethanol.
The term "GC" means glucocorticoid.
The term "GRE" means glucocorticoid response element.
The term "GR" means glucocorticoid receptor.
The term "$^1$H NMR" means proton nuclear magnetic resonance.
The term "HATU" means 1-[bis(dimethylamino)methylene]-1H-1,2,3-triazolo[4,5-b]pyridinium 3-oxid hexafluorophosphate.
The term "HCl" means hydrochloric acid.
The term "HPLC" means high performance liquid chromatography.
The term "hr" means hour or hours.

The term "LCMS" means liquid chromatography mass spectral detection.
The term "m/z" means mass to charge ratio.
The term "Me" means methyl.
The term "MeI" means methyl iodide.
The term "MeOH" means methanol.
The term "min" means min or min.
The term "MS" means mass spectrum.
The term "MsCl" means methanesulfonyl chloride.
The term "MTBE" means methyl tert-butyl ether.
The term "N$_2$" means nitrogen gas.
The term "NMR" means nuclear magnetic resonance.
The term "NsCl" means 4-nitrobenzenesulfonyl chloride.
The term "(PinB)2" means bis(pinacolato)diboron.
The term "SFC" means supercritical fluid chromatography.
The term "SGRM" means a non-steroidal compound that modulates (i.e., is a partial or complete agonist, a partial or complete antagonist, or is both a partial agonist and partial antagonist) of the glucocorticoid receptor.
The term "TBAF" means tetra-n-butylammonium fluoride.
The term "TBDMSCl" means tert-Butyldimethylsilyl chloride.
The term "TBTU" means 2-(1H-benzo[d][1,2,3]triazol-1-yl)-1,1,3,3-tetramethylisouronium tetrafluoroborate.
The term "TEA" means triethylamine.
The term "TFA" means trifluoroacetic acid.
The term "TFAA" means trifluoroacetic anhydride The above detailed description is intended only to acquaint others skilled in the art with the specification, its principles, and its practical application so that others skilled in the art may adapt and apply the specification in its numerous forms, as they may be best suited to the requirements of a particular use. This specification, therefore, is not limited to the above embodiments, and may be variously modified.

The invention claimed is:

1. A compound or a pharmaceutically acceptable salt thereof, wherein:
the compound corresponds in structure to Formula IA:

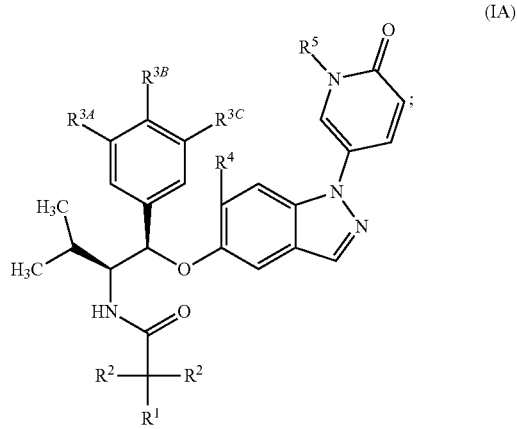

$R^1$ is selected from halo, methyl and halomethyl;
each $R^2$ is an independently selected halo;
each of $R^{3A}$, $R^{3B}$ and $R^{3C}$ is independently selected from H, halo, halomethyl and halomethoxy;
$R^4$ is selected from H, halo and methyl; and
$R^5$ is selected from methyl and ethyl.

2. A compound or pharmaceutically acceptable salt thereof according to claim 1, wherein $R^1$ is methyl.

3. A compound or pharmaceutically acceptable salt thereof according to claim 1, wherein $R^1$ is fluoro.

4. A compound or pharmaceutically acceptable salt thereof according to claim 1, wherein each $R^2$ is fluoro.

5. A compound or pharmaceutically acceptable salt thereof according to claim 1, wherein at least one of $R^{3A}$, $R^{3B}$ and $R^{3C}$ is H.

6. A compound or pharmaceutically acceptable salt thereof according to claim 1, wherein each of $R^{3A}$, $R^{3B}$ and $R^{3C}$ is H.

7. A compound or pharmaceutically acceptable salt thereof according to claim 1, wherein $R^4$ is H.

8. A compound or pharmaceutically acceptable salt thereof according to claim 1, wherein $R^5$ is methyl.

9. A compound or pharmaceutically acceptable salt thereof according to claim 1, wherein the compound is selected from:

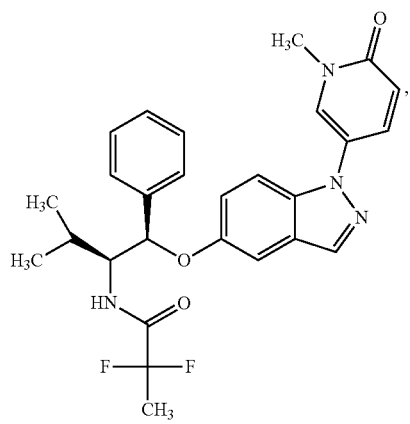

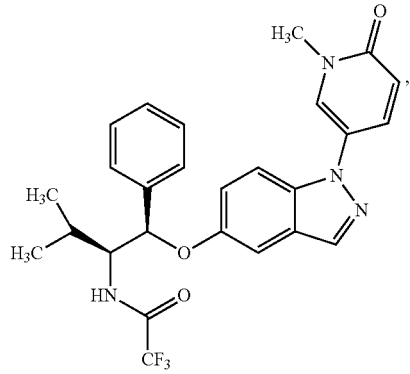

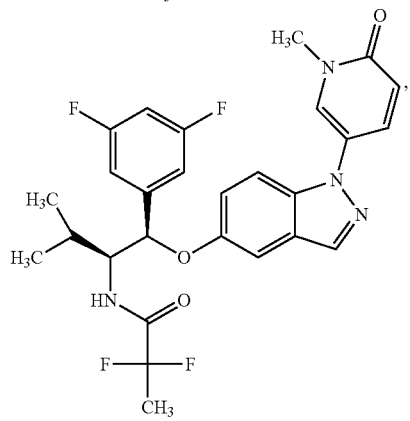

-continued

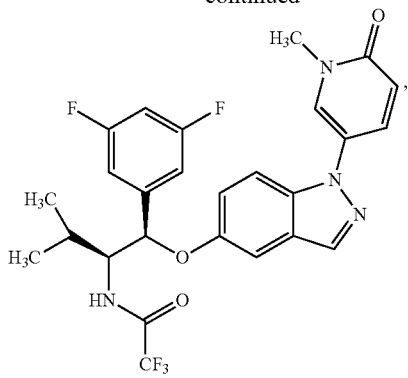

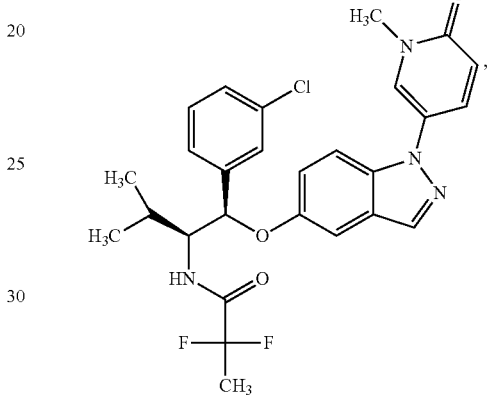

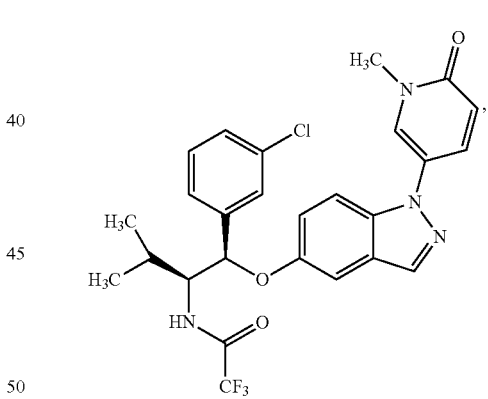

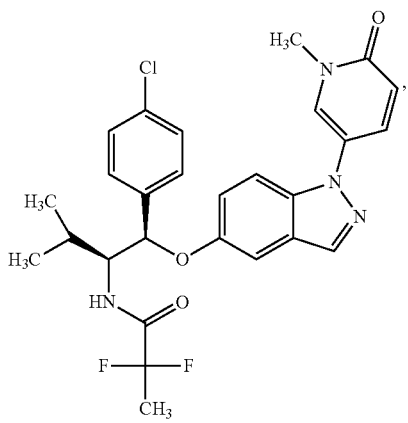 [SMILES: CC(C)[C@H](NC(=O)C(C)(F)F)[C@H](Oc1ccc2c(cnn2-c2ccc(=O)n(C)c2)c1)c1ccccc1]

71
-continued
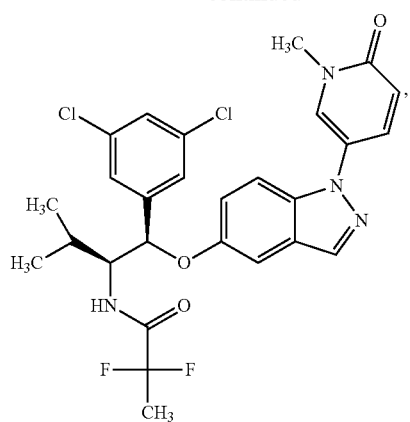
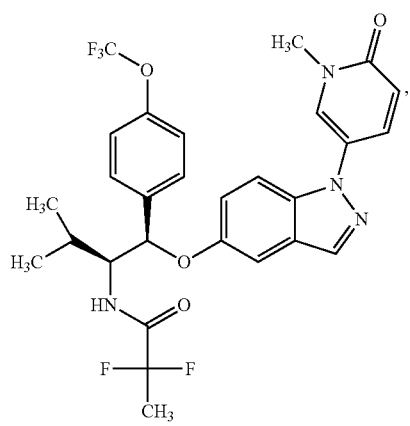
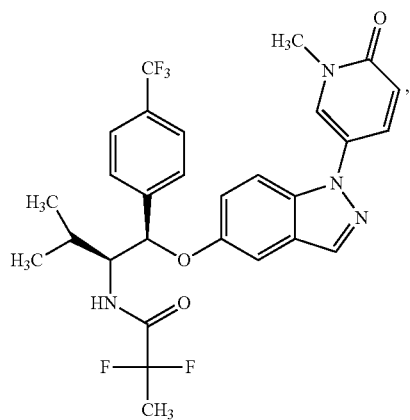
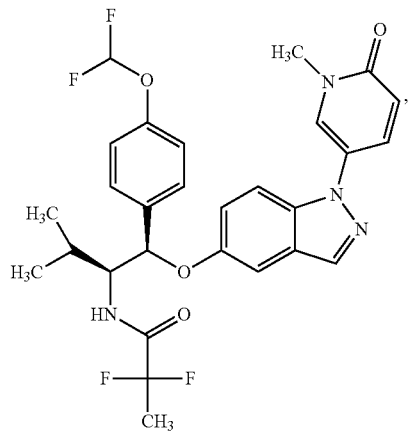
72
-continued
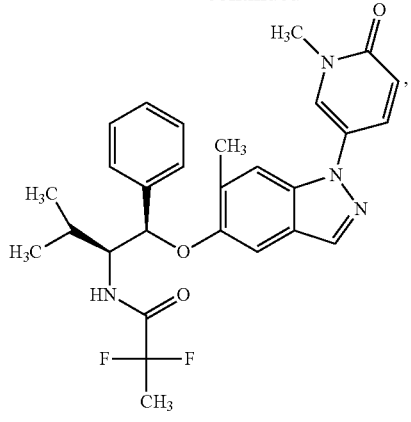
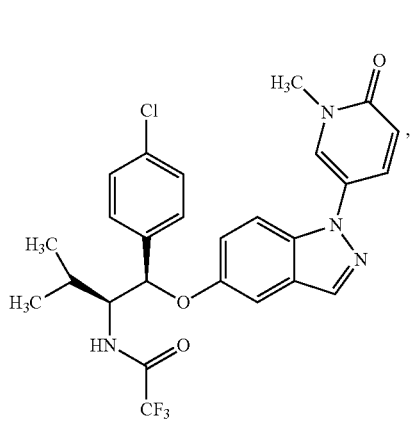
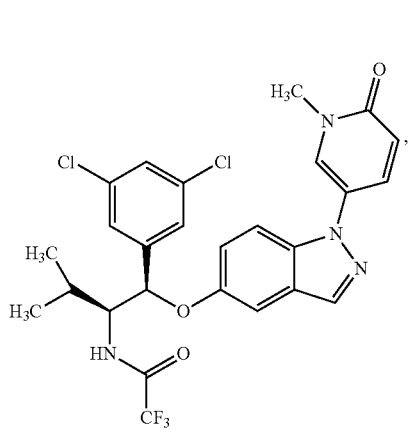
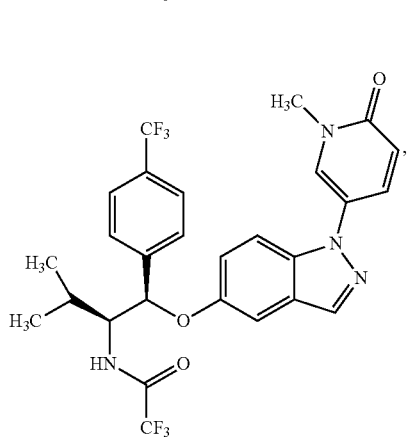

-continued
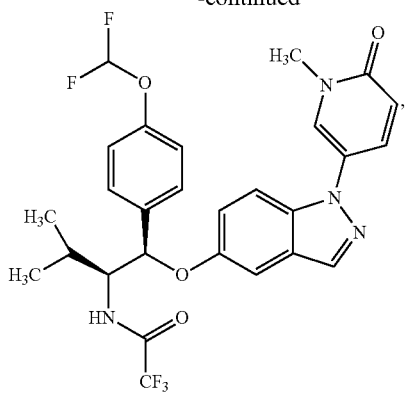
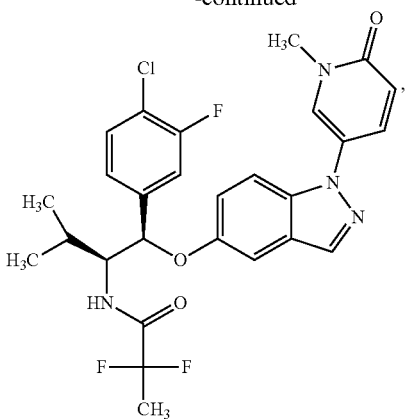
-continued
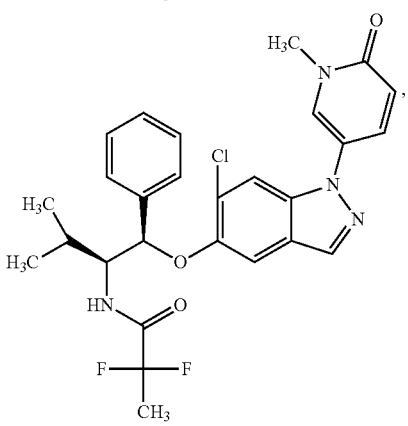
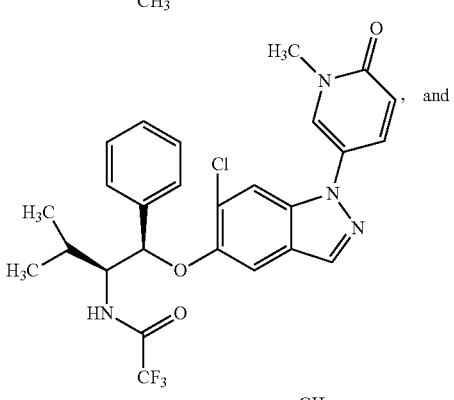
, and
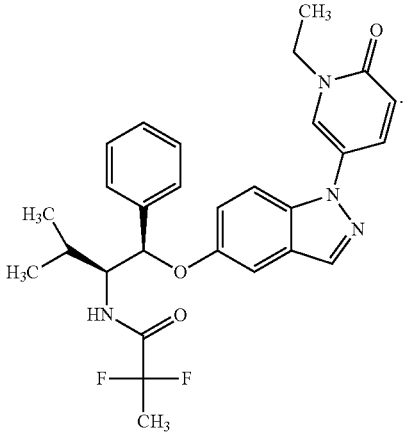
10. A compound or pharmaceutically acceptable salt thereof according to claim 1, wherein the compound is:

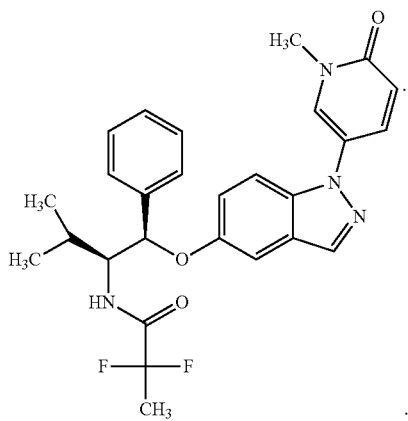

11. A non-salt compound according to claim 1.

12. A pharmaceutically acceptable salt according to claim 1.

13. A pharmaceutically composition comprising:
a therapeutically effective amount of the compound or pharmaceutically acceptable salt thereof according to claim 1, and
an excipient.

14. A method for treating rheumatoid arthritis in a mammal in need of such treatment, wherein the method comprises administering to the mammal a therapeutically effective amount of the compound or pharmaceutically acceptable salt thereof according to claim 1.

15. A method for treating asthma in a mammal in need of such treatment, wherein the method comprises administering to the mammal a therapeutically effective amount of the compound or pharmaceutically acceptable salt thereof according to claim 1.

* * * * *